（12）United States Patent
Tsang et al.

(10) Patent No.: US 7,807,459 B2
(45) Date of Patent: Oct. 5, 2010

(54) EPHA4-POSITIVE HUMAN ADULT PANCREATIC ENDOCRINE PROGENITOR CELLS

(75) Inventors: Wen-Ghih Tsang, Sherman Oaks, CA (US); Yanping Wang, Los Angeles, CA (US); Jinghua Tang, Los Angeles, CA (US)

(73) Assignee: ReNeuron, Inc., Guildford, Surrey (GB)

( * ) Notice: Subject to any disclaimer, the term of this patent is extended or adjusted under 35 U.S.C. 154(b) by 308 days.

(21) Appl. No.: 11/237,094

(22) Filed: Sep. 27, 2005

(65) Prior Publication Data

US 2007/0072292 A1    Mar. 29, 2007

(51) Int. Cl.
C12N 5/02    (2006.01)
C12N 5/071    (2006.01)

(52) U.S. Cl. .................. 435/325; 435/41; 435/70.1; 435/370; 435/374; 424/93.7

(58) Field of Classification Search .................. 435/325, 435/41, 70.1, 370, 374
See application file for complete search history.

(56) References Cited

U.S. PATENT DOCUMENTS 5,985,290 A * 11/1999 Jaffee et al. .............. 424/277.1
6,184,043 B1 * 2/2001 Fodstad et al. .............. 436/526
6,436,704 B1 * 8/2002 Roberts et al. .............. 435/366
6,815,203 B1 * 11/2004 Bonner-Weir et al. ....... 435/377
2005/0013819 A1 * 1/2005 Kinch et al. ............. 424/155.1

OTHER PUBLICATIONS

Langley et al. 1989. Expression of the neural cell adhesion molecule NCAM in endocrine cells. J. Histochem. Cytochem. 37(6):781-791.*
Tezel et al. 2001. Expression of Neural Cell Adhesion Molecule in Pancreatic Cancer. Pancreas. vol. 22:122-125.*
Nakamura et al. 2004. Genome-wide cDNA microarray analysis of gene expression profiles in pancreatic cancers using populations of tumor cells and normal ductal epithelial cells selected for purity by laser microdissection. Oncogene. 23:2385-2400.*
Fujisawa et al. 2003. CD56-positive Cells with or without Synaptophysin Expression are Recognized in the Pancreatic Duct Epithelium: A Study with Adult and Fetal Tissues and Specimens from Chronic Pancreatitis. Acta Med. Okayama, vol. 57, No. 6, pp. 279-284.*

* cited by examiner

Primary Examiner—Taeyoon Kim
(74) Attorney, Agent, or Firm—Morrison & Foerster LLP

(57) ABSTRACT

The invention relates to the discovery of a selective cell surface marker that permits the selection of a unique subset of pancreatic stem cells having a high propensity to differentiate into insulin-producing cells or into insulin-producing cell aggregates.

37 Claims, 30 Drawing Sheets

Fig. 15a                    Fig. 15b
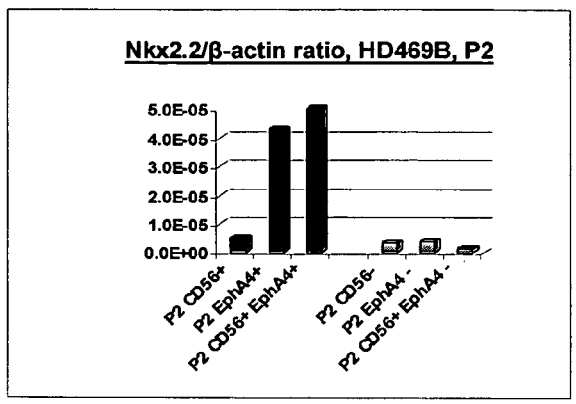
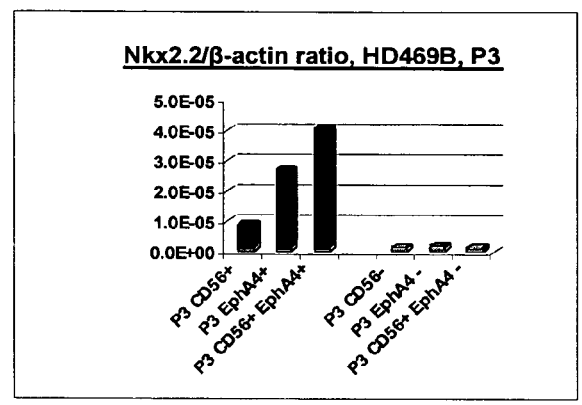
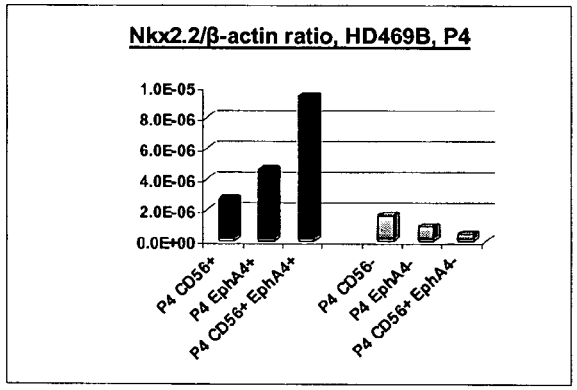
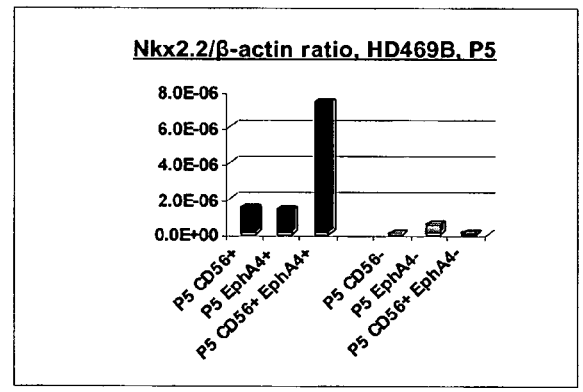
Fig. 15c                    Fig. 15d Fig. 16a  Fig. 16b
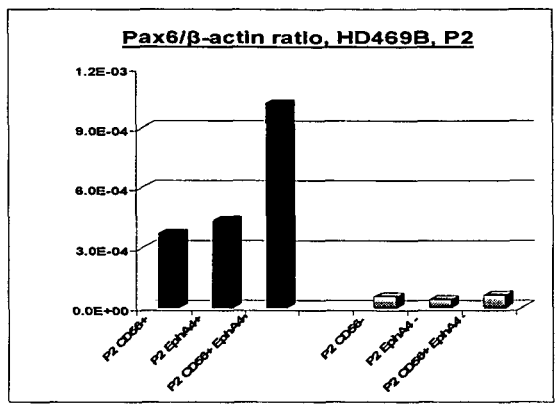
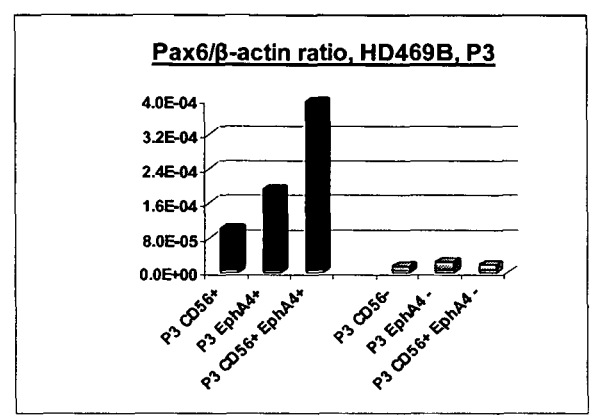
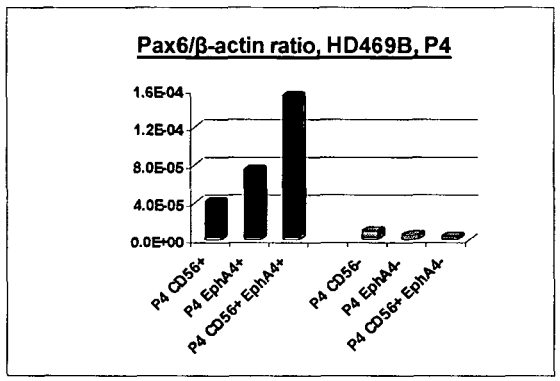
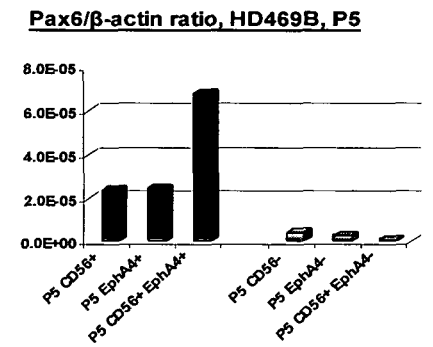
Fig. 16c  Fig. 16d

EPHA4-POSITIVE HUMAN ADULT PANCREATIC ENDOCRINE PROGENITOR CELLS

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Curing type I diabetes would require either the regeneration or the replacement of insulin-producing cells. Islet transplantation has been extensively investigated as a treatment, but the shortage of human donor sources and the low efficiency of islet isolation has largely hampered this therapy. Alternative sources of islets would be desirable. One major focus of study has been the ex vivo cultivation, expansion and differentiation of functional human endocrine cells for clinical applications.

Stem cells offer great potential for cell-replacement therapy. Mouse embryonic stem cells injected into rat striatum were shown to mature into dopaminergic neurones leading to partial recovery in a rat model of Parkinson's disease. Haematopoietic stem cells that regenerate blood cells after bone marrow transplantation are in wide clinical use such as in the treatment of leukemia. Recently, the prospects for using adult stem cells in medical treatments were heightened by Canadian cardiac surgeons, who reported that injecting bone-marrow cells into the heart can boost its function.

Advances in defining the molecular basis of early pancreogenesis have contributed to an understanding of the process of regeneration that occurs in animal models of pancreatic injury and diabetes. However, pancreatic progenitor cell populations remain poorly defined and the subject of considerable debate. The identity of the islet progenitor cells has remained elusive. Identification of the markers that aid the isolation and purification of islet progenitor cell therefore is important to developing regenerated beta-cells in culture for subsequent transplantation into diabetic patients.

Eph receptors, the largest subfamily of receptor tyrosine kinases (RTKs), are important mediators of cell-cell communication regulating cell attachment, shape, and mobility. Eph signaling is crucial for the development of many developmental processes, including embryo patterning, angiogenesis and axon guidance. Emerging evidence also supports a role for these molecules in the formation of adult tissues and organs, such as the nervous and cardiovascular systems.

Both Ephs and ephrins are membrane-bounded and their interaction at sites of cell-cell contact initiate unique bi-directional signaling cascades. Recent studies showed that signaling by Eph receptors controls oocyte maturation in C. elegans by inhibition of MAPK activation demonstrated that EphrinB1 forward and reverse signaling are required during mouse development. Conditional deletion of EphrinB1 revealed that EphrinB1 acts autonomously in neural crest cells and controls their migration. A mutation study in the PDZ binding domain indicated that EphrinB1-induced reverse signaling is required in neural crest cell-derived tissue formation. Those results showed that EphrinB1 acts both as a ligand and as a receptor in a tissue-specific manner during embryognesis.

Combinatorial expression of Eph and Ephrins may define migration and positioning in a wide spectrum of adult tissues. In the small intestine, β-catenin and TCF couple proliferation and differentiation to the sorting of cell populations through controlling the expression the EphB/EphrinB proteins. Eph proteins serve as cell surface markers for monitoring the cell proliferation and differentiation. In vasculogenesis, arteries and veins are morphologically, functionally and molecularly very different. Notch-gridlock(grl) signaling pathway play important role in the development of arteries and veins. Inhibition of grl expression, by gene mutation or antisense RNA, ablates regions of the artery, and expands contiguous regions of the vein, proceed by an increase in expression of the venous marker EphB4 receptor and diminution of expression of the arterial marker EphrinB2.

The findings mentioned above show that Eph widely exists in different epithelial tissues of different species. In an adult animal colon model, Eph expresses only in the proliferating and developing stages of the epithelial cells during normal tissue self renewal, not in stem cells nor in mature cells. Eph also does not express in mesenchymal cells.

BRIEF SUMMARY OF THE INVENTION

The present invention provides methods for obtaining cultures of propagating pancreatic cells and cultures of such cells.

In a first group of embodiments, the invention provides obtaining a culture of propagating pancreatic cells comprising isolating pancreatic cells from a pancreas; contacting the pancreatic cells with an EphA4 binding reagent; selecting pancreatic cells that specifically bind to the EphA4 binding reagent; and separating the selected pancreatic cells from pancreatic cells that do not bind the EphA4 binding reagent to obtain a culture of propagating pancreatic cells. In some embodiments, the EphA4 binding reagent is labeled. In some embodiments, the step of selecting is done by fluorescence activated cell sorting. In some embodiments, the step of selecting is done by panning. In some embodiments, the EphA4-binding reagent is an antibody that specifically binds to the EphA4 protein. In some embodiments, the pancreas is from a human. In some embodiments, the method further comprises propagating the cells of step and differentiating the cells into an aggregate of insulin producing cells. In some embodiments, the step of differentiating the cells comprises culturing the cells on plates coated with collagen IV. In some embodiments, the step of differentiating the cells comprises culturing the cells in a media comprising a differentiation factor. In some embodiments, the differentiation factor is selected from the group consisting of hepatocyte growth factor, keratinocyte growth factor, and exendin-4. In some preferred embodiments, the differentiation factor is hepatocyte growth factor. In some embodiments, the method further comprises contacting the pancreatic cells with a CD56 binding reagent; selecting pancreatic cells that specifically bind to the CD56 binding reagent; and separating the selected pancreatic cells from pancreatic cells that do not bind the CD56 binding reagent to obtain a culture of propagating pancreatic cells. The sorting for cells that specifically bind to the CD56 binding reagent can be performed before contacting the pancreatic cells with the EphA4 binding reagent, or after cells binding the EphA4 binding reagent are separated from pancreatic cells that do not bind the EphA4 binding reagent.

In a further group of embodiments, the invention provides methods of producing an aggregate of insulin-producing pancreatic cells. These methods comprise the steps of isolating pancreatic cells from a pancreas; contacting the pancreatic cells with an EphA4 binding reagent; selecting pancreatic cells that specifically bind to the EphA4 binding reagent; separating the selected pancreatic cells from pancreatic cells that do not bind the CD56 binding reagent to obtain a culture of propagating pancreatic cells; and differentiating the propagating pancreatic cell culture into an aggregate of insulin producing pancreatic cells. In some embodiments, the EphA4 binding reagent is labeled. In some embodiments, the step of selecting is done by fluorescence activated cell sorting. In some embodiments, the step of selecting is done by panning. In some embodiments, the EphA4-binding reagent is an antibody that specifically binds to the EphA4 protein. In some embodiments, the pancreas is from a human. In some embodiments, the method further comprises propagating the cells of step and differentiating the cells into an aggregate of insulin producing cells. In some embodiments, the step of differentiating the cells comprises culturing the cells on plates coated with collagen IV. In some embodiments, the step of differentiating the cells comprises culturing the cells in a media comprising a differentiation factor. In some embodiments, the differentiation factor is selected from the group consisting of hepatocyte growth factor, keratinocyte growth factor, and exendin-4. In some preferred embodiments, the differentiation factor is hepatocyte growth factor. In some embodiments, the method further comprises contacting the pancreatic cells with a CD56 binding reagent; selecting pancreatic cells that specifically bind to the CD56 binding reagent; and separating the selected pancreatic cells from pancreatic cells that do not bind the CD56 binding reagent to obtain a culture of propagating pancreatic cells. The sorting for cells that specifically bind to the CD56 binding reagent can be performed before contacting the pancreatic cells with the EphA4 binding reagent, or after cells binding the EphA4 binding reagent are separated from pancreatic cells that do not bind the EphA4 binding reagent.

In yet another group of embodiments, the invention provides methods of providing pancreatic endocrine function to a mammal in need of such function, comprising the steps of isolating pancreatic cells from a pancreas; contacting the pancreatic cells with an EphA4 binding reagent; selecting pancreatic cells that specifically bind to the EphA4 binding reagent; separating the selected pancreatic cells from pancreatic cells that do not bind the EphA4 binding reagent to obtain a culture of propagating pancreatic cells; and implanting into the mammal the propagating pancreatic cells in an amount sufficient to produce a measurable amount of insulin in the mammal. In some embodiments, the EphA4 binding reagent is labeled. In some embodiments, the step of selecting is done by fluorescence activated cell sorting. In some embodiments, the step of selecting is done by panning. In some embodiments, the EphA4-binding reagent is an antibody that specifically binds to the EphA4 protein. In some embodiments, the pancreas is from a human. In some embodiments, the propagating pancreatic cells differentiate into aggregates of insulin producing pancreatic cells after implantation into the mammal. In some embodiments, before implantation into the mammal, the propagating pancreatic cell culture is differentiated into an aggregate of insulin producing pancreatic cells. In some embodiments, the step of differentiating the cells comprises culturing the cells on plates coated with collagen IV. In some embodiments, the step of differentiating the cells comprises culturing the cells in a media comprising a differentiation factor. In some embodiments, the differentiation factor is selected from the group consisting of hepatocyte growth factor, keratinocyte growth factor, and exendin-4. In some preferred embodiments, the differentiation factor is hepatocyte growth factor. In some embodiments, the mammal is a human. In some embodiments, the method further comprises contacting the pancreatic cells with a CD56 binding reagent; selecting pancreatic cells that specifically bind to the CD56 binding reagent; and separating the selected pancreatic cells from pancreatic cells that do not bind the CD56 binding reagent to obtain a culture of propagating pancreatic cells. The sorting for cells that specifically bind to the CD56 binding reagent can be performed before contacting the pancreatic cells with the EphA4 binding reagent, or after cells binding the EphA4 binding reagent are separated from pancreatic cells that do not bind the EphA4 binding reagent.

In still another group of embodiments, the invention provides methods of monitoring a culture of propagating pancreatic cells by contacting the pancreatic cells with a EphA4 binding reagent; and determining the quantity of cells that exhibit EphA4 as a cell surface marker. In some embodiments, the detecting step is done by fluorescence activated cell sorting. In some embodiments, the EphA4 binding reagent is an antibody that binds specifically to EphA4 protein. In some embodiments, the pancreas is from a human. In some embodiments, the methods further comprise the steps of contacting the pancreatic cells with a CD56 binding reagent; selecting pancreatic cells that specifically bind to the CD56 binding reagent; and determining the quantity of cells that exhibit CD56 and EphA4 as cell surface markers.

In a further group of embodiments, the invention provides cell cultures produced by the steps of: isolating pancreatic cells from a pancreas, contacting the pancreatic cells with an EphA4 binding reagent; selecting pancreatic cells that specifically bind to the EphA4 binding reagent; separating the selected pancreatic cells from pancreatic cells that do not bind the EphA4 binding reagent to obtain a culture of propagating pancreatic cells. In some embodiments, the EphA4 binding reagent is labeled. In some embodiments, the step of selecting is done by fluorescence activated cell sorting. In some embodiments, the step of selecting is done by panning. In some embodiments, the EphA4 binding reagent is an antibody that specifically binds to the EphA4 protein. In some embodiments, the pancreas is from a human. In some embodiments, the steps of producing the cell culture further comprise contacting the pancreatic cells with a CD56 binding reagent; selecting pancreatic cells that specifically bind to the CD56 binding reagent; and separating the selected pancreatic cells from pancreatic cells that do not bind the CD56 binding reagent. In some embodiments, the steps of separating the cells for cells binding the CD56 binding reagent are performed before contacting the pancreatic cells with the EphA4 binding reagent and in some embodiments, they are performed after contacting the pancreatic cells with the EphA4 binding reagent.

BRIEF DESCRIPTION OF THE DRAWINGS

FIG. 2a. Adult human islet, paraffin section. IF EphA4 staining, 100×. EphA4-positive cells were restricted to some islet cells; no positive staining is seen in acinar cells. FIG. 2b. Adult human islet, paraffin section. bright field, 100×. FIG. 2c. Adult human islet, in culture. ABC EphA4 staining, 200×. Expression of EphA4 is found in a subgroup of cultured pancreatic cells. FIG. 2d. Adult human islet, in culture. Phase, 100×.

FIG. 13a: cell passage 2 ("P2"). FIG. 13b: cell passage 3. FIG. 13c: cell passage 4. The horizontal axis shows both cell selections and different culture conditions. FIG. 13d: cell passage 6. The horizontal axis shows both cell selections and different culture conditions. Expression of insulin was evaluated by real-time PCR. As shown in FIGS. 13c and d, the double positive cells maintained high expression of insulin through sequential passages with different culture conditions. The mRNA levels of insulin in CD56-EphA4 double positive cells were always around 2 to 5 times higher than either EphA4 or CD56 single positive selected cells during the passages. Presence of a cell marker on the sorted cells is indicated by a positive sign ("+"), its absence is indicated by a negative sign ("–").

FIG. 14a: PDX-1/Beta-actin expression ratio at P2. FIG. 14b: PDX-1/Beta-actin expression ratio at P3. FIG. 14c: PDX-1/Beta-actin expression ratio at P4. The horizontal axis shows both cell selections and different culture conditions. FIG. 14d: PDX-1/Beta-actin expression ratio at P6. The horizontal axis shows both cell selections and different culture conditions. All Figures: expression of PDX-1 in cells was evaluated by real-time PCR. EphA4/CD56 double positive cells showed higher expression of PDX-1 throughout cell passages P2-P6. During cell passages P3-P6, the expression of PDX-1 was higher in double positive cells than in EphA4 single positive cells. At P2, double positive cells and EphA4 positive cells had similar levels of PDX-1 expression. The results show that selection of double positive cells further enhances the pancreatic endocrine phenotype. Presence of a cell marker on the sorted cells is indicated by a positive sign ("+"), its absence is indicated by a negative sign ("–").

FIGS. 15a-d show a comparison of expression of the pancreatic progenitor marker Nkx2.2 in cells according to their expression of cell markers CD56 and EphA4 at various cell passages. FIG. 15a: Nkx2.2/Beta-actin expression ratio at P2. FIG. 15b: Nkx2.2/Beta-actin expression ratio at P3. FIG. 15c: Nkx2.2/Beta-actin expression ratio at P4. FIG. 15d: Nkx2.2/Beta-actin expression ratio at P5. All Figures: expression of Nkx2.2 in cells was evaluated by real-time PCR. EphA4/CD56 double positive cells showed higher expression of Nkx2.2 throughout the cell passages. The results show that selection of double positive cells further enriched for pancreatic progenitor cells over single selection. Presence of a cell marker on the sorted cells is indicated by a positive sign ("+"), its absence is indicated by a negative sign ("–").

FIGS. 16a-d show a comparison of expression of the pancreatic progenitor marker Pax6 in cells according to their expression of cell markers CD56 and EphA4 at various cell passages. FIG. 16*a*: Pax6/Beta-actin expression ratio at P2. FIG. 16*b*: Pax6/Beta-actin expression ratio at P3. FIG. 16*c*: Pax6/Beta-actin expression ratio at P4. FIG. 16*d*: Pax6/Beta-actin expression ratio at P5. All Figures: expression of Pax6 in cells was evaluated by real-time PCR. EphA4/CD56 double positive cells showed higher expression of Pax6 throughout the cell passages. The results show that selection of double positive cells further enriched for pancreatic progenitor cells over single selection. Presence of a cell marker on the sorted cells is indicated by a positive sign ("+"), its absence is indicated by a negative sign ("−").

FIG. 26*a*: Cells sorted first for CD56 at the end of P0 and then with EphA4 at the end of P1.

FIG. 27*a*: Cells sorted first for CD56 at the end of P0 and then for EphA4 at the end of P1.

DETAILED DESCRIPTION OF THE INVENTION

I. Introduction

Figure 1:
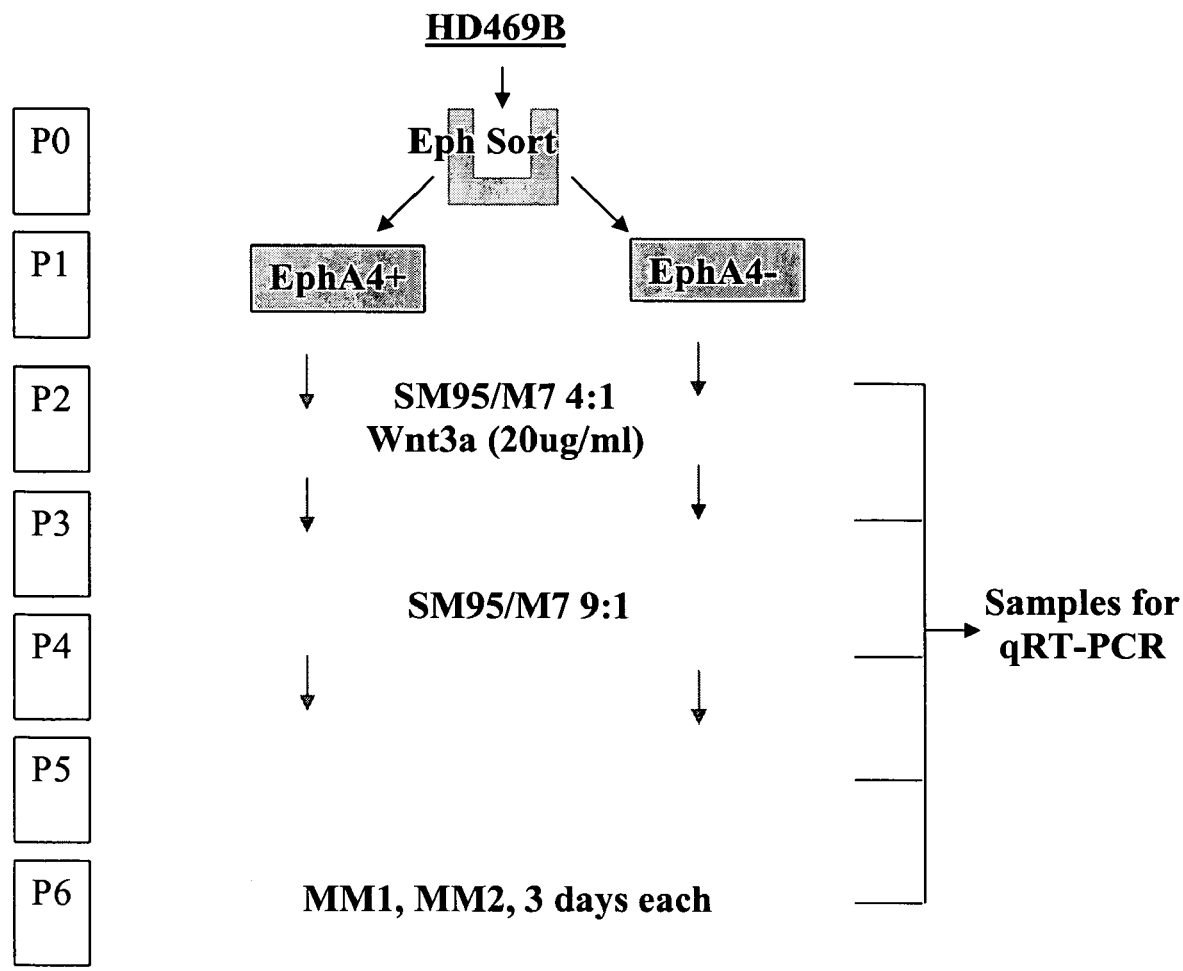
FIG. 1. This figure shows a flow chart for EphA4 sorting and cell culturing. In this and the other Figures, the letter "P" followed by a number designates a given cell passage.

Surprisingly, it has now been discovered that the protein EphA4 is an extracellular marker for progenitors of pancreatic β cells. Sorting pancreatic cells for cells bearing the EphA4 extracellular marker results in a population enriched in pancreatic progenitor cells. EphA4-positive pancreatic cells are capable of being propagated and can be differentiated into aggregates of insulin producing pancreatic cells. Further, pancreatic cells bearing the EphA4 marker can be double-selected for the extracellular marker CD56 provide a population of cells that are even more highly enriched in pancreatic progenitor cells than populations of pancreatic cells sorted by either marker alone. Surprisingly, in an animal model of diabetes, mice transplanted with human pancreatic cells selected by the methods taught herein showed restored normal levels of glucose. Accordingly, it is expected that diabetics can show improved control of glucose levels by transplantation with pancreatic cells selected by the methods of the invention. Thus, the invention provides important new methods for helping diabetic individuals reduce their dependence on exogenously administered insulin.

II. Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"EphA4," or "Ephrin type-A receptor 4" refers to a member of the ephrin-A family with the EC number 2.7.1.112. It is a receptor tyrosine kinase, also known as "tyrosine-protein kinase receptor SEK" and "receptor protein-tyrosine kinase HEK8," while the gene is known as "EPHA4," "SEK," "HEK8," "TYRO1" or "LocusId:2043," and maps on chromosome 2, at 2q36.1. The human form of the protein was originally isolated from fetal brain tissue, as described in Fox et al., "cDNA cloning and tissue distribution of five human EPH-like receptor protein-tyrosine kinases", Oncogene 10:897-905 (1995). The sequence of the precursor form of the human protein is set forth in the Swiss-Prot database under accession number P54764 and can be found on the internet by entering "http://" followed by "us.expasy.org/cgi-bin/niceprot.p1?P54764". EphA receptors bind to GPI-anchored ephrin-A ligands.

"CD56" is a cell surface protein, also known as Neural Cell Adhesion Molecule (N-CAM). CD56 is expressed on neurons, muscle cells, adrenal medulla cells, astrocytes, Schwann cells, NK cells and a subset of activated T cells, including those that are β cell antigen-specific and known to cause Type 1 diabetes. See e.g., Shliakhovenko et al., Vrach Delo 2:453-459 (1991); Mechtersheimer et al., Ann. NY Acad. Sci. 650:311-316 (1992); Leon et al., Brain Res. Dev. Brain Res. 70:109-121 (1992); Pierre et al. Neuroscience 103:133-142 (2001); Hung et al. Glai 38:363-370 (2002); and Ami et al., Clin. Exp Immunol. 128:453-459 (2002). Previous work by one of the present inventors showed that CD56 is also an extracellular marker for progenitors of pancreatic β cells. CD56 has a developmental role in pattern formation, by facilitating cell-cell interactions. Known binding partners of CD 56 include other CD56 proteins and heparin or heparin sulfate. The majority of CD56 proteins are found in three isoforms resulting from differential splicing of mRNA: a 180 kD form, a 140 kD form, and a 120 kD form. CD56 proteins are extensively post-translationally modified. Post translational modifications include addition of asparagine linked oligosaccharides, sulfation of oligosaccharides, phosphorylation of serine and threonine residues, and fatty acid acylation of the protein.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016; Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51

(1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to CD56 proteins, polymorphic variants, alleles, orthologs, and conservatively modified variants, or splice variants, or portions thereof, can be selected to obtain only those polyclonal antibodies that are specifically immunoreactive with CD56 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Specific binding can also be used to describe the interaction of other molecules that specifically bind to CD56 protein, e.g. CD56 ligands and lectins that recognize CD56.

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

As used herein, "insulin producing cells" refers to cells that secrete detectable amounts of insulin. "Insulin producing cells" can be individual cells or collections of cells. One example of a collection of "insulin producing cells" is "insulin producing cell aggregates" e.g., an organized collection of cells with a surrounding mantle of CK-19 positive cells and an inner cell mass. "Aggregate" in the context of cells refers to a three dimensional structure. "CK-19" is a 40 kD acidic keratin, cytokeratin 19. "Mantle" refers to an envelope of cells surrounding in three dimensions the inner cell mass.

The term "contacting" is used herein interchangeably with the following: combined with, added to, mixed with, passed over, incubated with, flowed over, etc.

The term "lectin" refers to protein that recognize specific carbohydrate molecules. In a preferred embodiment the carbohydrate is all or part of an oligosaccharide linked to a CD56 protein molecule.

A "ligand" is a molecule that is specifically bound by a protein. As an example, heparin and heparin sulfate are bound by the CD56 molecule. The term also encompasses molecules that bind to a protein, for example, an antibody that specifically binds to a protein. In some instances the ligand binds to a molecule that is covalently linked to a protein, for example, a carbohydrate or an oligosaccharide.

The terms "heparan or heparin and heparin sulfate" are known to those of skill in the art. Heparin and heparin sulfate are examples of glycosaminoglycans.

The term "FACS" refers to fluorescence activated cell sorting, a technique used to separate cells according to their content of particular molecules of interest. The molecule of interest can be specific for a type of cell or for particular cell state. The molecule of interest can be fluorescently labeled directly by binding to a fluorescent dye, or by binding to a second molecule, which has been fluorescently labeled, e.g., an antibody or lectin that has been fluorescently labeled and that specifically binds to the molecule of interest. In a preferred embodiment, a fluorescently labeled EphA4 specific antibody is used to separate EphA4-positive cells from EphA4-negative cells.

The term "panning" refers to a method of selecting cells that bind to, as appropriate in context, a EphA4- or CD56- binding reagent. A flat surface, e.g., a culture dish, is coated with the chosen binding reagent. Pancreatic cells are added to the surface and allowed to bind to the binding reagent. The culture dishes are then washed, removing the cells that have not bound (that is, cells that are either EphA4- or CD56-negative, depending on the binding reagent used) from the dish. In a preferred embodiment, an EphA4-specific antibody is used to coat a culture dish and "pan" for EphA4-positive cells in a population of pancreatic cells.

"Differentiate" or "differentiation" refers to a process where cells progress from an undifferentiated state to a differentiated state or from an immature state to a mature state. For example, undifferentiated pancreatic cells are able to proliferate and express characteristics markers, like PDX-1. Mature or differentiated pancreatic cells do not proliferate and secrete high levels of pancreatic endocrine hormones. E.g., mature β-cells secrete insulin at high levels. Changes in cell interaction and maturation occur as cells lose markers of undifferentiated cells or gain markers of differentiated cells. Loss or gain of a single marker can indicate that a cell has "matured or differentiated."

The term "differentiation factors" refers to a compound added to pancreatic cells to enhance their differentiation to mature insulin producing β cells. Exemplary differentiation factors include hepatocyte growth factor, keratinocyte growth factor, exendin-4, basic fibroblast growth factor, insulin-like growth factor-I, nerve growth factor, epidermal growth factor and platelet-derived growth factor.

The term "providing pancreatic function to a mammal in need of such function" refers to a method of producing pancreatic hormones within the body of a mammal unable to produce such hormones on its own. In a preferred embodiment, insulin is produced in the body of a diabetic mammal. The pancreatic function is provided by implanting or transplanting aggregates of insulin producing pancreatic cells, produced by the methods of this disclosure into the mammal. The number of aggregates implanted is an amount sufficient to produce a measurable amount of insulin in the mammal. The insulin can be measured by Western blotting or by other detection methods known to those of skill in the art, including assays for insulin function, such as maintenance of blood glucose levels. Insulin can also be measured by detecting C-peptide in the blood. In another preferred embodiment, the provision of pancreatic function is sufficient to decrease or eliminate the dependence of the mammal on insulin produced outside the body.

"Encapsulation" refers to a process where cells are surrounded by a biocompatible acellular material, such as sodium alginate and polylysine. Preferably small molecules, like sugars and low molecular weight proteins, can be taken up from or secreted into an environment surrounding the encapsulated cells. At the same time access to the encapsulated cells by larger molecules and immune cells is limited.

"Implanting" is the grafting or placement of the cells into a recipient. It includes encapsulated cells and non-encapsulated. The cells can be placed subcutaneously, intramuscularly, intraportally or interperitoneally by methods known in the art.

A "population" of cells refers to a plurality of cells obtained by a particular isolation or culture procedure. While the selection processes of the present invention yield populations with relatively uniform properties, a population of cells may be heterogeneous when assayed for marker expression or other phenotype. Properties of a cell population are generally defined by a percentage of individual cells having the particular property (e.g., the percentage of cells staining positive for a particular marker) or the bulk average value of the property when measured over the entire population (e.g., the amount of mRNA in a lysate made from a cell population).

"Passage" of cells usually refers to a transition of a seeded culture container from a partially confluent state to a confluent state, at which point they are removed from the culture container and reseeded in a culture container at a lower density. However, cells may be passaged prior to reaching confluence. Passage typically results in expansion of the cell population as they grow to reach confluence. The expansion of the cell population depends on the initial seeding density but is typically a 1 to 10, 1 to 5, 1 to 3, or 1 to 2 fold expansion. Thus, passaging generally requires that the cells be capable of a plurality of cell divisions in culture.

III. Isolation of EphA4 Positive Pancreatic Cells

Those of skill in the art will recognize that a variety of sources and methods can be used to isolate EphA4 positive pancreatic cells.

A. Isolation of Pancreas from a Donor

Pancreatic cells isolated for subsequent culturing are obtained from one or more donated pancreases. The methods described herein are not dependent on the age of the donated pancreas. Accordingly, pancreatic material isolated from donors ranging in age from embryos to adults can be used.

In another embodiment, pancreatic cells are isolated from a cultured source. For example, cells prepared according to the microencapsulation method of U.S. Pat. No. 5,762,959 to Soon-Shiong, et al., entitled "Microencapsulation of cells," can be harvested as a source of donor cells.

1. Isolation of Pancreatic Cells from Pancreas

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations (see U.S. Pat. Nos. 5,830,741 and 5,753,485) and other enzymes are contemplated for use with the methods disclosed herein.

Isolated source material can be further processed to enrich for one or more desired cell populations. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e.g., Nycodenz®, Ficoll®, or Percoll®). For example the gradient method described in U.S. Pat. No. 5,739,033, can be used as a means for enriching the processed pancreatic material in islets. The mixture of cells harvested from the donor source will typically be heterogeneous and thus contain α-cells, β-cells, δ-cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is islet-enriched and typically contains 10 to 100% islet cells in suspension. The second interface is typically a mixed population of cells containing islets, acinar, and ductal cells. The bottom layer is the pellet, which is formed at the bottom of the gradient. This layer typically contains primarily (>80%) acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation. When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one embodiment, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped islet cells, respectively, can also be used in culture. While both layers contain cells capable of giving rise to the EphA4-positive population described herein, each layer may have particular advantages for use with the disclosed methods.

B. Selection of EphA4 Positive Pancreatic Cells

Once a source of pancreatic cells have been chosen, EphA4 positive cells can be selected and then separated from cells that do not express EphA4. Those of skill in the art will recognize that a variety of methods can be used to select EphA4-positive cells and separate those cells from EphA4-negative cells.

1. Detection of EphA4 Positive Cells Using Molecules that Bind EphA4

Those of skill in the art will recognize that there are many methods to detect EphA4 protein. For example, antibodies that bind specifically to the EphA4 protein can be used to detect EphA4. Antibodies specific to the EphA4 protein are known to those of skill in the art and are commercially available from, for example, Abcam (Cambridge, United Kingdom), BD Biosciences Pharmingen (San Diego, Calif.), Gene Tex (San Antonio, Tex.), Novus Biologicals (Littleton, Calif.) and Upstate Group LLC (Charlottesville, Va.). In addition to antibodies, other molecules that bind specifically to EphA4 can be used to identify EphA4-positive cells.

Those of skill in the art will recognize that molecules that bind specifically to EphA4 are particularly useful if they are labeled and thus able to be detected by some means. A "label" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

2. FACS to Select EphA4 Positive Cells

Fluorescently labeled molecules that bind specifically to EphA4, most commonly antibodies, are used to select EphA4 positive cells in conjunction with a Fluorescence Activated Cell Sorter ("FACS"). Briefly, pancreatic cells are incubated with fluorescently-labeled antibody and after the antibody binding, the cells are analyzed by FACS. The cell sorter passes single cells suspended in liquid through a fluorimeter. The amount of fluorescence is measured and cells with fluorescence levels detectably higher than control, unlabeled, cells are selected as positive cells.

FACS can also be used to physically separate cell populations based on measurement of fluorescence. The flowing cells are deflected by electromagnetic fields whose strength and direction are varied according to the measured intensity of the fluorescence signal. Labeled EphA4-positive cells can be deflected into a separate container and thus, separated from unlabeled, EphA4-negative cells.

After pancreatic cells are isolated from pancreas, the cells are first cultured for one to two passages and then labeled with a EphA4-specific antibody. The cells are then scanned using FACS to separate EphA4-positive from EphA4-negative cells. Up to 98% of the cells are deemed negative for EphA4.

Many different fluorescent molecules are available for conjugation to antibodies, for example fluorescien or rhodamine. Those of skill are aware that in some instances more than one extracellular marker can be detected by using different antibodies conjugated to fluorescent molecules. FACS analysis can be done under conditions to identify more than one extracellular marker of interest. In some embodiments, antibodies to EphA4 and antibodies to CD56 are chosen to "double select" for cells bearing these markers, as discussed elsewhere in this disclosure.

3. Affinity Adsorbing EphA4-positive Cells onto a Solid Support.

EphA4-positive cells can be separated from EphA4-negative cells by using EphA4-specific binding molecules attached to a solid support. Those of skill in the art will recognize that EphA4-specific antibodies can be bound to a solid support through an antibody binding molecule, such as protein G or protein A or alternatively, can be conjugated to a solid support directly.

EphA4-positive cells can also be separated from EphA4-negative cells through the technique of panning. Panning is done by coating a solid surface with a EphA4-binding reagent and incubating pancreatic cells on the surface for a suitable time under suitable conditions. A flat surface, e.g., a culture dish, is coated with a EphA4-binding reagent. Pancreatic cells are added to the surface and allowed to bind to the EphA4-binding reagent. The culture dishes are then washed, removing the EphA4-negative cells from the dish. In a preferred embodiment, a EphA4-specific antibody is used to coat a culture dish and "pan" for EphA4-positive cells in a population of pancreatic cells.

In some embodiments, the solid support is a bead or particle which is coated with anti-EphA4 antibodies. EphA4-positive cells then bind to the bead or particle and can be separated from the EphA4-negative cells by any of a number of methods, such as by washing the media containing the cells through a screen with openings sized to permit unbound (EphA4-negative) cells to pass through, while retaining beads or particles to which EphA4-positive cells have bound. In a preferred group of embodiments, the beads are magnetic. The use of magnetic beads facilitates the separation step.

IV. Cell Culture and Cultivation of EphA4-Positive Cells and their Progeny

A. General Cell Culture Procedures

Once the pancreatic cells are obtained and isolated, they are cultured under conditions that select for propagation of the desired EphA4-positive population, or in other embodiments, for the differentiation of more mature cell types. General cell culture methodology may be found in Freshney, *Culture of Animal Cells: A Manual of Basic Technique* 4th ed., John Wiley & Sons (2000). Typically, pancreatic cells are cultured under conditions appropriate to other mammalian cells, e.g., in humidified incubators at 37° C. in an atmosphere of 5% $CO_2$. Cells may be cultured on a variety of substrates known in the art, e.g., borosilicate glass tubes, bottles, dishes, cloning rings with negative surface charge, plastic tissue culture tubes, dishes, flasks, multi-well plates, containers with increased growth surface area (GSA) or Esophageal Doppler Monitor (EDM) finish, flasks with multiple internal sheets to increase GSA, Fenwal bags, and other culture containers.

Once the pancreatic cellular material has been harvested and selected for culture, or once a population is confluent and is to be transferred to a new substrate, a population of cells is seeded to a suitable tissue culture container for cultivation. Seeding densities can have an effect on the viability of the pancreatic cells cultured using the disclosed methods, and optimal seeding densities for a particular culture condition may be determined empirically by seeding the cells at a range of different densities and monitoring the resulting cell survival and proliferation rate. A range of seeding densities has been shown to be effective in producing hormone secreting cells in culture. Typically, cell concentrations range from about $10^2$ to $10^8$ cells per 100 mm culture dish, e.g., $10^2$, $10^3$, $10^4$, $10^5$, $10^6$, $10^7$, or $10^8$ cells per 100 mm culture dish, although lower cell concentrations may be employed for cloning procedures. Cell concentration for other culture vessels may be adjusted by computing the relative substrate surface area and/or medium gas exchange surface area for a different culture vessel. For example, a typical 100 mm culture dish has a substrate surface area of 55 square centimeters (see Freshney, supra), and a cell concentration of 10,000 cells per dish corresponds to about 180 cells per square centimeter, while a cell concentration of 100,000 cells per dish corresponds to about 1,800 cells per square centimeter. Cell concentration in terms of culture vessel surface area may be related to cell concentration in terms of media volume by using the appropriate media volume per culture surface area (0.2-0.5 ml/cm$^2$ are typical ranges for static culture). To determine if a 10 fold expansion has occurred, the cells are removed by enzymatic digestion and counted under microscope in a known volume of fluid. Cells may also be grown on culture surfaces pre-coated with defined extracellular matrix components to encourage growth and differentiation (e.g., fibronectin, Collagen I, Engelbreth-Holm-Swarm matrix, and, preferably, collagen IV or laminin).

Standard cell culture propagation techniques are suitable for practice of the invention. When cells are growing attached to a culture surface, they are typically grown as a monolayer until 80%-90% confluence is reached, at which point the cells are released from the surface by proteolytic digestion and split 1:2 or 1:3 for culture in new vessels. Higher dilutions of the cells are also suitable, generally between the ranges of 1:4 to 1:10, although even lower cell concentrations are appropriate in cloning procedures. Concentrations of proteolytic enzymes and chelating agents are usually lowered when cells are passaged in serum-free media (e.g., 0.025% trypsin and 0.53 mM EDTA). Culture medium is typically changed twice weekly or when the pH of the medium indicates that fresh medium is needed.

The pancreatic cells of the present invention may be cultured in a variety of media. As described herein, media containing or lacking particular components, especially serum, are preferred for certain steps of the isolation and propagation procedures. For example, cells freshly isolated from the pancreas may be maintained in high serum medium to allow the cells to recover from the isolation procedure. Conversely, low serum medium favors the selection and propagation of an intermediate stage population. Accordingly, a number of media formulations are useful in the practice of the invention. The media formulations disclosed here are for exemplary purposes, and non-critical components of the media may be omitted, substituted, varied, or added to simply by assaying the effect of the variation on the replication or differentiation of the cell population, using the assays described herein. See, e.g., Stephan et al., *Endocrinology* 140:5841-54 (1999)).

Culture media usually comprise a basal medium, which includes inorganic salts, buffers, amino acids, vitamins, an energy source, and, in some cases, additional nutrients in the form of organic intermediates and precursors that are involved in protein, nucleic acid, carbohydrate, or lipid metabolism. Basal media include F12, Eagle's MEM, Dulbecco's modified MEM (DMEM), RPMI 1640, a 1:1 mixture of F12 and DMEM, and others. See Freshney, supra. To support the growth of cells, basal medium is usually supplemented with a source of growth factors, other proteins, hormones, and trace elements. These supplements encourage growth, maintenance, and/or differentiation of cells, compensate for impurities or toxins in other medium components, and provide micronutrients lacking in the basal medium. In many culture media, serum is the source of these supplements. Serum can be supplied from a variety of mammalian sources, such as human, bovine, ovine, equine, and the like, and from adult, juvenile, or fetal sources. See Freshney, supra. Fetal bovine serum is a commonly used supplement. Concentrations of serum are expressed in terms of volume of serum as a percentage of the total medium volume, and typically range from about 0.1 to 25%, e.g., about 0.1, 0.2, 0.5, 1, 2, 3, 4, 5, 6, 7, 8, 9, 10, 15, 20, or 25%. In some applications, the basal medium is supplemented with defined or semi-defined mixtures of growth factors, hormones, and micronutrients, rather than with serum. Formulas for serum replacement supplements are disclosed herein; others are known in the art or available from commercial sources (see Freshney, supra). For some embodiments, the concentration of serum is lowered but not eliminated, and defined or semi-defined supplement mixtures are added to the basal medium. Preferred applications for media containing high or low concentrations of serum are described herein.

B. Maintenance and Propagation of Isolated Pancreatic Cells in Media Containing High Serum Cells harvested from a donor pancreas have usually undergone a period of warm or cold ischemia between the death of the donor and the beginning of the isolation procedure. Moreover, during the isolation procedure, pancreatic cells are usually subjected to proteolytic digestion as well as mechanical and shear stresses. Without wishing to be bound by a particular theory, the various traumas experienced by these cells may up-regulate various cellular processes that result in the expansion of pancreatic stem cell populations, such as facultative progenitor cells. Intermediate cell populations may be generated with satisfactory efficiency by placing cells into low serum media directly after isolation or purification. Nonetheless, because the trauma experienced by cells during the isolation procedures may have adverse effects on cell survival and adaptation to culture, it is sometimes desirable to maintain the freshly isolated cells in a stabilizing medium containing high concentrations of serum (e.g., >4%) to improve the efficiency of the culturing process. This maintenance period may be brief (e.g., overnight). Optionally, cells may be maintained for an extended propagation period in high serum medium.

High serum media for stabilization will typically contain at least 4% serum, and, in some embodiments, will contain a higher concentration of serum such as 10% or 20%. Media used for stabilization or propagation may be derived from a basal medium such as RPMI 1640, available from many commercial sources and described by Moore et al., *J Am Med Assoc* 199:519-524 (1967)). Exemplary high serum media for maintenance or propagation include Medium 3 (RPMI 1640+ 10 mM HEPES, 2 mM glutamine, 5 µM $ZnSO_4$, and 10% fetal bovine serum (FBS)) and Medium 7 (RPMI 1640+10 mM HEPES, 2 mM glutamine, 5 µM $ZnSO_4$, and 20% FBS). High serum media may also be derived by mixing a particular volume of high serum medium such as Medium 3 or Medium 7 with a particular volume of serum-free medium such as SM95, SM96, or SM98 (described herein) to arrive at a desired serum concentration (e.g., 4%-9%).

For stabilization after harvest, cells are conveniently cultured in a culture vessel at relatively high densities in a high serum medium (e.g., $10^9$ cells in 70 ml of Medium 7 (20% FBS)). However, lower cell densities and serum concentrations may be employed as well. Cells are typically maintained in the original vessel for a relatively short time (e.g., overnight) to allow for recovery from the harvesting procedure.

Following the maintenance period, cells may be transferred to low serum media for selection and propagation of the EphA4-positive cell population as described herein. Optionally, the cells may be cultured in a high serum medium to allow for proliferation of the mixed cell population. In a typical embodiment, cells from the maintenance culture are reseeded into a new culture vessel containing Medium 3 (10% FBS), Medium 7 (20% FBS), or a mixture of Medium 3 and Medium 7 (15% FBS), or other AmCyte culture media. Cells are typically cultured in this medium for 7-10 days, during which time they may grow to confluence. Once the cells have reached confluence, they may be passaged into low serum media for selective expansion of the intermediate cell population described herein.

C. Expansion and Propagation of a EphA4 Positive Pancreatic Cell Population by Culture in Media Containing Low Serum Once the pancreatic cells have been isolated, the cells are then transferred to a selective medium to promote the emergence of a propagating intermediate stage population. This selective medium favors propagation of cells which retain the ability to secrete pancreatic endocrine hormones, or which retain the potential to mature into more differentiated cells which secrete high levels of pancreatic endocrine hormones. In general, selective medium will favor propagation of epithelial or epithelial-like cells at the expense of fibroblasts and mesenchymal cells, although pure epithelial cultures have not been shown to be required for the advantageous use of pancreatic cells in the methods of the invention. Typically, epithelial-selective media will yield a population of nearly pure (e.g., <10% fibroblasts or mesenchymal cells) cells after a certain period of growth in culture, e.g., 2, 3, 4, or 5 passages depending on the expansion of the population in each passage.

One type of selective medium which has been employed to favor epithelial cell growth from embryonic tissues is serum-free medium (see, e.g., Stephan et al., supra; Peehl and Ham, In Vitro 16:526-40 (1980)). Epithelial-specific media, and, more preferably, low serum media containing a source of growth hormone, may be employed to select for a distinct population of propagating pancreatic cells from adult mammals that retain markers of pancreatic cell development (e.g., PDX-1), but can be further differentiated under appropriate conditions to express high levels of pancreatic endocrine hormones. Particular epithelial-selective media suitable for culture of pancreatic cells are disclosed herein, but other medium formulations known in the art to favor the preferential expansion of epithelial or epithelial-like cells may also be employed.

The transfer to epithelial-selective low serum medium may be accomplished after a period of maintenance in high serum medium ("weaning"), or by transferring the cells directly into selective low serum medium following the isolation and separation procedure ("shock"). Either methodology is suitable for generation of the desired intermediate cell population.

1. Supplements

Typical ingredients added to basal media for complete serum-free media include recombinant human insulin (0.1 to 100 µg/ml), transferrin (0.1 to 100 µg/ml), epidermal growth factor (0.1 to 100 ng/ml), ethanolamine (0.1 to 100 µg/ml), aprotinin (0.1 to 100 µg/ml), glucose (0.1 to 100 mg/ml), phosphoethanolamine (0.1 to 100 µM), triiodothyronone (0.1 to 100 µM), selenium (0.1 to 100 nM), hydrocortisone (0.01 to 100 nM), progesterone (0.1 to 10 nM), forskolin (0.1 to 100 µM), heregulin (0.1 to 100 nM), and bovine pituitary extract (0.1 to 500 µg/ml). Not all supplemental ingredients are required to support cell growth; the optimal concentration or necessity for a particular supplement may be determined empirically, by leaving out or reducing the concentration of a single ingredient and observing the effect on cell proliferation. See e.g., Stephan et al., supra.

In general, supplemental ingredients may be replaced by natural or synthetic products that have the same biological properties. For example, triiodothyronone, hydrocortisone, and progesterone may all be replaced by natural or synthetic hormones known to activate the same intracellular receptors (thyroid receptors, glucocorticoid receptors, and progesterone receptors). Insulin and EGF are typically human proteins produced by recombinant DNA methodology, but may be replaced by polypeptides purified from natural sources, by polypeptides from other species, or by other agonists of the insulin and EGF receptors. Growth hormone ("GH", mature human growth hormone is a 191-amino acid peptide which displays a molecular mass of 22 kD) may be used or, in some cases, may be substituted with other agents which bind to the GH receptor. Likewise, heregulin, a ligand of the ErbB3 receptor, may be replaced by heregulin isoforms and other ErbB3 agonists such as NRG2, NRG3, and NRG4, sensory and motor neuron-derived factor, neurestin, and Ebp-1, heregulin α, heregulin β, heregulin γ, neuregulin-1 and neuregulin-2 (NRG-1 alpha, NRG-1beta, NRG-2 alpha, and NRG-2 beta.

Exemplary serum-free media include the basal medium SM96 and the complete medium SM95, which consists of SM96 supplemented as shown in the following tables. SM98 consists of 1:1 F12/DMEM supplemented with a modification of medium supplement 14F described by Stephan et al., supra. SM98 contains less heregulin (1 ng/ml v. 8 ng/ml) than 14F. Thus, SM 98 consists of 1:1 F12/DMEM supplemented with recombinant human insulin, 10 µg/ml; transferrin, 10 µg/ml; epidermal growth factor, 10 ng/ml; ethanolamine, 61 ng/ml; aprotinin, 25 µg/ml; glucose, 5 mg/ml; phosphoethanolamine, 141 ng/ml; triiodothyronone, 3.365 pg/ml; selenium, 4.325 ng/ml; hydrocortisone, 181 ng/ml; progesterone, 3.15 ng/ml; forskolin, 410 ng/ml; heregulin, 1 ng/ml; and bovine pituitary extract, 75 µg/ml. Exemplary sources of EGH and heregulin in SM95 and SM98 are recombinant human EGF (Sigma-Aldrich Co., St. Louis, Mo., catalog number E9644) and the EGF domain (amino acids 176-246) of human heregulin-β1 (R&D Systems Inc., Minneapolis, Minn., catalog number 396-HB/CF).

| RPMI 1640 Media (Moore, et al., A.M.A., 199:519 (1967)) | Mg/L |
|---|---|
| INORGANIC SALTS | |
| Ca(NO$_3$)$_2$·4H$_2$O | 100 |
| KCl | 400.00 |
| MgSO$_4$ (anhyd.) | 48.84 |
| NaCl | 5850.00 |
| Na$_2$HPO$_4$ (anhyd.) | 800.00 |
| OTHER COMPONENTS | |
| D-Glucose | 2000.00 |
| Glutathione (reduced) | 1.0 |
| HEPES | 5958.00 |
| Phenol Red | 5.00 |
| AMINO ACIDS | |
| L-Arginine | 200.00 |
| L-Asparagine (free base) | 50.00 |
| L-Aspartic Acid | 20.00 |
| L-Cystine·2HCl | 65.00 |
| L-Glutamic Acid | 20.00 |
| L-Glutamine | 300.00 |
| Glycine | 10.00 |
| L-Histidine (free base) | 15.00 |
| L-Isoleucine | 50.00 |
| L-Leucine | 50.00 |
| AMINO ACIDS | |
| L-Lysine·HCl | 40.00 |
| L-Methionine | 15.00 |
| L-Phenylalanine | 15.00 |
| L-Proline | 20.00 |
| L-Serine | 30.00 |
| L-Threonine | 20.00 |
| L-Tryptophan | 5.00 |
| L-Tyrosine·2Na$_2$H$_2$O | 29.00 |
| L-Valine | 20.00 |
| VITAMINS | |
| Biotin | 0.20 |
| D-Ca Pantothenate | 0.25 |
| Choline Chloride | 3.00 |
| Folic Acid | 1.00 |
| i-Inositol | 35.00 |
| Niacinamide | 1.00 |
| Pyridoxine·HCl | 1.00 |
| Riboflavin | 0.20 |
| Thiamine·HCl | 1.00 |
| Thymidine | 0.005 |
| Vitamin B$_{12}$ | 1.04 |

| SM95 | Mg/L |
|---|---|
| INORGANIC SALTS | |
| CaCl$_2$ | 78.3 |
| CuSO$_4$·5H$_2$O | 0.00165 |
| Fe(NO$_3$)$_3$·9H$_2$O | 0.025 |
| FeSO$_4$·7H$_2$O | 0.61 |
| KCl | 271 |
| MgCl$_2$ | 28.36 |
| MgSO$_4$ | 39.06 |
| KH$_2$PO$_4$ | 34 |
| NaCl | 7262.75 |
| NaHCO$_3$ | 1600 |
| Na$_2$HPO$_4$ | 101.5 |
| NaH$_2$PO$_4$·H$_2$O | 31.25 |
| ZnSO$_4$·7H$_2$O | 0.416 |
| AMINO ACIDS | |
| L-Alanine | 11.225 |
| L-Arginine·HCl | 283.75 |
| L-Asparagine·H$_2$O | 18.75 |
| L-Aspartic Acid | 16.325 |
| L-Cysteines·H$_2$O(non-animal) | 43.78 |
| L-Cystine·2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl·H$_2$O | 38.69 |
| L-Isoleucine | 31.24 |
| L-Leucine | 42.5 |
| L-Lysine·HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine·2Na$_2$H$_2$O (non-animal) | 35.9 |
| L-Valine | 38.125 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine·2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| L-Inositol | 24.3 |
| Niacinamide | 1.03 |
| Pyridoxine·HCl | 1.046 |
| Riboflavin | 0.13 |
| Thiamine·HCl | 1.23 |
| Thymidine | 0.5325 |
| Vitamin B$_{12}$ | 1.04 |
| SUPPLEMENTS | |
| Na Selenous Acid | 0.0034 |
| Epithelial Growth Factor | 0.005 |
| Ethanolamine | 0.03 |
| Phosphoethanolamine | 0.07 |
| Aprotinin | 12.5 |
| Progesterone | 0.0016 |
| Forskolin | 0.205 |
| HeregulinB | 0.004 |
| Bovine Pituitary Extract | 37.5 |
| Hydrocortisone | 0.0923 |
| r.h. insulin | 5.05 |
| T$_3$ | 0.0000015 |
| L-Thyroxine Na | 0.00002 |
| Bovine Transferrin APG | 7.5 |

| SM96 | |
|---|---|
| | Mg/L |
| INORGANIC SALTS | |
| $CaCl_2$ | 78.3 |
| $CuSO_4 \cdot 5H_2O$ | 0.00165 |
| $Fe(NO_3)_3 \cdot 9H_2O$ | 0.025 |
| $FeSO_4 \cdot 7H_2O$ | 0.61 |
| KCl | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4 \cdot H_2O$ | 31.25 |
| $ZnSO_4 \cdot 7H_2O$ | 0.416 |
| AMINO ACIDS | |
| L-Alanine | 11.225 |
| L-Arginine•HCl | 283.75 |
| L-Asparagine•$H_2O$ | 18.75 |
| L-Aspartic Acid | 16.325 |
| L-Cysteine•$H_2O$(non-animal) | 43.78 |
| L-Cystine•2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl•$H_2O$ | 38.69 |
| L-Isoleucine | 31.24 |
| L-Leucine | 42.5 |
| L-Lysine•HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine•$2Na_2H_2O$ (non-animal) | 35.9 |
| L-Valine | 38.1261 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine•2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| i-Inositol | 24.3 |
| Niacinamide | 1.03 |
| Pyridoxine•HCl | 1.046 |
| Riboflavin | 0.13 |
| Thiamine•HCl | 1.23 |
| Thymidine | 0.6325 |
| Vitamin $B_{12}$ | 1.04 |

2. Transfer of Cells to Low Serum Media

Transferring a culture of pancreatic cells to low serum media promotes the selection of a defined population of cells with an intermediate state of differentiation. This cell population will continue to proliferate if subcultured, but maintains high expression levels of pancreatic markers such as PDX-1. Unstimulated, this population secretes relatively low levels of pancreatic endocrine hormones such as insulin, but can be matured according to the methods of the invention to yield high-secreting cells. To transfer a culture of pancreatic cells to low serum medium, the cells may be weaned from high serum to low serum media, or may be placed directly in low serum media following isolation. Medium such as SM95 and SM98 are suitable low serum media, although SM95 yields slightly improved insulin secretion upon maturation the of pancreatic cells.

The EphA4-positive cell population and its progeny typically retains both the ability to proliferate and the ability for further differentiation into high-secreting endocrine cells. As the EphA4-positive cells proliferate, the strength of EphA4 expression can become less pronounced, and may be detectable only by RT-PCR.

The ability of EphA4 cells to proliferate provides an advantage in their ability to expand and increase the number of cells available for later maturation into glucose-secreting, insulin-producing aggregates. Proliferative ability is generally assessed by the ability of a culture seeded at a one density to expand to a second density; e.g., cells plated at 180 cells per square centimeter may be expanded to 1,800 cells per ml in a single passage. By repeated cycles of propagation and passage, a starting population of isolated pancreatic cells may be expanded by about 10,000-fold or more (e.g., about 100-fold, 500-fold, 1000-fold, 5000-fold, 10,000-fold, 50,000-fold, 100,000-fold, 500,000-fold, or 1,000,000 fold) while retaining endocrine markers such as PDX-1 and insulin mRNA expression, and retaining the ability to differentiate into mature high-secreting endocrine cells.

V. Differentiation-Induction of Insulin Producing Aggregates

Cell differentiation of EphA4-positive cells can be induced through induction of cell aggregation. As the EphA4-positive cells differentiate, the strength of EphA4 expression can become less pronounced. Cell aggregation can be induced in a variety of ways. For example, aggregation and differentiation can be induced by growing the cells to confluence. Aggregation and differentiation can also be induced by growing cells on conditioned culture dishes.

A variety of substrates can be used to condition culture dishes. Conditioned culture dishes can be culture dishes that have been used previously to grow intermediate stage pancreatic stem cells. Once the cells have formed a monolayer (typically about 5 days, depending on the initial subculture seeding density), they are removed by trypsinization. Growth of a 100% confluent cell culture is not required to produce a conditioned culture dish. A lowered concentration of trypsin (typically ½ or ¼ of the concentration employed in standard cell culture techniques) is preferred to prevent extensive degradation of the matrix. Alternatively, the cell monolayer may be removed by extracting the substrate with detergent, which will remove the cells but leave behind the secreted matrix (see Gospodarowicz et al., *Proc Natl Acad Sci USA* 77:4094-8 (1980)).

Conveniently, the removed cells which previously grew on the substrate or culture dish may be split and reseeded on the same, now conditioned, culture dish. However, the culture which conditions the substrate and the culture which is seeded on the substrate need not be the same culture. Accordingly, one culture of cells may be grown on a substrate to condition the substrate, the cells removed, and cells from another culture seeded upon the conditioned substrate. The conditioning cells may be from the same or different donor or species as the cells subsequently cultured.

In another embodiment, plates conditioned with collagen coating are used in the invention. Collagen coated plates are commercially available. In a preferred embodiment, collagen IV coated plates are used to induce aggregation and differentiation of pancreatic cells.

Differentiation of EphA4-positive cells into mature insulin producing cells can also be enhanced by growth of the cells in the presence of differentiation factors. Preferred differentiation factors include hepatocyte growth factor, keratinocyte growth factor, and exendin-4. Hepatocyte growth factor has been shown to effect differentiation of pancreatic cells in culture and in transgenic animals. See e.g., Mashima, H. et al., *Endocrinology*, 137:3969-3976 (1996); Garcia-Ocana, A. et al., *J. Biol. Chem.* 275:1226-1232 (2000); and Gahr, S. et al., *J. Mol. Endocrinol.* 28:99-110 (2002). Keratinocyte growth factor has been shown to effect differentiation of pancreatic cells in transgenic animals. See e.g., Krakowski, M. L., et al., *Am. J. Path.* 154:683-691 (1999) and Krakowski, M. L., et al., *J. Endochrinol.* 162:167-175 (1999). Exendin-4 has been shown to effect differentiation of pancreatic cells in culture. See e.g., Doyle M. E. and Egan J. M., *Recent Prog. Horm. Res.* 56:377-399 (2001) and Goke, R., et al., *J. Biol. Chem.* 268:19650-19655 (1993). bFGF has been shown to increase the insulin secretion in microencapsulated pancreatic islets. See e.g., Wang W., et al., *Cell Transplant* 10(4-5): 465-471 (2001). IGF-I has an effect on differentiation of pancreatic ductal cells and IGF-I replacement therapy has been used for type I diabetes treatment. See e.g., Smith F E., et al., *Proc. Natl. Acad. Sci. USA.* 15; 88(14): 6152-6156 (1991), Thrailkill K M. et al., *Diabetes Technol. Ther.* 2(1): 69-80 (2000). Evidence has shown that NGF plays an important autoregulatory role in pancreatic beta-cell function. See e.g. Rosenbaum T. et al., *Diabetes* 50(8): 1755-1762 (2001), Vidaltamayo R. et al., *FASEB* 16(8): 891-892 (2002), and Pierucci D. et al., *Diabetologia* 44(10): 1281-1295 (2001). EGF has been shown to promote islet growth and stimulate insulin secretion. See e.g., Chatterjee A K. et al., *Horm. Metab. Res.* 18(12): 873-874 (1986).

VI. Characterization of EphA4-Positive Cells and their Progeny

Those of skill in the art will recognize that it can be useful to determine the differentiation state of EphA4-positive cells and their progeny. The differentiation state of pancreatic cells can be determined in a variety of ways, including measurement of protein and mRNA markers of differentiation and functional assays of pancreatic cells, e.g. ability to secrete insulin in response to glucose stimulation.

A. Phenotypic Assays

To know when mature pancreatic cells are present, it is useful to assay the phenotypes of pancreatic cells at particular stages of culture. Since expression of particular proteins correlates with cell identity or differentiation state, cells may be analyzed for the expression of a marker gene or protein to assess their identity or differentiation state. For example, in freshly isolated pancreatic tissue, expression of amylase identifies the cell as an exocrine acinar cell, while expression of insulin identifies the cell as an endocrine islet cell. Likewise, islet cells at an early stage of differentiation are usually positive for the cytokeratin CK-19, while mature islet cells show less expression of CK-19.

Phenotypic properties may be assayed on a cell-by-cell basis or as a population average. The mode of assay will depend on the particular requirements and methodology of the assay technique. Thus, assays of marker expression by immunohistochemistry, performed on fixed sections or on suspended cells by FACS analysis, measure the frequency and intensity with which individual cells express a given marker. On the other hand, it may be desirable to measure properties such as the average insulin to actin mRNA expression ratio over an entire population of cells. In such cases, the assay is typically performed by collecting mRNA from a pool of cells and measuring the total abundance of insulin and actin messages. Many phenotypic properties may be assayed either on a cell or population basis. For example, insulin expression may be assayed either by staining individual cells for the presence of insulin in secretory granules, or by lysing a pool of cells and assaying for total insulin protein. Similarly, mRNA abundance may be measured over a population of cells by lysing the cells and collecting the mRNA, or on an individual cell basis by in situ hybridization.

1. Cell Differentiation Markers

There are a number of cellular markers that can be used to identify populations of pancreatic cells. Donor cells isolated and cultured begin to display various phenotypic and genotypic indicia of differentiated pancreatic cells. Examples of the phenotypic and genotypic indicia include various molecular markers present in the facultative progenitor cell population that are modulated (e.g., either up or down regulated). These molecular markers include CK-19, which is hypothesized to be a marker of the pancreatic facultative stem cell.

Typically, mammalian stem cells proceed through a number of developmental stages as they mature to their ultimate developmental endpoint. Developmental stages often can be determined by identifying markers present or absent in developing cells. Because human endocrine cells develop in a similar manner, various markers can be used to identify cells as they transition from a stem cell-like phenotype to pseudo-islet phenotype.

The expression of markers in cells induced to proliferate or differentiate by the methods of the present invention bears some similarity to the sequence of marker expression in normal human pancreas development. Very early in development, the primordial epithelial cells express PDX-1, an early cellular marker that is a homeodomain nuclear factor. As the cells develop, they begin to bud out and form a duct. These cells express cytokeratin 19, a marker for epithelial ductal cells, and temporally express PDX-1 leading developmentally to endocrine cells. As these cells continue to develop, they gain the ability to express insulin, somatostatin, or glucagon. The final differentiated cells are only able to express one and become the α cells (glucagon), β cells (insulin), and δ cells (somatostatin). The EphA4-positive cell population used herein is believed to be at a less than fully differentiated stage of development, retaining the ability to proliferate and the potential to differentiate into mature endocrine cells. Whether the cells are indeed examples of a precursor in the development pathway or simply a result of in vitro manipulation, the EphA4-positive cells are able to proliferate as well as to express endocrine hormones and, therefore, have the potential for being used to correct a deficiency in any type of islet cell.

Markers of interest are molecules that are expressed in temporal- and tissue-specific patterns in the pancreas (see Hollingsworth, *Ann N Y Acad Sci* 880:38-49 (1999)). These molecular markers are divided into three general categories: transcription factors, notch pathway markers, and intermediate filament markers. Examples of transcription factor markers include PDX-1, NeuroD, Nkx-6.1, Isl-1, Pax-6, Pax-4, Ngn-3, and HES-1. Examples of notch pathway markers include Notch1, Notch2, Notch3, Notch4, Jagged1, Jagged2, Dll1, and RBPjk. Examples of intermediate filament markers include CK19 and nestin. Examples of markers of precursors of pancreatic β cells include PDX-1, Pax-4, Ngn-3, and Hb9. Examples of markers of mature pancreatic β cells include insulin, somatostatin, glp-9, and glucagon.

Methods for assessing expression of protein and nucleic acid markers in cultured or isolated cells are standard in the art and include quantitative reverse transcription polymerase chain reaction (RT-PCR), Northern blots, and in situ hybridization (see, e.g., *Current Protocols in Molecular Biology* (Ausubel et al., eds. 2001 supplement)) and immunoassays, such as immunohistochemical analysis of sectioned material, Western blotting, and, for markers that are accessible in intact cells, flow cytometry analysis (FACS) (see, e.g., Harlow and Lane, *Using Antibodies: A Laboratory Manual*, New York: Cold Spring Harbor Laboratory Press (1998)). Conventional histochemical markers of endocrine cell differentiation may also be employed. Cells to be examined by immunohistochemistry may be cultured on glass chamber slides for microscopic examination. Alternatively, cells grown in conventional tissue culture may be manually removed from the culture and embedded in paraffin for sectioning. PDX-1 antibody can be made following the teachings of Leonard J. et al., Mol. Endocrinol., 1993, Oct. 7, (10) 1275-83.

Cell differentiation markers are varied and can be detected by conventional immunohistochemistry. A generally applicable protocol follows.

The staining process begins with removing chamber portion of the slides. Cells were very gently rinsed with in buffers and fixed in paraformaldehyde solution. Cells are then incubated in a blocking solution containing normal serum at room temperature. Cells were permeabilized with non-ionic detergent in blocking solution. Primary antibodies as listed below are prepared in blocking solution at appropriate dilution and added to cells and incubated. Following incubating with primary antibody, cells were rinsed in buffer and reblocked in blocking solution.

Secondary antibody prepared in blocking solution at appropriate dilution is added to the cells and incubated in the dark. Following incubation the cells are rinsed and nuclei were counterstained with Hoechst dye. Excess fluid is removed and the slides are mounted and covered with coverslides. The slides dry and are stored in the dark.

Alternatively the cells can be prepared for immunocytochemistry using the ABC method. In brief, the cells are embedded in parafin and slides with paraffin sections are dried at 37° C. overnight. The cells are deparaffinized and immersed in a hydrogen peroxide methanol solution to inhibit endogenous peroxidase activity. Slides were boiled in 0.01 citrate buffer (pH 6.0) for 30 minutes to recover certain epitopes. Slides were rinsed with buffer and blocked using normal serum at room temperature in a moist chamber.

Primary antibody prepared in blocking solution are added to the samples and incubated in a moist chamber. Slides are washed and incubated with secondary antibody prepared in blocking solution. Slides were again rinsed with buffer and incubated with Avidin-Horse Reddish Peroxides reagent or ABC complex from a commercial kit (e.g. Dako Corporation). Slides are again rinsed and incubated with diaminobenzidin developing solution; urea hydrogen peroxides in a gold wrap. After washes with distilled water, slides are immersed in Mayer's Hematoxylin for 5 minutes, then kept slides in running tap water until water turned colorless and nuclei were blue. Slides are dehydrated and mounted for viewing.

2. Insulin mRNA Expression

One marker that may be used to characterize pancreatic cell identity, differentiation, or maturity is the level of insulin mRNA. For example, the intermediate cell population of the present invention show expression of insulin mRNA within a defined range. Method for quantitating insulin mRNA include Northern blots, nuclease protection, and primer extension. In one embodiment, RNA is extracted from a population of cultured cells, and the amount of proinsulin message is measured by quantitative reverse transcription PCR. Following reverse transcription, insulin cDNA is specifically and quantitatively amplified from the sample using primers hybridizing to the insulin cDNA sequence, and amplification conditions under which the amount of amplified product is related to the amount of mRNA present in the sample (see, e.g., Zhou et al., *J Biol Chem* 272:25648-51 (1997)). Kinetic quantification procedures are preferred due to the accuracy with which starting mRNA levels can be determined.

Frequently, the amount of insulin mRNA is normalized to a constitutively expressed mRNA such as actin, which is specifically amplified from the same RNA sample using actin-specific primers. Thus, the level of expression of insulin mRNA may be reported as the ratio of insulin mRNA amplification products to actin mRNA amplification products, or simply the insulin:actin mRNA ratio. The expression of mRNAs encoding other pancreatic hormones (e.g., somatostatin or glucagon) may be quantitated by the same method. Insulin and actin mRNA levels can also be determined by in situ hybridization and then used to determine insulin:actin mRNA ratios. In situ hybridization methods are known to those of skill in the art.

B. Functional Assays

One of the important functions of a beta cell is to adjust its insulin secretion according to the glucose level. Typically, a static glucose stimulation (SGS) assay can be performed on the proliferating adherent pancreatic cells to identify whether they are able to secrete insulin in response to different glucose levels. Cells are generally cultured on an appropriate substrate until nearly confluent. Three days prior to the SGS test, the culture medium is replaced by a medium of similar character but lacking insulin and containing only 1 g/L of glucose. The medium is changed each day for three days and the SGS test is performed on day four.

Before the test, the culture medium may be collected for glucose and insulin analysis. To prepare cells for the test, cells are washed twice with Dulbecco's phosphate-buffered saline (DPBS)+0.5% BSA, incubating for 5 minutes with each wash, and then once with DPBS alone, also incubating for 5 minutes. After washing, the cells are incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation is then repeated.

To perform the SGS assays, cells are incubated in 3 ml (100 mm dish) or 4 ml (T75 flask) or 2 ml (60 mm dish) KRB-60, at 37° C. for 20 minutes. The medium is aspirated and spun, and is collected for insulin assay as LG-1 (low glucose stimulated step). KRB-450+theo (KRB with 450 mg/dl glucose and 10 mM theophylline) is then added with the same volume as above, and cells are cultured under the same condition as above. The supernatant is collected for insulin assay as HG (high glucose stimulated). The cells are then incubated again with KRB-60 and the medium collected as LG-2, and another time as LG-3. The media are collected for insulin analysis, and stored at −20° C. until insulin content is determined by radioimmunoassay (RIA) or other suitable assay.

The results of the SGS test are often expressed as a stimulation index, defined as the HG insulin value divided by the LG-1 insulin value. Generally, a stimulation index of about 2 or greater is considered to be a positive result in the SGS assay, although other values (e.g., 1.5, 2.5, 3.0, 3.5, etc.) may be used to define particular cell populations.

C. Preparation of EphA4-Positive Cells or their Progeny for Implantation and Restoration of Pancreatic Endocrine Function Those of skill in the art will recognize that propagating EphA4-positive cells provide a renewable resource for implantation and restoration of pancreatic function in a mammal. Propagating EphA4-positive pancreatic cells are first differentiated before implantation into the mammal. If desired by the user, EphA4 cells can be encapsulated before implantation.

D. Encapsulation

Encapsulation of the EphA4-positive cells results in the formation of cellular aggregates in the capsules. Encapsulation can allow the pancreatic cells to be transplanted into a diabetic host, while minimizing the immune response of the host animal. The porosity of the encapsulation membrane can be selected to allow secretion of biomaterials, like insulin, from the capsule, while limiting access of the host's immune system to the foreign cells.

Encapsulation methods are known in the art and are disclosed in, for example, the following references: van Schelfgaarde & de Vos, *J. Mol. Med.* 77:199-205 (1999), Uludag et al. *Adv. Drug Del Rev.* 42:29-64 (2000) and U.S. Pat. Nos. 5,762,959, 5,550,178, and 5,578,314. Encapsulation methods are also described in detail in international application PCT/US02/41616; incorporated herein by reference.

E. Implantation

Implantation or transplantation into a mammal and subsequent monitoring of endocrine function may be carried out according to methods commonly employed for islet transplantation; see, e.g., Ryan et al., *Diabetes* 50:710-19 (2001); Peck et al., *Ann Med* 33:186-92 (2001); Shapiro et al., *N Engl J Med* 343(4):230-8 (2000); Carlsson et al., *Ups J Med Sci* 105(2):107-23 (2000) and Kuhtreiber, W M, Cell Encapsulation Technology and Therapeutics, Birkhauser, Boston, 1999. Preferred sites of implantation include the peritoneal cavity, the liver, and the kidney capsule.

One of skill in the art will be able to determine an appropriate dosage of microcapsules for an intended recipient. The dosage will depend on the insulin requirements of the recipient. Insulin levels secreted by the microcapsules can be determined immunologically or by amount of biological activity. The recipients body weight can also be taken into account when determining the dosage. If necessary, more than one implantation can be performed as the recipient's response to the encapsulated cells is monitored. Thus, the response to implantation can be used as a guide for the dosage of encapsulated cells. (Ryan et al., *Diabetes* 50:710-19 (2001))

F. In vivo Measure of Pancreatic Endocrine Function

The function of encapsulated cells in a recipient can be determined by monitoring the response of the recipient to glucose. Implantation of the encapsulated cells can result in control of blood glucose levels. In addition, evidence of increased levels of pancreatic endocrine hormones, insulin, C-peptide, glucagon, and somatostatin can indicate function of the transplanted encapsulated cells.

One of skill in the art will recognize that control of blood glucose can be monitored in different ways. For example, blood glucose can be measured directly, as can body weight and insulin requirements. Oral glucose tolerance tests can also be given. Renal function can also be determined as can other metabolic parameters. (Soon-Shiong, P. et al., *PNAS USA* 90:5843-5847 (1993); Soon-Shiong, P. et al., *Lancet* 343:950-951 (1994)).

VII. Double-Selection of EphA4- and CD56- Positive Cells

In some embodiments, it is desirable to select for cells that express both EphA4 and CD56. CD56, also known as Neural Cell Adhesion Molecule (N-CAM), is a cell surface protein. International application PCT/US2003/028068, filed Sep. 8, 2003, and published as WO 2004/023100, sets forth the finding that CD56 is an extracellular marker for progenitors of pancreatic β cells, and describes in detail methods of selecting CD56-positive cells. Without repeating the entirety of WO 2004/023100, which is incorporated herein by reference, CD56-positive cells can be selected, for example, by use of CD56-specific antibodies, including antibodies that specifically binds an oligosaccharide linked to the CD56 protein, as well as by use of lectins that specifically bind to such an oligosaccharide. Antibodies to CD56 are commercially available from a variety of sources, including Sigma-Aldrich (St. Louis, Mo.), Ancell Corp. (Bayport, Minn.), Diagnostic BioSystems (Pleasanton, Calif.), and Biocare Medical (Concord, Calif.). The selection for CD56-positive cells can be made before or after the selection of EphA4-positive cells, as the practitioner finds convenient. Cells that express both EphA4 and CD56 are expected to be particularly useful in the methods and compositions of the present invention.

As can be appreciated from the disclosure provided above, the present invention has a wide variety of applications. Accordingly, the following examples are offered for illustration purposes and are not intended to be construed as a limitation on the invention in any way.

EXAMPLES

Example 1

This Example sets forth materials and methods used in studies underlying the present invention.

A. Organ Procurement

Pancreatic cells are isolated from cadaver pancreases. Organ harvesting is orchestrated by United Network for Organ Sharing ("UNOS") and local organ donor organizations. Only donors with signed consent forms for research are used.

For harvesting the pancreas, the abdominal aorta is cannulated below the junction of the renal artery, and the portal perfusion is cannulated via the inferior mesentery vein. The cannula is inserted into the portal vein (PV) to the level above the junction of the splenic vein (SV) to the PV. A loose 2-0 tie is put around the SV at the junction with the portal vein, and another loose 2-0 tie is put around the splenic artery (SA). The SV tie is ligated and cut open on the spleen side immediately before the perfusion starts. This makes the pancreas perfusion more efficient without aortic/portal double end pressure which may damage the islets. It also allows all the portal perfusant to go into the liver and avoids draining the perfusant from the spleen and pancreas into the liver. The lesser sac is opened and a normal saline ("NS") slush is applied over the pancreas. After 1 L of aorta perfusion, the SA is ligated. The pancreas should be well protected when the liver and kidneys are harvested. The pancreas is retrieved with the procedures known and used in the art for pancreas transplants.

The organ is stored in a plastic bag filled with UW solution (University of Wisconsin solution, known as "UW solution", or "Belzer UW" is a cold storage solution for organ preservation. See, e.g., Uhlmann et al., J Surg Res. 105(2):173-80 (2002), Southard et al., Transplantation. 49(2):251-7 (1990), Fridell et al., Transplantation. 77(8):1304-1306 (2004), Inui et al., Pancreas. 23(4):382-386 (2001), and Matsumoto et al., Transplant Proc. 36(4):1037-9 (2004). The formula is available on the internet by entering "http://www." followed by "surgery.wisc.edu/transplant/research/southard/UWFormula". Belzer UW solution is commercially available under the name ViaSpan® (Barr Laboratories, Inc., Pomona, N.Y.))

and set in a Nalgene® jar with sterile NS slush, or directly stored in a Nalgene® jar soaked in between $O_2$-saturated-perfluorocarbon (PFC) and UW solutions for transportation (placing pancreatic tissue between UW solution and a perfluorocarbon is known as the two-layer system and is taught in, e.g., Matsumoto et al., supra, Deai et al., Kobe J Med Sci 45:191-19-9 (1999), Hering et al., Transplantation 74: 1813-1816 (2002), Ricordi et al., Transplantation 75: 1524-1527 (2003), and Lakey et al., Transplantation 74: 1809-1811 (2002). See generally, Shapiro, J Am Soc Nephrol 14:2214-2216 (2003)).

B. Pancreas Digestion

The islets are isolated by enzymatic pancreas digestion. One vial of Liberase (0.5 g, Roche) is dissolved in 333 ml of HBSS (1.5 mg/ml, 37° C.) and infused into the pancreas via ductal cannulation(s). The organ is incubated in an 800 ml tempering beaker at 37° C. for 10-20 minutes until the tissue becomes soft.

The semi-digested tissue mass is transferred into the metal digestion chamber and automatic circulating digestion started. Tissue is dissociated by agitation of the digestion chamber.

When the majority of islets have been released from the surrounding tissue, the digestant is collected and diluted with Medium A10 (10% fetal bovine serum in RPMI). The digestion procedure takes about 30 minutes. The cells are washed with A10 three times at 4° C., 1,000 rpm, 2 minutes, and then go through the cell separation procedure.

C. Pancreatic Cell Separation

The pellet resulting from the washing and centrifugation procedure described in the preceding paragraph is mixed with 320 ml Pancreatic Islet Purification Solution ("PIPS") (a 13.7% solution of Nycodenz® AG (Axis-Shield PoC AS, Oslo, Norway; Nycodenz® is a centrifuge density gradient solution with the systemic name 5-(N-2,3-dihyroxypropylac-etamide)-2,4,6-tri-iodo-N,N'-bis(2,3 dihydroxypropyl) isophtalamide) prepared in ViaSpan® Belzer UW solution (density 1.114) and set on ice for 10 minutes.

Each of eight 250 ml flat-bottom centrifuge tubes are filled with 70 ml PIPS (density 1.090). Forty ml of cell/PIPS suspension is then under-laid into each tube. Sixty ml of RPMI 1640 with 2% FBS is over-laid on top of the PIPS. The tubes are centrifuged for six minutes without braking, using a Sorvall RC-3C Plus with a 05, ARC rotor at 1,500 rpm.

The upper interface (A layer, purified islets), lower interface (B layer, mixture of entrapped islets, fragmental islets, acinar and ductal cells) and the pellet (mainly acinar and ductal cells) are collected separately. The cells are washed two more times with Medium A10 and then used as desired.

D. Antibody and Cocktail Assembly

EphA4 murine IgG monoclonal antibody is purchased from BD Biosciences (Catalog # s41820-050). Antibody cocktails are prepared according to the protocol from StemCell Technologies, Vancouver, Canada. 15 µg of EphA4 murine IgG 1 monoclonal antibody dissolved in 500 sterile phosphate buffered saline (PBS) containing 2% FBS (fetal bovine serum) is added to a 1.5 mL polypropylene tube. 100 µL of component A (StemCell Technologies) and 100 µL of component B (StemCell Technologies) are sequentially added to the vial. The vial is placed into a 37° C. incubator overnight. The vial is brought to a final volume of 1.0 ml by adding sterile PBS.

E. Cell Selection Procedure

This procedure is used for processing up to $2.5 \times 10^8$ cells per separation. Nucleated cell suspensions are prepared at a concentration of $1 \times 10^8$ nucleated cells/ml in PBS containing 2% FBS. Conveniently, the cells are separated using the EasySep™ system (StemCell Technologies, Inc., Vancouver, BC, Canada). For use in the EasySep™ system, the cells are placed in 12×75 mm polystyrene tubes (Falcon® 5 mL Polystyrene Round-Bottom Tubes, Becton Dickinson, Catalogue #2058). The EasySep™ system is an immunomagnetic cell selection procedure that uses specific antibodies and tiny FACS-compatible magnetic nanoparticles in a column-free magnetic system. The assembled positive selection cocktail is added to the cell suspension at 100 µl/ml cells. The cells are mixed well and incubated at room temperature for 15 minutes. EasySep™ Magnetic Nanoparticles (StemCell Technologies) are mixed gently to ensure that they are in a uniform suspension by pipetting up and down more than 5 times (vortexing is not recommended). The nanoparticles are added to the cells at the ratio of 50 µL/mL cells. The cells are mixed well and incubated at room temperature for 10 minutes. Cell suspension is brought to a total volume of 2.5 mL by adding PBS containing 2% FBS. The cells are mixed in the tube by gently pipetting up and down 3-4 times. The cells are placed into the magnet and set aside for 5 minutes. In one continuous motion, the magnet and tube are inverted, and the supernatant fraction is poured off. The magnetically labeled cells remain inside the tube, held by the magnetic field of the EasySep™ magnet. The magnet and tube are left inverted for 2-3 seconds then returned to an upright position. The tube is removed from the magnet and 2.5 mL of recommended medium are added. The cell suspension is mixed by gently pipetting it up and down 2-3 times. The tube is placed back in the magnet and set aside for five minutes. This procedure is repeated for a total of three 5-minute separations in the magnet. The tube is removed from the magnet and the cells are resuspended in an appropriate amount of a chosen medium. The positively selected cells are now ready for use.

Example 2

A. Eph Sorting Enhances Pancreatic Phenotype of Cultured Pancreatic Cells

1. Cell Culture and Cell Selection

The procedures of Eph sorting and cell culture are shown in FIG. 1. Human pancreatic HD469B (P0) cells were seeded in 10 cm plates in SM95/M7(4:1) medium and cultured for 6 days at 37° C. Medium was changed every 2 days. On day 6, the HD469B cells were trypsinized and washed with PBS. The cells were sorted with Eph antibody coated with Magnetic Nanoparticles (StemCell Technologies) prepared as described in Example 1. The sorted Eph positive cells (P1) (about 5% of original cell population) and the Eph negative cells were cultured in SM95/M7 for 3 days. At P2, The Eph sorted cells were cultured in SM95/M7(4:1) with 20 µg/ml Wnt3a proteins for 5 days. On day 5, cells were trypsinized and washed with PBS. Small portions of both Eph positive and negative cells were harvested for RNA isolation for gene expression analysis by real-time PCR. This procedure was performed at each cell passage from P2-P5. The majority of Eph-sorted cells were passed into P3 and cultured for three days in SM95/M7(4:1) with 20 µg/ml Wnt3a proteins. On passage 4 and 5, each of the four group cells were divided into 3 plates with different coating conditions: regular (control), fibronectin and extra cellular matrix (ECM) coated plates. All cells were cultured in SM95/M7(9:1) for 3 day for each passage. At passage 6, cells were cultured in MM1 and MM2 medium for 3 days, respectively. After culture in MM2, cells were collected for isolation of total RNA.

2. Expression of EphA-4 in Adult Pancreas and Primary Pancreatic Cell Cultures

Figure 2A:
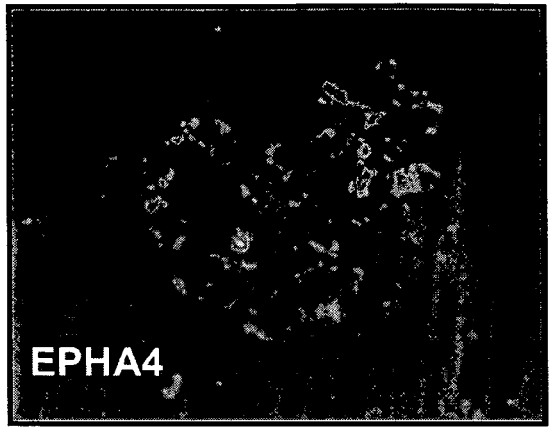
FIGS. 2a-d show immunofluorescence ("IF") and ICC studies of expression of EphA4 in adult pancreas and primary pancreatic culture.
Figure 2B:
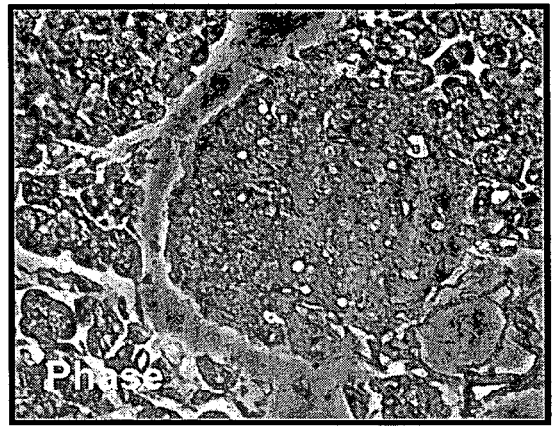
Figure 2C:
Figure 2D:
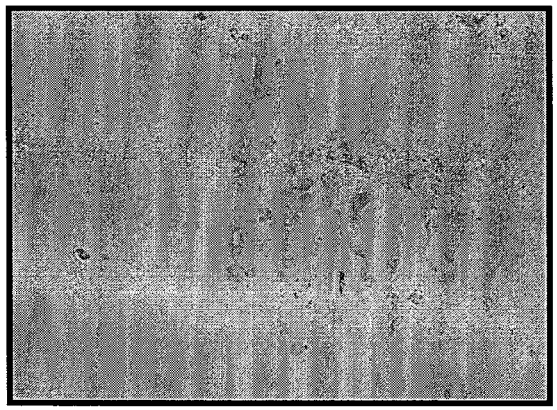

EphA4 plays important role of sorting and cell specification during development of adult tissues. To identify the expression of EphA4 in adult pancreas and cell culture, immunofluorenscence and ICC studies of adult pancreas and primary pancreatic cells were performed. As shown in FIG. 2A, EphA4 positive cells were restricted to some of islet cells and no positive staining was found in acinar cells. Expression of EphA4 was also found in a subgroup of cultured pancreatic cells (FIG. 2C).

3. Comparison of Expression of Insulin in the EphA4+ and EphA4− Cells

Figure 3:
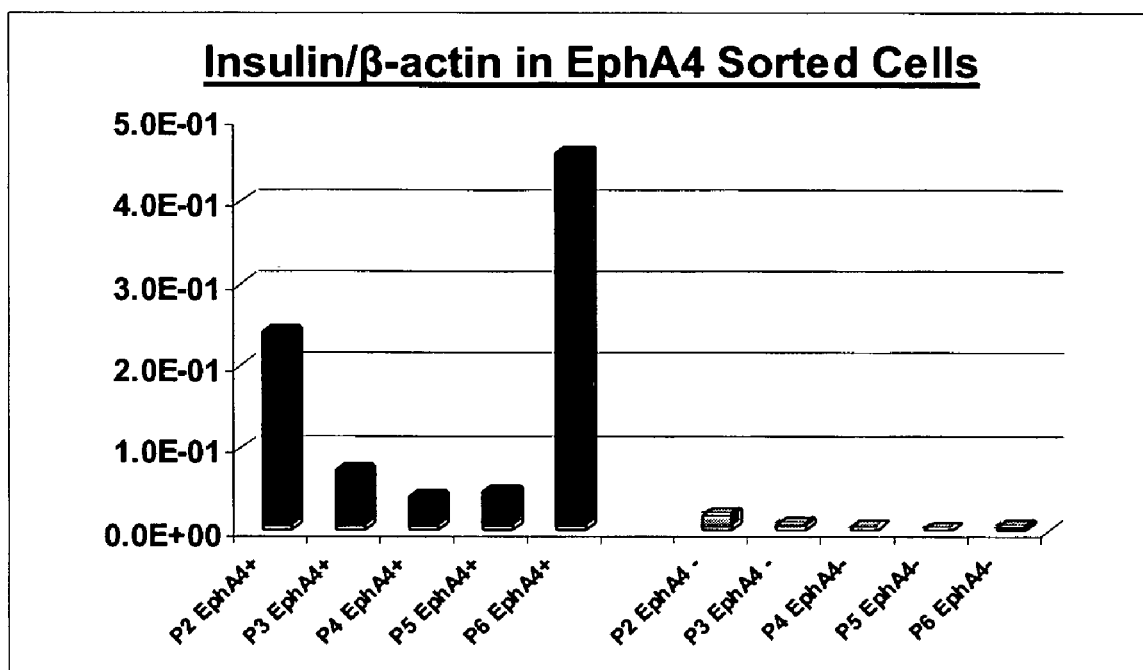
FIG. 3 shows a comparison of expression of insulin in EphA4+ and in EphA4– cells (in this Figure and in the others below that show expression levels, the expression levels are shown as a ratio of expression of the expression of the gene under discussion compared to the expression of beta-actin, a well known "housekeeping gene" often used in the art as a base for comparison of relative expression levels). Expression of insulin in EphA4-sorted cells was evaluated by real-time PCR. The mRNA levels of insulin in EphA4+ cells were 9-112 times higher than those of EphA4– cells.

Expression of insulin in EphA4 sorted cells was evaluated by real-time PCR. The mRNA levels of insulin in EphA4 positive cells were 9~112 times higher than the EphA4 negative cells (FIGS. 3 a and b). The high expression of insulin maintained the EphA4 positive cells through sequential (P2-P6) (FIG. 3, Table 1). Since EphA4-positive cells only represent about 5% of the original cell population, β-cell lineage cells were greatly enriched by EphA4 sorting.

TABLE 1

Expression of Insulin in EphA4 Positive and Negative Sorted Cells at Different Cell Passages

| HD469B | Insulin copy# | β-actin Copy# | Insulin/ β-actin ratio | Insulin expression ratio (EphA4+/ EphA4−) |
|---|---|---|---|---|
| P2 EphA4+ | 6,046,000 | 25,190,000 | 2.400E−01 | 14 |
| P2 EphA4− | 184,500 | 11,030,000 | 1.673E−02 | 1 |
| P3 EphA4+ | 425,800 | 6,108,000 | 6.971E−02 | 9 |
| P3 EphA4− | 26,180 | 3,523,000 | 7.431E−03 | 1 |
| P4 EphA4+ | 569,000 | 14,390,000 | 3.954E−02 | 22 |
| P4 EphA4− | 21,970 | 11,940,000 | 1.840E−03 | 1 |
| P5 EphA4+ | 16,200 | 373,400 | 4.339E−02 | 46 |
| P5 EphA4− | 1,025 | 1,089,000 | 9.412E−04 | 1 |
| P6 EphA4+ | 93,840 | 204,800 | 4.582E−01 | 112 |
| P6 EphA4− | 1,847 | 449,900 | 4.105E−03 | 1 |

4. Comparison of PDX-1 mRNA expression in the EphA4+ and EphA4− cells

Figure 4:
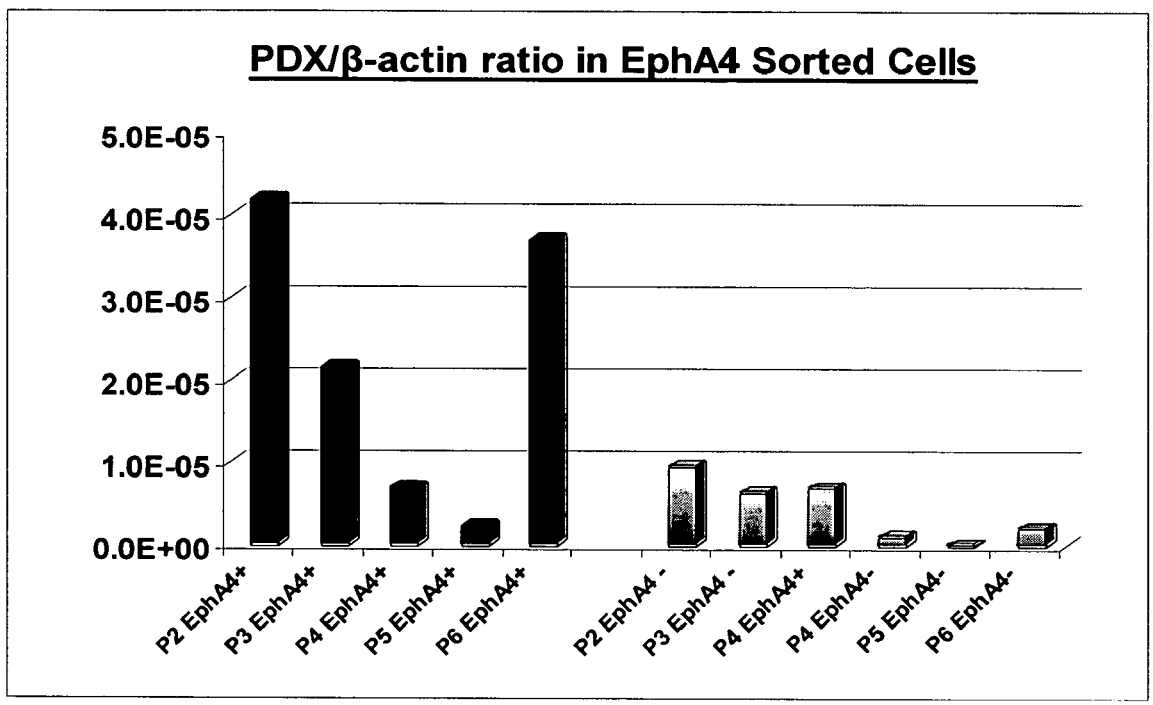
FIG. 4 shows a comparison of expression of PDX-1 in EphA4+ and in EphA4– cells. Expression of PDX-1 in sorted cells was evaluated by real-time PCR. EphA4+ cells showed 6-10 times higher mRNA levels of PDX-1 than did EphA4– cells either just after sorting (P2) or during the following passages (P3-P6). PDX-1 was expressed at a high level at early passage P2. The expression of PDX-1 gradually decreased as the number of cell passages increased. After culturing in differentiation media, the expression of PDX-1 returned to high levels in EphA4+ cells.

We compared the expression of PDX-1 in both EphA4 positive- and EphA4 negative-cells during different cell passages by real-time PCR. As shown in FIG. 4 and Table 2, EphA4 positive cells have 6~10 times higher mRNA level of PDX-1 than EphA4 negative cells either at just after sorting (P2) or during the following passages (P3-P6). PDX-1 is expressed at high level at early passage (P2). The expression of PDX-1 was gradually decreased as increased number of cell passages (P3-P5). After culturing in differentiation media, the expression of PDX-1 returned to high level in EphA4 positive cells. These data show that EphA4 can enhance pancreatic phenotype of pancreatic cells.

TABLE 2

Expression of PDX-1 in EphA4 Positive- and Negative- Sorted Cells during Different Cell Passages

| HD469B | β-actin | PDX-1 | PDX-1 expression ratio (EphA4+/EphA4−) |
|---|---|---|---|
| P2 EphA4+ | 25,190,000 | 1054 | 10 |
| P2 EphA4− | 11,030,000 | 105 | 1 |
| P3 EphA4+ | 6,108,000 | 131 | 6 |
| P3 EphA4− | 3,523,000 | 22 | 1 |
| P4 EphA4+ | 14,390,000 | 101 | 7 |
| P4 EphA4− | 11,940,000 | 14 | 1 |
| P5 EphA4+ | 373,400 | 1 | infinity |
| P5 EphA4− | 1,089,000 | 0 | 1 |
| P6 EphA4+ | 204,800 | 8 | 8 |
| P6 EphA4− | 449,900 | 1 | 1 |

5. Comparison of Expression of Nkx2.2 and Pax6 in the EphA4+ and EphA4− Cells

Figure 5:
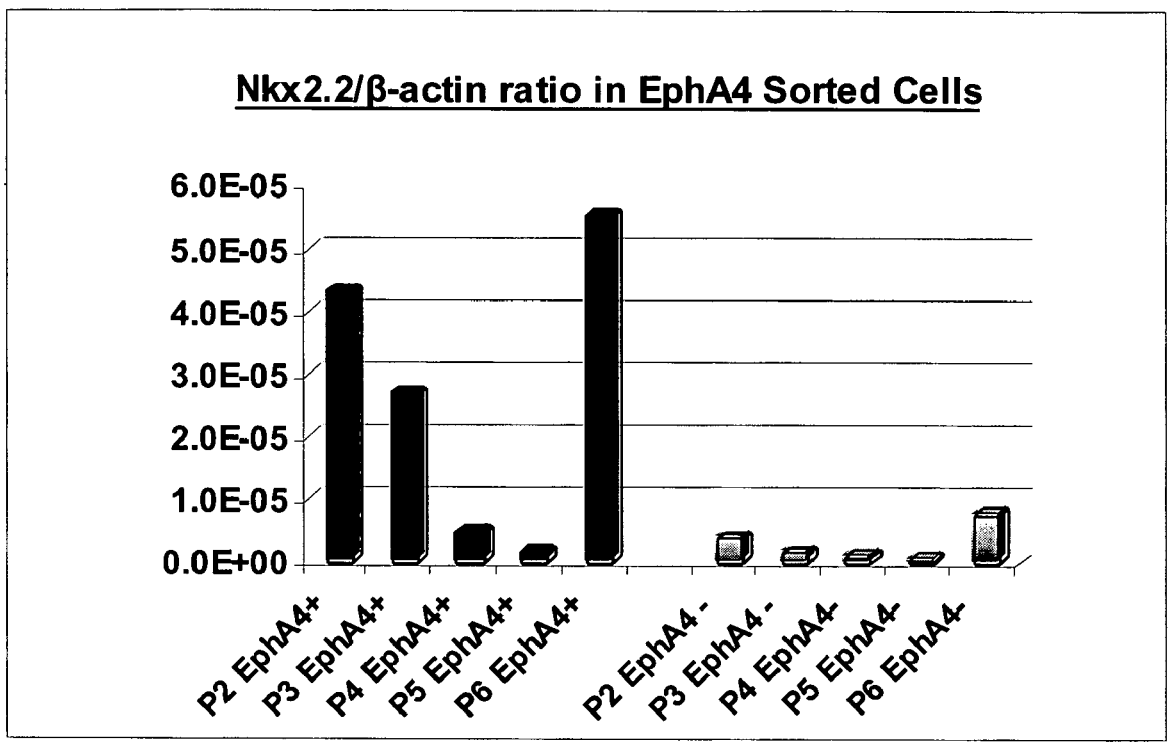
FIG. 5 shows a comparison of expression of the pancreatic progenitor marker Nkx2.2 (a homeodomain transcription factor expressed in early stages of pancreatic development) in EphA4+ and in EphA4– cells. Expression of Nkx2.2 in EphA4-sorted cells was evaluated by real-time PCR. EphA4+ cells showed 2.5-16 times higher mRNA levels of Nkx2.2 than did EphA4– cells at different cell passages.
Figure 6:
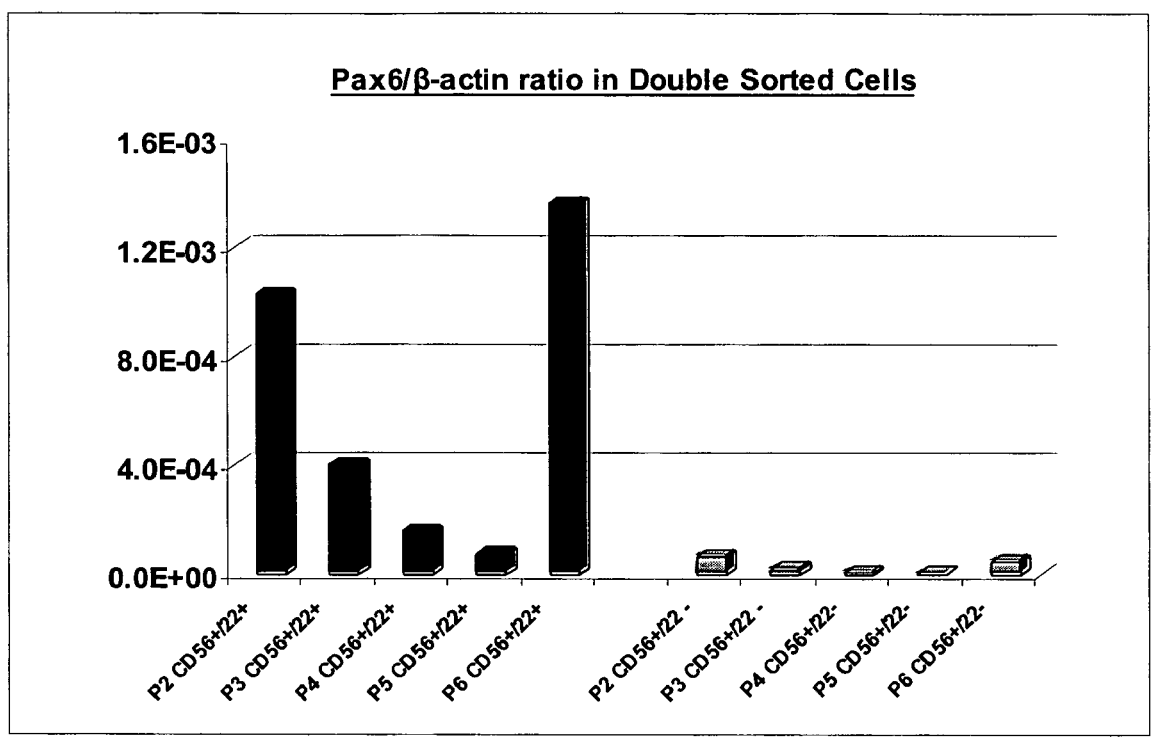
FIG. 6 shows a comparison of expression of the pancreatic progenitor marker Pax6 (a pancreatic progenitor marker that is a late factor after neurogenin3 expression that is critical to development of the differentiated islet cell phenotype) in doubly sorted cells. Expression of Pax6 in the sorted cells was evaluated by real-time PCR. Doubly sorted cells showed 8.5-64 times higher mRNA levels of Pax6 than did singly sorted cells at different cell passages.

Two pancreatic progenitor markers, Nkx2.2 and Pax6, were used to evaluate our pancreatic culture cells. Expression of Nkx2.2 and Pax6 in both EphA4 positive and negative cells was quantified by real-time PCR. The expression of Nkx2.2 in EphA4 positive cells was 2.5~16 times higher than EphA4 negative cells at different cell passages (FIG. 5 Table 3). As expected, expression of Pax6 in the EphA4 positive and negative sorted cells has a very similar pattern to and tendency as the expression of Nkx2.2. EphA4 positive cells have 8.5~64 times higher expression of Pax6 than EphA4 negative sorted cells during all the passages (FIG. 6, Table 3). These results show that the EphA4-selected cells can greatly enrich the progenitor cells of a pancreatic cell culture.

TABLE 3

Expression of NKx2.2 in EphA4 -Positive and -Negative Sorted Cells at Different Cell Passages

| HD469B | β-actin | Nkx2.2 | Nkx2.2/β-actin ratio | Nkx2.2 expression ratio (EphA4+/ EphA4−) | Pax6 | Pax6/β-actin ratio | Pax6 expression ratio (EphA4+/ EphA4−) |
|---|---|---|---|---|---|---|---|
| P2 EphA4+ | 25,190,000 | 1087 | 4.315E−05 | 11 | 10960 | 4.351E−04 | 11 |
| P2 EphA4− | 11,030,000 | 42 | 3.770E−06 | 1 | 445 | 4.037E−05 | 1 |
| P3 EphA4+ | 6,108,000 | 164 | 2.687E−05 | 16 | 1180 | 1.932E−04 | 9 |
| P3 EphA4− | 3,523,000 | 6 | 1.672E−06 | 1 | 80 | 2.262E−05 | 1 |
| P4 EphA4+ | 14,390,000 | 66 | 4.577E−06 | 5 | 1066 | 7.408E−05 | 13 |
| P4 EphA4− | 11,940,000 | 11 | 9.062E−07 | 1 | 66 | 5.562E−06 | 1 |
| P5 EphA4+ | 373,400 | 1 | 1.379E−06 | 2.5 | 9 | 2.464E−05 | 10 |
| P5 EphA4− | 1,089,000 | 1 | 5.481E−07 | 1 | 3 | 2.583E−06 | 1 |
| P6 EphA4+ | 204,800 | 11 | 5.498E−05 | 7 | 197 | 9.624E−04 | 64 |
| P6 EphA4− | 449,900 | 3 | 7.619E−06 | 1 | 7 | 1.528E−05 | 1 |

Example 3

CD56/EphA4 Double Selection Further Promotes Pancreatic Phenotype of Cultured Pancreatic Cells

A. CD56 Sorting

1. Cell Culture and Cell Selection

Figure 7:
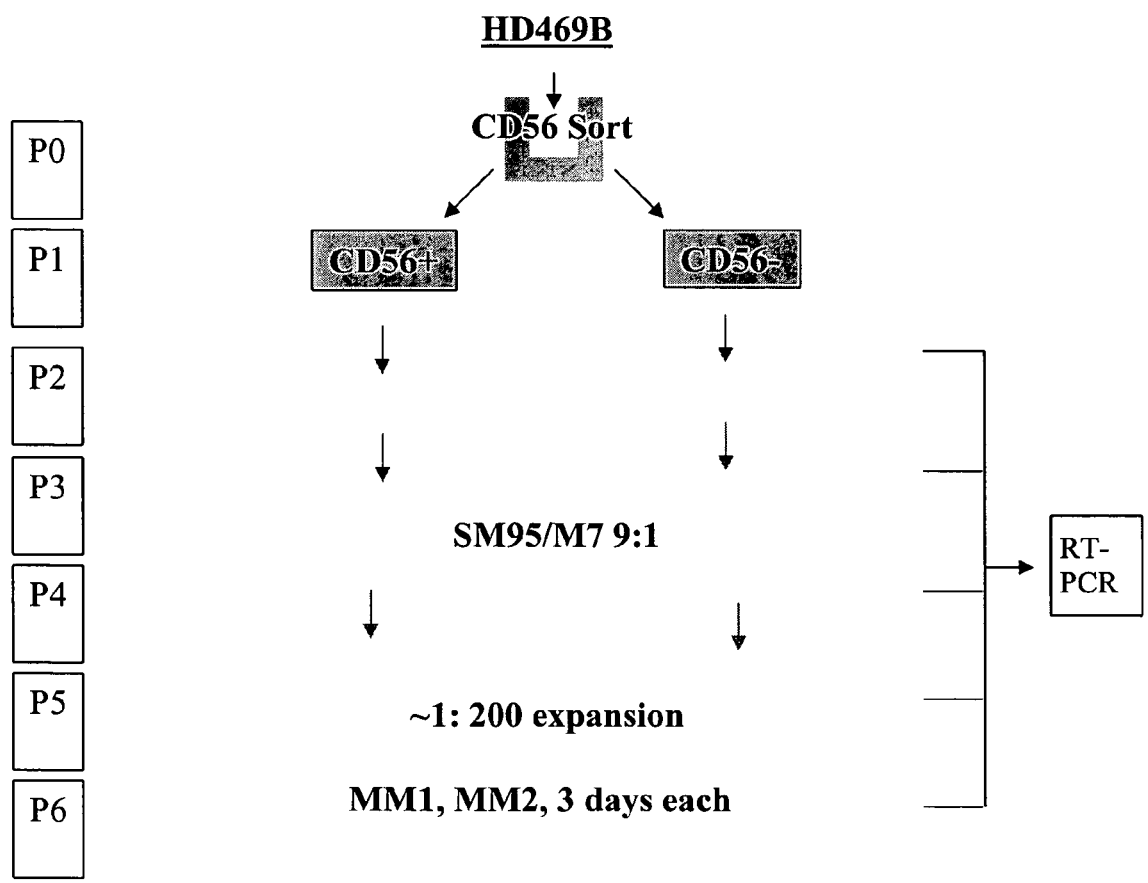
FIG. 7 shows a flow chart for CD56 cell sorting and culturing. The presence of a cell marker on the sorted cells is indicated by a positive sign ("+"), its absence is indicated by a negative sign ("–").

The procedures of CD56 sorting and cell culture are shown in FIG. 7. Human pancreatic HD469B (P0) cells were seeded in 10 cm plates in SM95/M7(4:1) medium and culture for 6 days at 37° C. Medium was changed every 2 days. On day 6, the HD469B cells were trypsinized and washed with PBS. The cells were sorted with anti-CD56 antibody coated with Magnetic Nanoparticles (StemCell Technologies) prepared as described in Example 1. The sorted CD56-positive cells (P1) (about 5% of original cell population) and the CD56-negative cells were cultured in SM95/M7 for 3 days. At P2, the CD56 sorted cells were cultured in SM95/M7(4:1) with 20 µg/ml Wnt3a proteins for 5 days. On day 5, cells were trypsinized and washed with PBS. Small portions of the cells from both CD56 positive and negative cells were harvested for RNA isolation for gene expression analysis by real-time PCR. This procedure was performed at each cell passage from P2-P5. The majority of CD56 sorted cells were passed into P3 and cultured for three days in SM95/M7(4:1) with 20 µg/ml Wnt3a proteins. On passage 4 and 5, each of the four group cells was divided into 3 plates with different coating conditions: regular (control), fibronectin and extra cellular matrix (ECM) coated plates. All cells were cultured in SM95/M7(9:1) for 3 day for each passage. At passage 6, cells were culture in MM1 and MM2 medium for 3 days, respectively. After culture in MM2, cells were collected for isolation of total RNA.

2. Comparison of Insulin Expression in the CD56+ and CD56- cells

Figure 8:
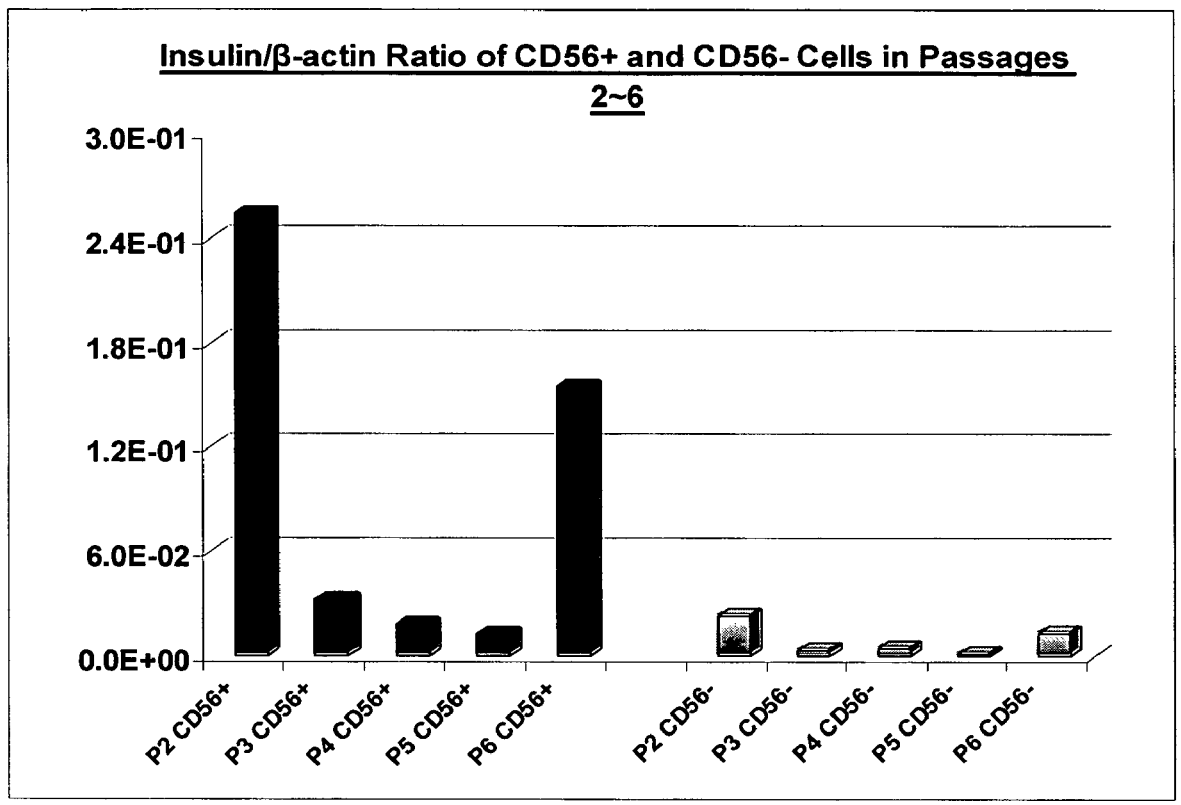
FIG. 8 shows the expression of insulin in CD56-sorted cells. Expression of insulin in CD56-sorted cells was evaluated by real-time PCR. The mRNA levels of insulin in CD56+ cells were 4-12 times higher than those of CD56– cells. Presence of a cell marker on the sorted cells is indicated by a positive sign ("+"), its absence is indicated by a negative sign ("–").

Expression of insulin in CD56 sorted cells was evaluated by real-time PCR. The mRNA levels of insulin in CD56 positive cells were 4~12 times higher than in CD56 negative cells (FIG. 8, Table 4). The high expression of insulin maintained the CD56 positive cells through sequential (P2-P6) (FIG. 13). Since CD56 positive cells represent only about 5% of the original cell population, β-cell lineage cells were greatly enriched by CD56 sorting.

TABLE 4

Expression of Insulin in CD56 Positive and Negative Cells at Different Cell Passages

| HD469B | Insulin | β-actin | Ins/β-actin ratio | Insulin expression ratio (EphA4+/EphA4−) |
|---|---|---|---|---|
| P2 CD56+ | 550,200 | 2,162,000 | 2.545E−01 | 11 |
| P2 CD56− | 256,100 | 11,050,000 | 2.318E−02 | 1 |
| P3 CD56+ | 494,500 | 15,610,000 | 3.168E−02 | 11 |
| P3 CD56− | 14,070 | 4,916,000 | 2.862E−03 | 1 |
| P4 CD56+ | 232,400 | 13,360,000 | 1.740E−02 | 4 |
| P4 CD56− | 51,500 | 13,200,000 | 3.902E−03 | 1 |
| P5 CD56+ | 13,750 | 1,176,000 | 1.169E−02 | 10 |
| P5 CD56− | 1,608 | 1,408,000 | 1.142E−03 | 1 |
| P6 CD56+ | 37,080 | 239,800 | 1.546E−01 | 12 |
| P6 CD56− | 4,849 | 380,200 | 1.275E−02 | 1 |

3. Comparison of PDX-1 Expression in the CD56+ and CD56- cells

Figure 9:
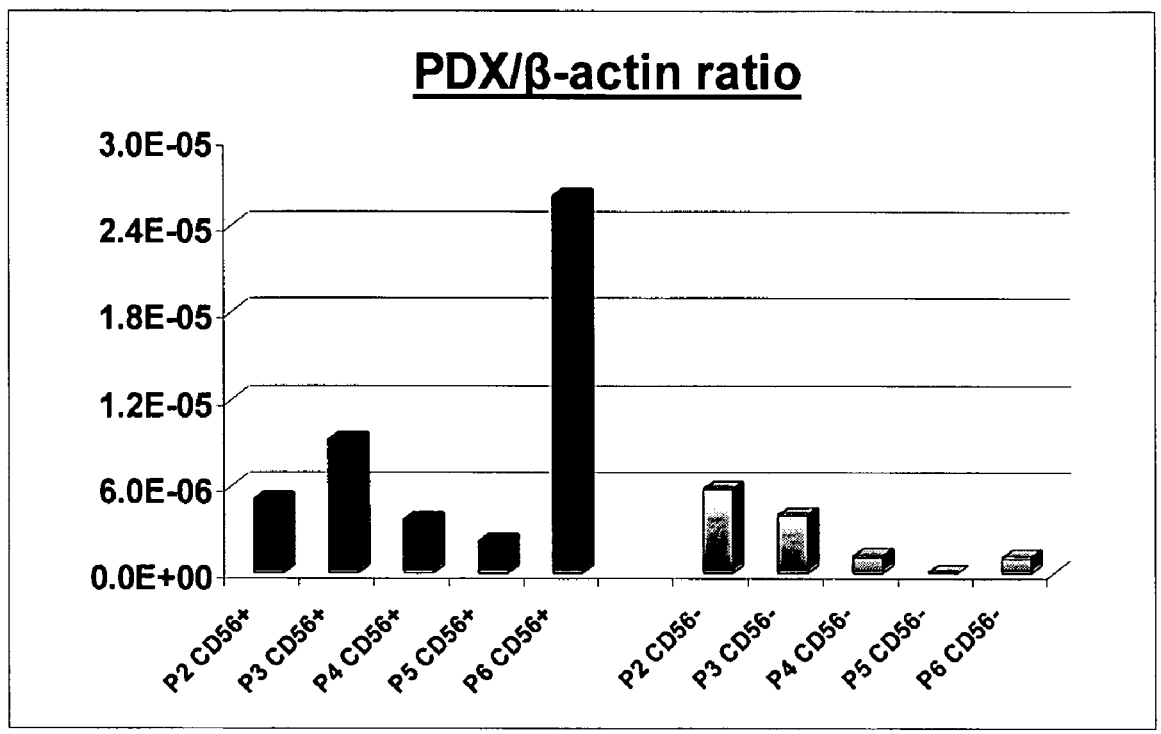
FIG. 9 shows a comparison of expression of PDX-1 in CD56+ and in CD56– cells. Expression of PDX-1 in CD56-sorted cells was evaluated by real-time PCR. CD56+ and CD56– cells showed equal expression of PDX-1 at P2, but the expression of PDX-1 gradually elevated as the number of cell passages (P3-P5) increased and reached 26 times higher than CD56– cells at P6. Presence of a cell marker on the sorted cells is indicated by a positive sign ("+"), its absence is indicated by a negative sign ("–").

We compared the expression of PDX-1 in both CD56 positive and CD56 negative cells during the cell different cell passages by real-time PCR. As shown in FIG. 9 and Table 5, CD56 positive cells have significantly higher mRNA level of PDX-1 than CD56 negative cells especially during the later passages (P3-P6). The PDX-1 expressions in the CD+ and CD− cells were at same level at P2 but PDX-1 expression in the CD+ cells were gradually elevated as increased number of cell passages (P3-P5) and reached 26 times higher then CD− cells at P6 (Table 5). After culturing in differential medium, the expression of PDX-1 returned to high level in CD56 positive cells.

TABLE 5

Expression of PDX-1 in CD56 -Positive and -Negative Sorted Cells during Different Cell Passages

| HD469B | β-actin | PDX-1 | PDX/β-actin ratio | PDX-1 expression ratio (EphA4+/EphA4−) |
|---|---|---|---|---|
| P2 CD56+ | 2,162,000 | 11 | 4.977E−06 | 1 |
| P2 CD56− | 11,050,000 | 64 | 5.750E−06 | 1 |
| P3 CD56+ | 15,610,000 | 143 | 9.167E−06 | 2 |
| P3 CD56− | 4,916,000 | 20 | 3.975E−06 | 1 |
| P4 CD56+ | 13,360,000 | 49 | 3.641E−06 | 3 |
| P4 CD56− | 13,200,000 | 15 | 1.123E−06 | 1 |
| P5 CD56+ | 1,176,000 | 3 | 2.173E−06 | infinity |
| P5 CD56− | 1,408,000 | 0 | 0.000E+00 | 1 |
| P6 CD56+ | 239,800 | 6 | 2.604E−05 | 26 |
| P6 CD56− | 380,200 | 0 | 1.021E−06 | 1 |

4. Comparison of Nkx2.2 and Pax6 Expression in the CD56+ and CD− Cells

Figure 10:
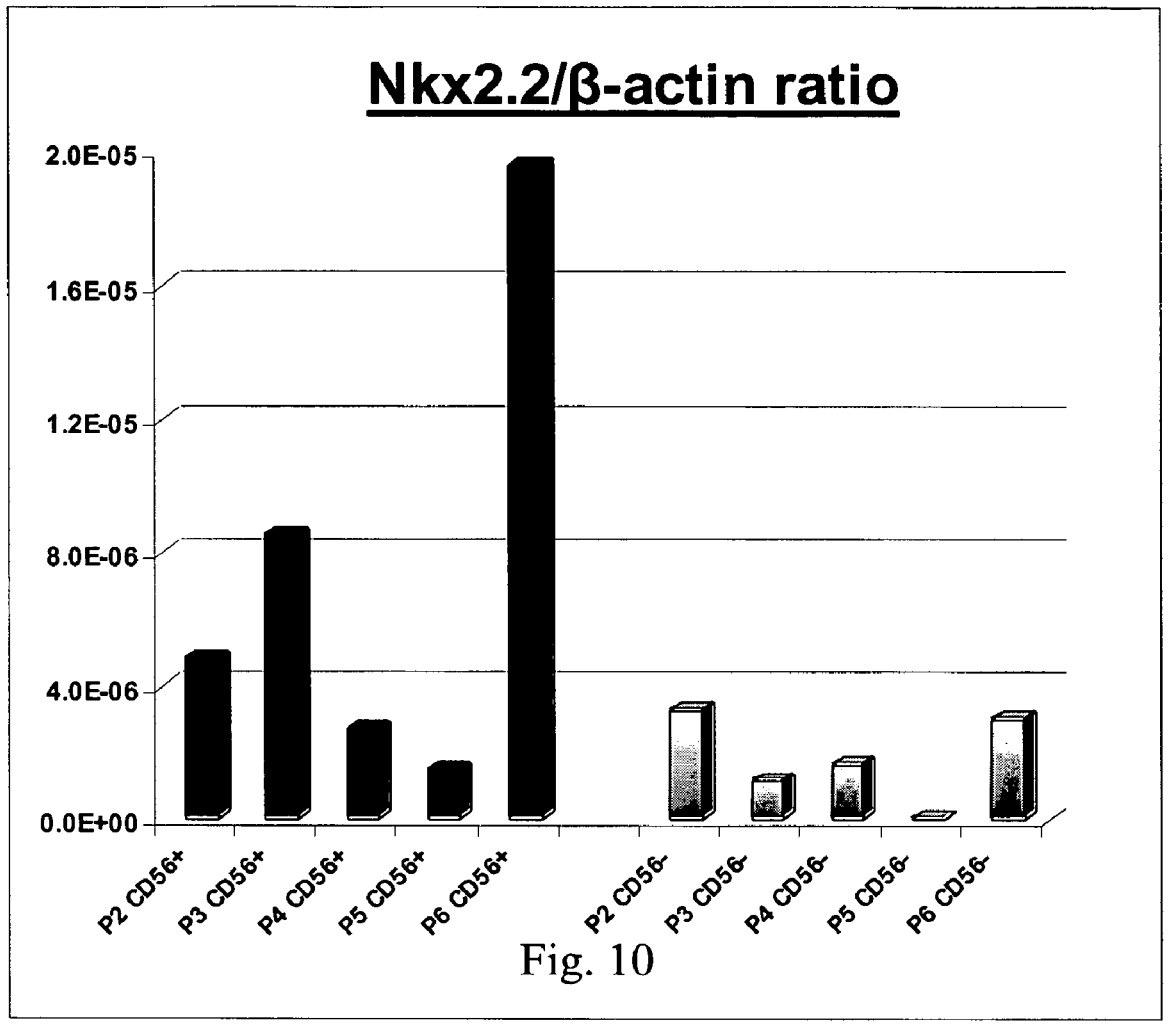
FIG. 10 shows a comparison of expression of the pancreatic progenitor marker Nkx2.2 in CD56+ and in CD56– cells. Expression of Nkx2.2 in CD56-sorted cells was evaluated by real-time PCR. CD56+ cells showed 1.6-7 times higher mRNA levels of Nkx2.2 than did CD56– cells at different cell passages. Presence of a cell marker on the sorted cells is indicated by a positive sign ("+"), its absence is indicated by a negative sign ("–").
Figure 11:
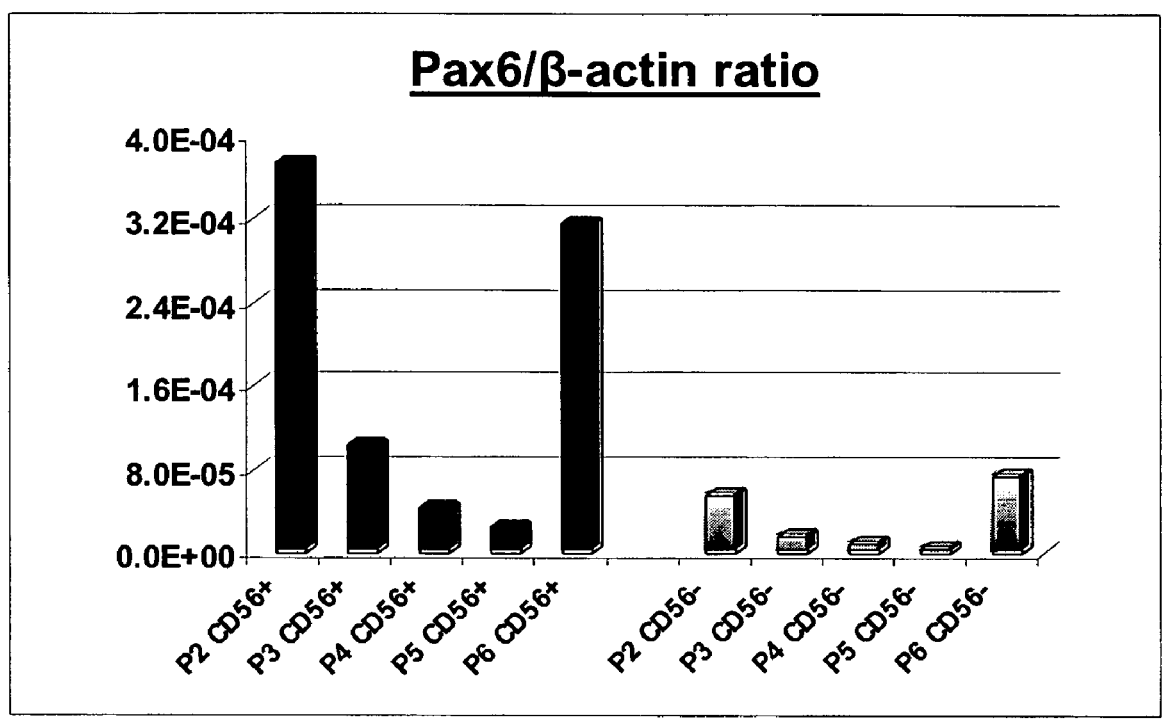
FIG. 11 shows a comparison of expression of the pancreatic progenitor marker Pax6 in CD56+ and in CD56– cells. Expression of Pax6 in CD56-sorted cells was evaluated by real-time PCR. CD56+ cells showed 4-7 times higher mRNA levels of Pax6 than did CD56– cells at different cell passages. The presence of a cell marker on the sorted cells is indicated by a positive sign ("+"), its absence is indicated by a negative sign ("–").

Two pancreatic progenitor markers, Nkx2.2 and Pax6, were used to evaluate CD56 sorted cell cultures. Expression of Nkx2.2 and Pax6 in both CD56 positive and negative cells were quantified by real-time PCR. The expression of Nkx2.2 in CD56 positive cells was 1.6~7 times higher than CD56 negative cells at different cell passages (FIG. 10, Table 6). Interestingly, expression of Pax6 in the CD56 positive and negative sorted cells has a very similar pattern and tendency as does the expression of Nkx2.2. CD56 positive cells showed 4~7 times higher Pax6 expression than CD56 negative cells during the passages (FIG. 11, Table 6). Thus, selection for CD56 positive cells can greatly enrich the progenitor cells of a pancreatic cell culture.

TABLE 6

Expression of Nkx2.2 and Pax6 in CD56 Positive and Negative Sorted Cells during Different Cell Passages

| HD469B | β-actin | Nkx2.2 | Nkx2.2/β-actin ratio | Nkx2.2 expression ratio (EphA4+/EphA4−) | Pax6 | Pax6/β-actin ratio | Pax6 expression ratio (EphA4+/EphA4−) |
|---|---|---|---|---|---|---|---|
| P2 CD56+ | 2,162,000 | 10 | 4.820E−06 | 1.5 | 808 | 3.735E−04 | 7 |
| P2 CD56− | 11,050,000 | 36 | 3.271E−06 | 1 | 608 | 5.502E−05 | 1 |
| P3 CD56+ | 15,610,000 | 133 | 8.533E−06 | 7 | 1581 | 1.013E−04 | 7 |
| P3 CD56− | 4,916,000 | 6 | 1.162E−06 | 1 | 73 | 1.491E−05 | 1 |
| P4 CD56+ | 13,360,000 | 36 | 2.703E−06 | 1.6 | 544 | 4.070E−05 | 4 |
| P4 CD56− | 13,200,000 | 22 | 1.644E−06 | 1 | 121 | 9.144E−06 | 1 |
| P5 CD56+ | 1,176,000 | 2 | 1.481E−06 | infinity | 28 | 2.371E−05 | 6 |
| P5 CD56− | 1,408,000 | 0 | 0.000E+00 | 1 | 6 | 3.960E−06 | 1 |
| P6 CD56+ | 239,800 | 5 | 1.958E−05 | 6.5 | 75 | 3.146E−04 | 4 |
| P6 CD56− | 380,200 | 1 | 3.019E−06 | 1 | 28 | 7.412E−05 | 1 |

B. Secondary Sorting with EPHA4 Antibody

1. Cell Culture and Cell Selection

Figure 12:
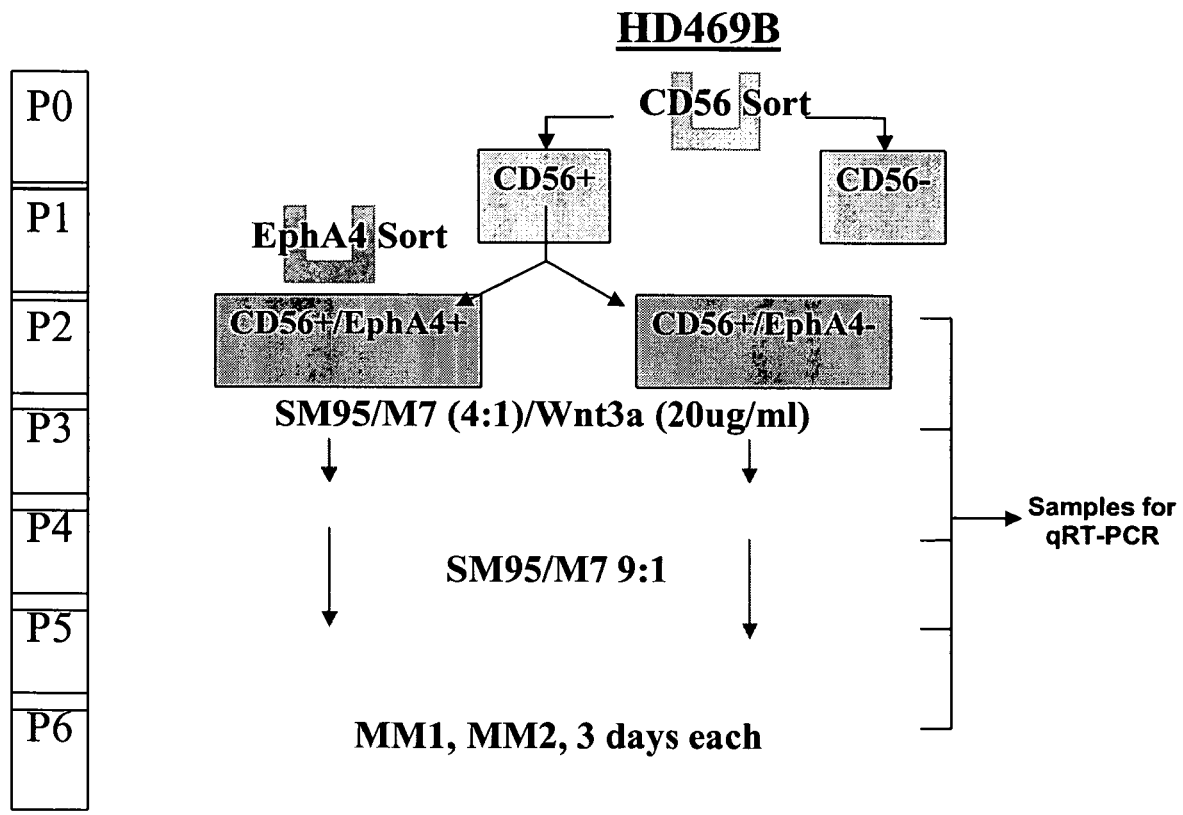
FIG. 12 shows a flow chart of "double selecting" cells for the presence of absence of both the EphA4 and CD56 markers. Presence of a cell marker on the sorted cells is indicated by a positive sign ("+"), its absence is indicated by a negative sign ("–").

The scheme of cell culture and cell sorting is shown in FIG. 12. HD469B (P0) cells were seeded in 10 cm plates in SM95/M7(4:1) medium and culture for 6 days at 37° C. Medium was changed every 2 days. On day 6, the HD469B cells were trypsinized and washed with PBS. The cells sorted with anti-CD56 antibody were coated with Magnetic Nanoparticles (StemCell Technologies) as described in Example 1. The sorted CD56 positive cells (P1) (about 10% of original cell population) and the CD56 negative cells were cultured in SM95/M7 for 3 days. The cells were trypsinized and washed with PBS. A small portion of the cells (10% of cell population) was passed into a 10 cm plate (CD56 positive P2) in SM95/M7(4:1) with 20 µg/ml Wnt3a proteins (R&D Systems, Inc). The majority of the cells were sorted with an antibody to EphA4 (BD Biosciences) coated with Magnetic Nanoparticles (StemCell Technologies) prepared as described in Example 1. The sorted CD56-EphA4 positive cells (P2) and CD56-EphA4 negative cells (P2) were cultured in SM95/M7(4:1) with 20 µg/ml Wnt3a proteins for 5 days. On day 5, CD56/EphA4 positive cells (P2), CD56/EphA4 negative cells (P2), CD56 positive cells (P2) and CD56 negative cells (P2) were trypsinized and washed with PBS. Small portions of cells from each group were harvested for RNA isolation for gene expression analysis by real-time PCR. This procedure was performed at each cell passage from P2-P5. The majority of the cells in all four groups were passed into P3 and cultured for three days in SM95/M7(4:1) with 20 µg/ml Wnt3a proteins. On passage 4 and 5, each of the four group cells were divided into 3 plates with different coating conditions, regular (control), fibronectin, and extra cellular matrix (ECM) coated plates. All cells were cultured in SM95/M7(9:1) for 3 day for each passage. At passage 6, cells were culture in MM1 and MM2 medium for 3 days, respectively. After culture in MM2, cells were collected for isolation of total RNA.

2. Insulin Expression in the CD56/EphA4 Double Selected Cells

Figure 13A:
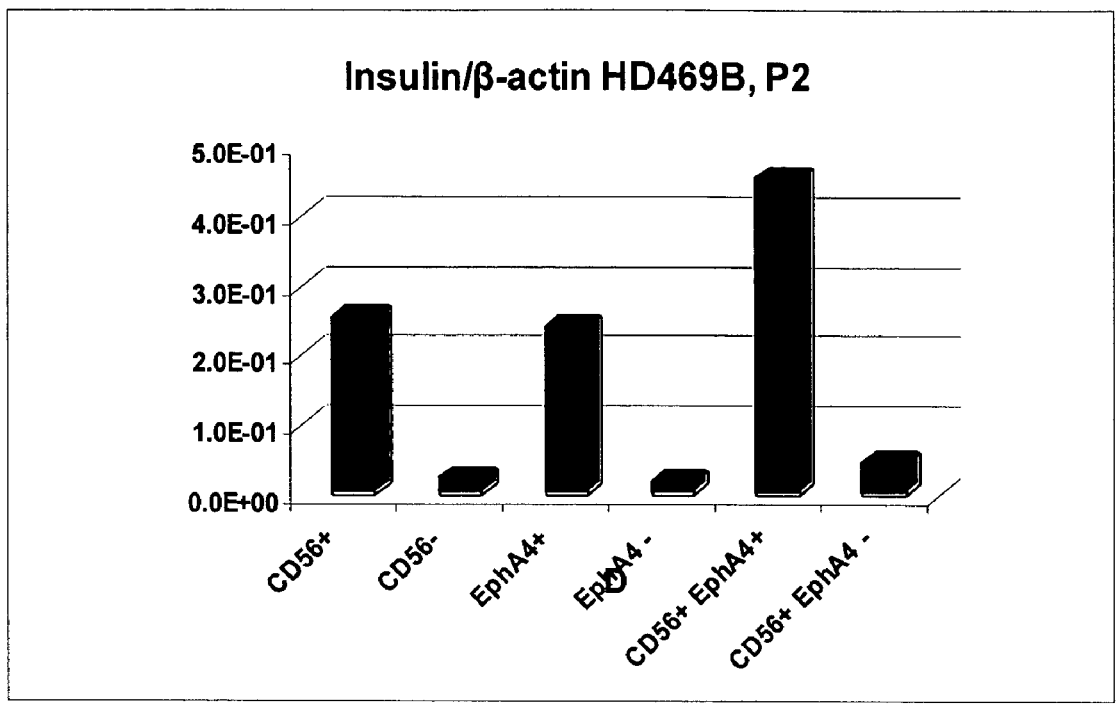
FIGS. 13a-d show the expression of insulin in EphA4 and CD56 double selected cells at different cell passages.
Figure 13B:
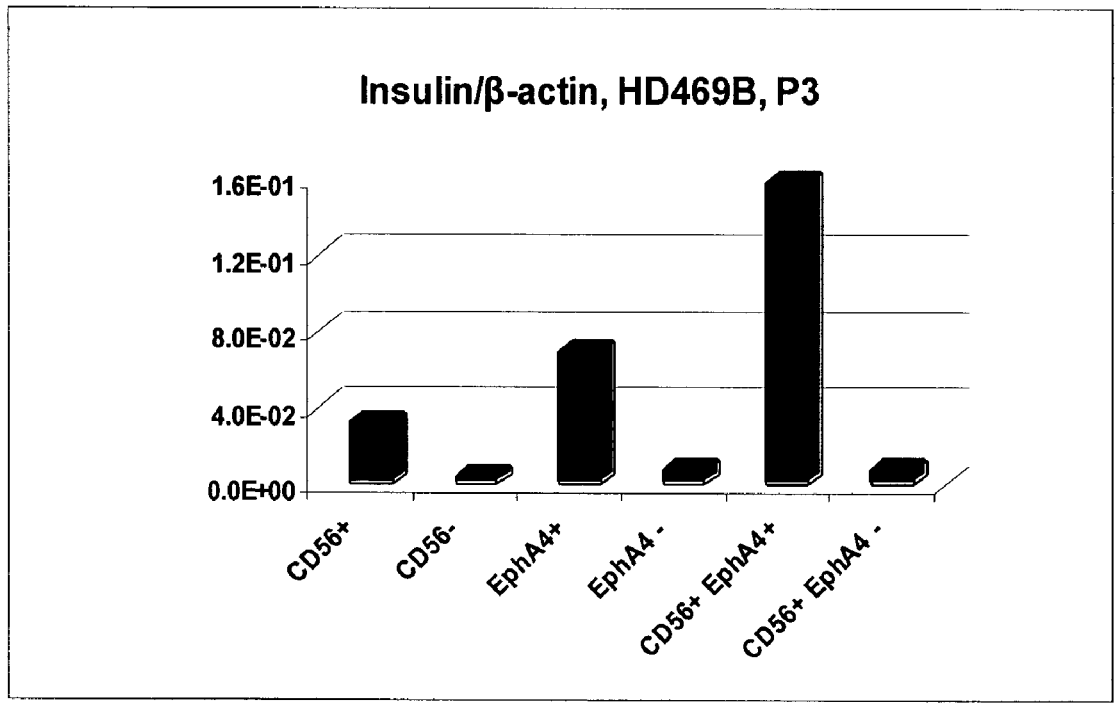
Figure 13C:
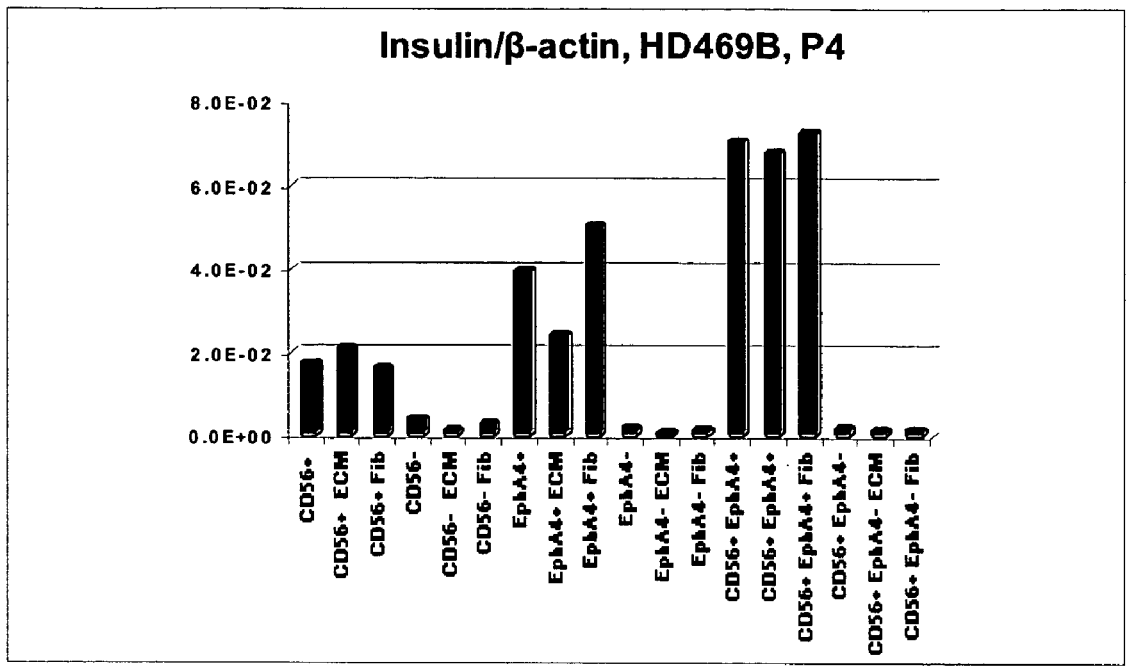
Figure 13D:
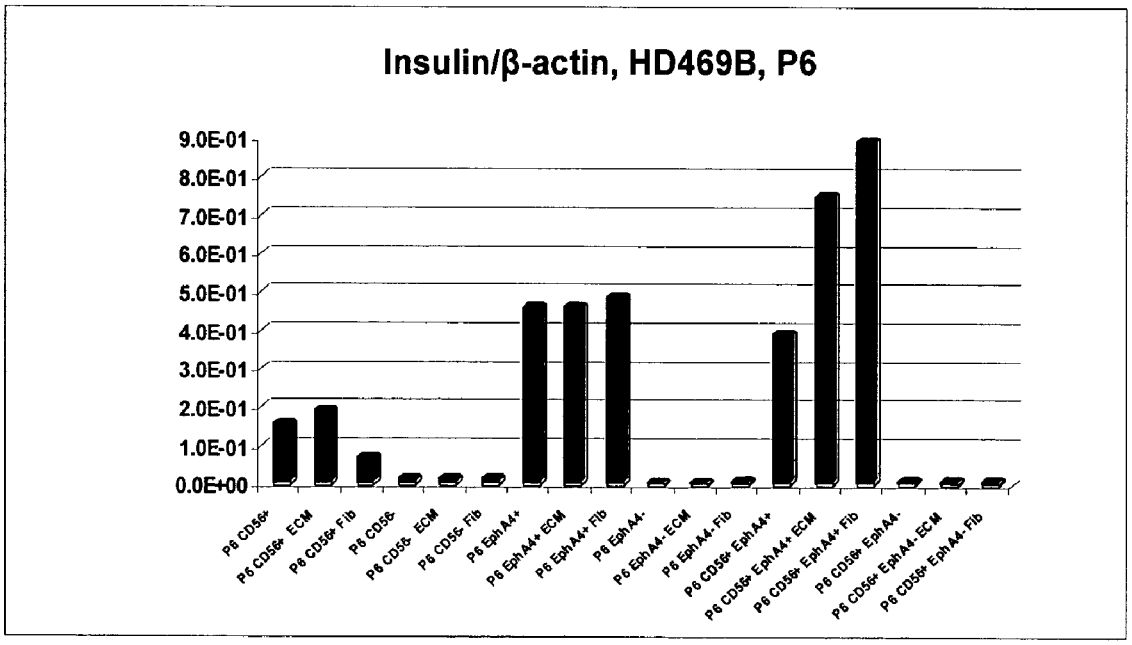
Figure 14A:
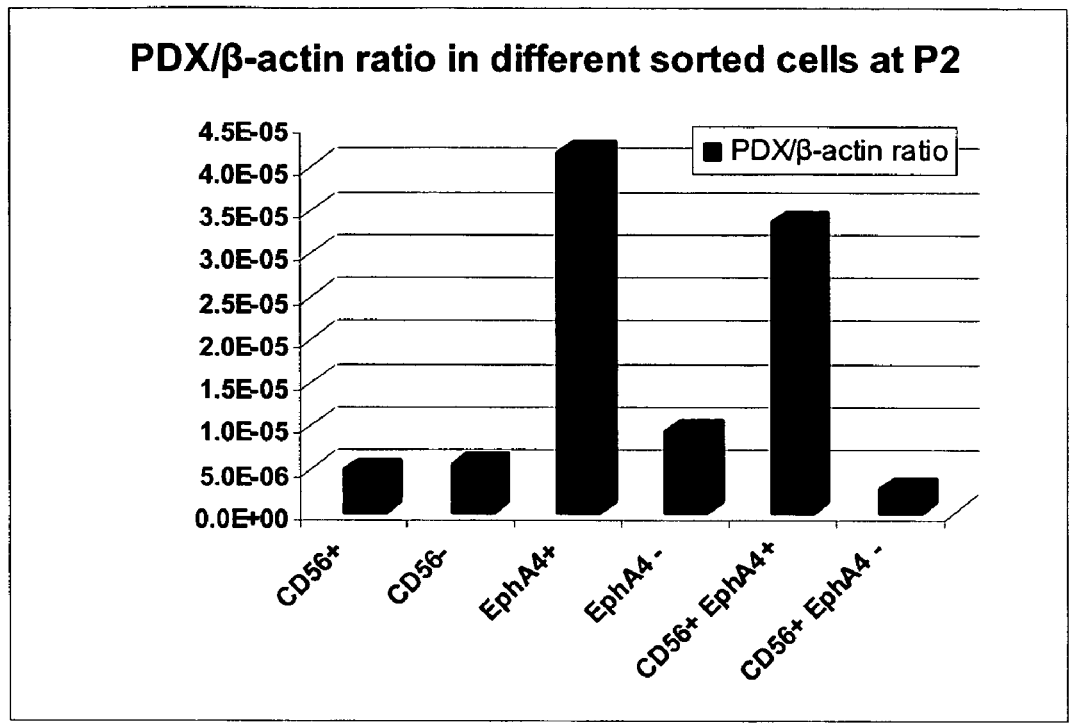
FIGS. 14a-d show a comparison of expression of the pancreatic gene PDX-1 in cells according to their expression of cell markers CD56 and EphA4 at various cell passages.
Figure 14B:
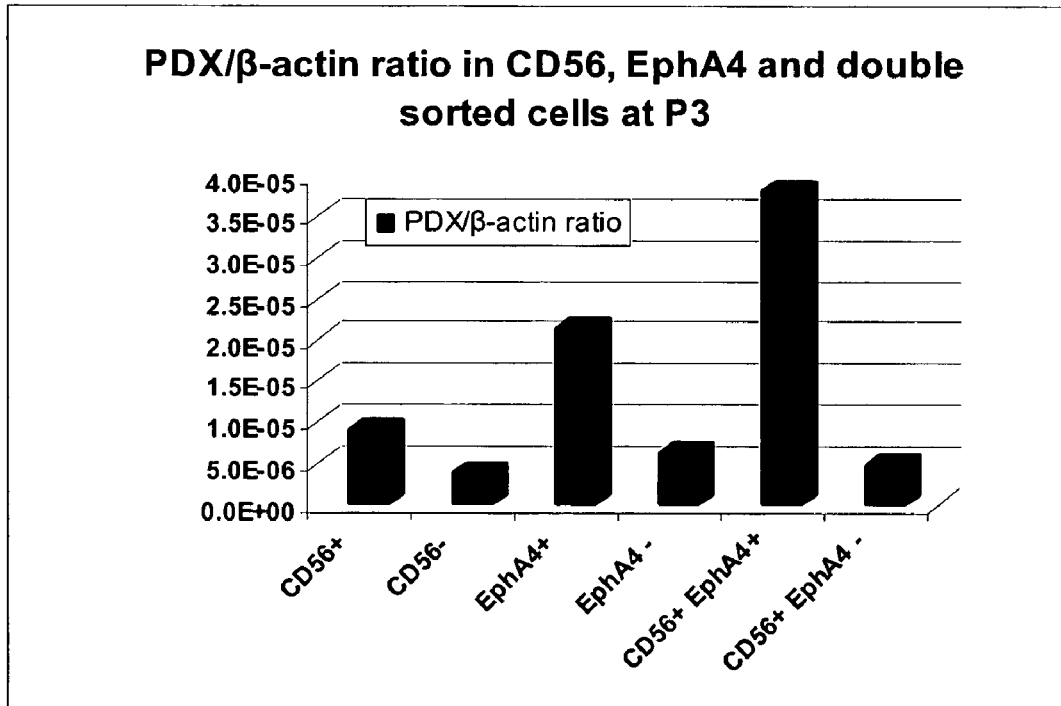
Figure 14C:
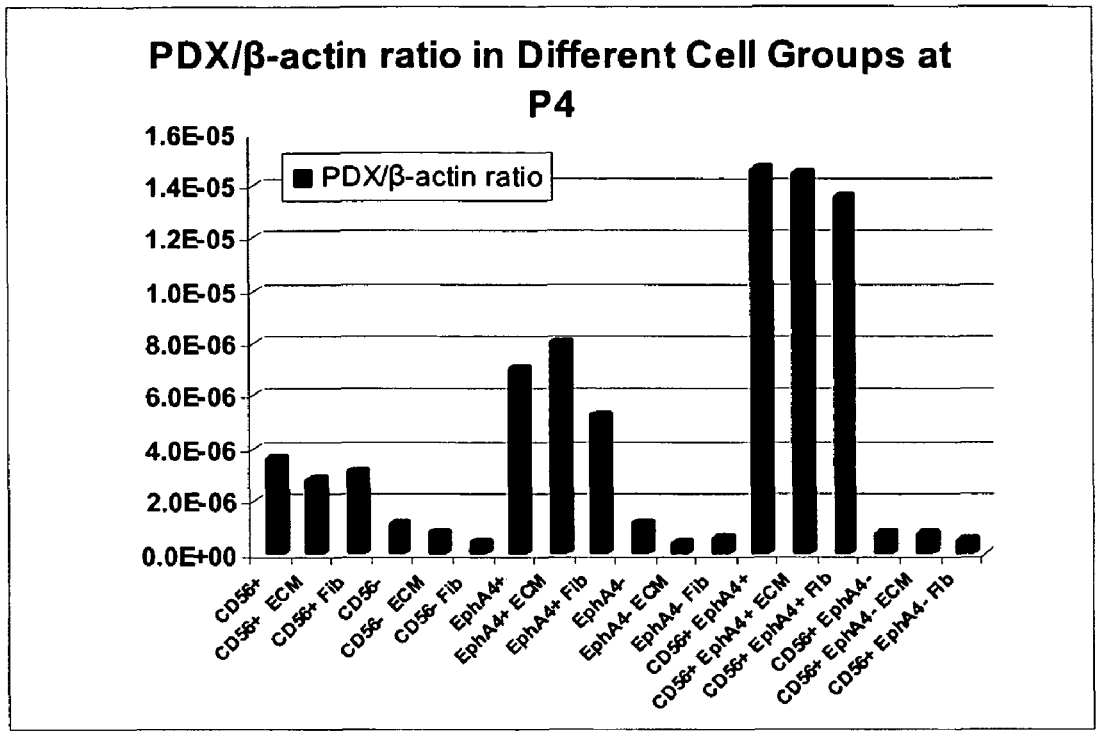
Figure 14D:
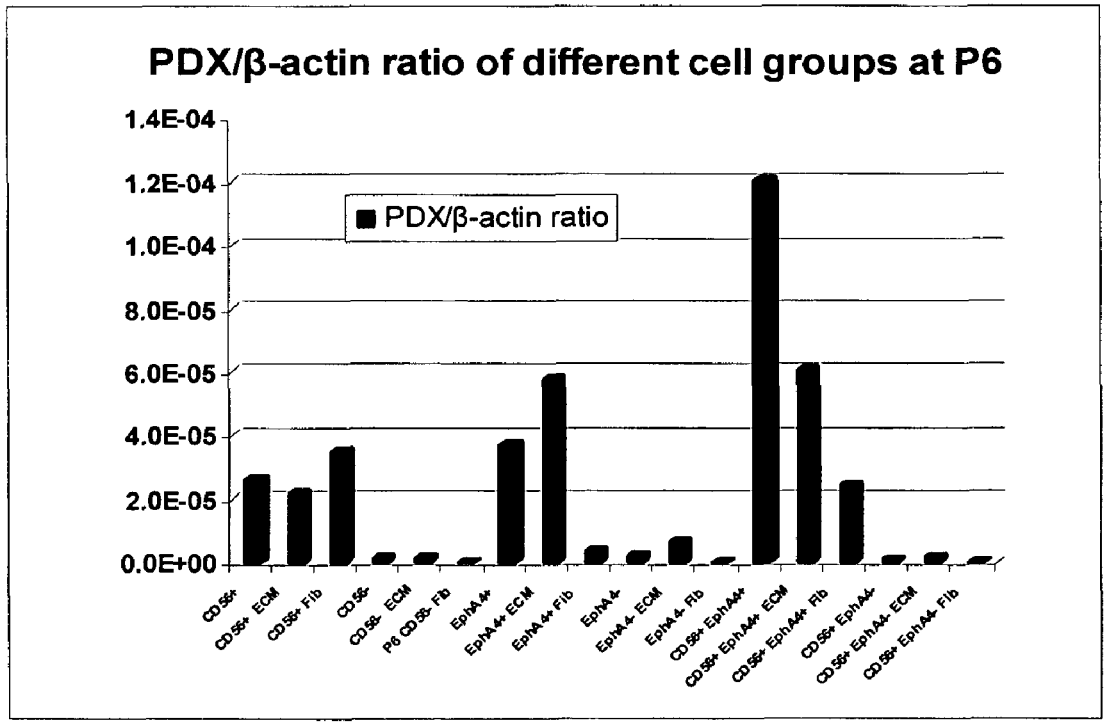

To characterize the CD56/EphA4 double positive cells, we first measured mRNA level of insulin among different cell groups by real time PCR. As shown in FIG. 13 and Table 7, CD56-EphA4 double positive cells have the highest expression of insulin among all the cell groups after sorting at P1 (FIG. 13A). The expression of insulin in CD56+/EphA4+ cells (0.46) were around two-fold higher compared to either CD56 single positive (0.25) or EphA4 single positive (0.24) cells (FIG. 13A). Significantly, the double positive cells maintained high expression of insulin through sequential passages with different culture conditions (FIG. 13B, C, D, Table 7). The mRNA levels of insulin in CD56+/EphA4+ cells were always 2~5 times higher than either CD56 or EphA4 single positive sorted cells during the passages. These results show that CD56/EphA4 double selection can enhance pancreatic endocrine phenotype of both CD56 positive or EphA4 positive cells.

Recently, another group used a method for genetic lineage tracing to determine the contribution of stem cells to β-cells. They showed the insulin producing cells are the major source of new β-cells during adult life in mice. These insulin producing β-cells progenitors are derived from either pre-exiting β-cells which were transiently dedifferentiated or stem cells which produce insulin.

TABLE 7

Insulin Expression of CD56, EphA4, and CD56/EphA4 double sorted cells at different passages

| HD469B | Insulin | β-actin | Ins/β-actin ratio |
|---|---|---|---|
| P2 CD56+ | 550,200 | 2,162,000 | 2.545E−01 |
| P2 CD56− | 256,100 | 11,050,000 | 2.318E−02 |
| P2 EphA4+ | 6,046,000 | 25,190,000 | 2.400E−01 |
| P2 EphA4− | 184,500 | 11,030,000 | 1.673E−02 |
| P2 CD56+ EphA4+ | 9,960,000 | 21,850,000 | 4.558E−01 |
| P2 CD56+ EphA4− | 98,210 | 2,095,000 | 4.688E−02 |
| P3 CD56+ | 494,500 | 15,610,000 | 3.168E−02 |
| P3 CD56− | 14,070 | 4,916,000 | 2.862E−03 |
| P3 EphA4+ | 425,800 | 6,108,000 | 6.971E−02 |
| P3 EphA4− | 26,180 | 3,523,000 | 7.431E−03 |
| P3 CD56+ EphA4+ | 1,878,000 | 11,900,000 | 1.578E−01 |
| P3 CD56+ EphA4− | 51,100 | 7,943,000 | 6.433E−03 |
| P4 CD56+ | 232,400 | 13,360,000 | 1.740E−02 |
| P4 CD56+ ECM | 148,700 | 7,160,000 | 2.077E−02 |
| P4 CD56+ Fib | 216,400 | 13,280,000 | 1.630E−02 |
| P4 CD56− | 51,500 | 13,200,000 | 3.902E−03 |
| P4 CD56− ECM | 8,556 | 7,054,000 | 1.213E−03 |
| P4 CD56− Fib | 29,930 | 12,000,000 | 2.494E−03 |
| P4 EphA4+ | 569,000 | 14,390,000 | 3.954E−02 |
| P4 EphA4+ ECM | 318,900 | 13,320,000 | 2.394E−02 |
| P4 EphA4+ Fib | 236,700 | 4,701,000 | 5.035E−02 |
| P4 EphA4− | 21,970 | 11,940,000 | 1.840E−03 |
| P4 EphA4− ECM | 8,339 | 14,950,000 | 5.578E−04 |
| P4 EphA4− Fib | 9,268 | 9,661,000 | 9.593E−04 |

TABLE 7-continued

Insulin Expression of CD56, EphA4, and CD56/EphA4 double sorted cells at different passages

| HD469B | Insulin | β-actin | Ins/β-actin ratio |
|---|---|---|---|
| P4 CD56+ EphA4+ | 1,203,000 | 17,010,000 | 7.072E-02 |
| P4 CD56+ EphA4+ ECM | 812,600 | 11,990,000 | 6.777E-02 |
| P4 CD56+ EphA4+ Fib | 910,600 | 12,530,000 | 7.267E-02 |
| P4 CD56+ EphA4− | 22,750 | 13,010,000 | 1.749E-03 |
| P4 CD56+ EphA4− ECM | 10,880 | 9,459,000 | 1.150E-03 |
| P4 CD56+ EphA4− Fib | 6,673 | 5,468,000 | 1.220E-03 |
| P6 CD56+ | 37,080 | 239,800 | 1.546E-01 |
| P6 CD56+ ECM | 28,150 | 147,800 | 1.905E-01 |
| P6 CD56+ Fib | 72,330 | 1,022,000 | 7.077E-02 |
| P6 CD56− | 4,849 | 380,200 | 1.275E-02 |
| P6 CD56− ECM | 5,939 | 450,300 | 1.319E-02 |
| P6 CD56− Fib | 3,899 | 337,200 | 1.156E-02 |
| P6 EphA4+ | 93,840 | 204,800 | 4.582E-01 |
| P6 EphA4+ ECM | 62,210 | 135,000 | 4.608E-01 |
| P6 EphA4+ Fib | 41,600 | 85,440 | 4.869E-01 |
| P6 EphA4− | 1,847 | 449,900 | 4.105E-03 |
| P6 EphA4− ECM | 541 | 255,400 | 2.117E-03 |
| P6 EphA4− Fib | 2,076 | 367,100 | 5.655E-03 |
| P6 CD56+ EphA4+ | 395,500 | 1,016,000 | 3.893E-01 |
| P6 CD56+ EphA4+ ECM | 172,500 | 231,000 | 7.468E-01 |
| P6 CD56+ EphA4+ Fib | 101,800 | 114,100 | 8.922E-01 |
| P6 CD56+ EphA4− | 885 | 101,100 | 8.753E-03 |
| P6 CD56+ EphA4− ECM | 2,323 | 382,700 | 6.070E-03 |
| P6 CD56+ EphA4− Fib | 2,351 | 375,500 | 6.261E-03 |

3. Expression of PDX-1 in the CD56/EphA4 Double Selected Cells

We analyzed the expression of pancreatic gene PDX-1 among different cell groups during the cell passages. PDX-1 plays important role during pancreatic development lineage including the specification, proliferation and differentiation of pancreatic cell types. It activates the transcription of many β-cell genes involved in glucose homeostasis including insulin, glucokinase and the glucose transporter GLUT2. PDX-1 is expressed during pancreatic development with high levels of expression in both early embryonic endodermally derived cells and differentiated β-cells. A conditional PDX-1 null mouse model demonstrated that PDX-1 is not only required for proper specification of different pancreatic cell types, but also for pancreatic progenitor cells to differentiate into β-cells (Holland et al., Proc Natl Acad Sci 99(19):12236-41 (2002)). mRNA levels of PDX-1 were measured among different cell culture groups by real-time PCR. As shown in FIG. 14 and Table 8, CD56/EphA4 double positive cells showed higher PDX-1 expression than CD56 positive cells through out all the passages (P2-P6). The expression of PDX-1 in CD56/EphA4 double positive cells was higher compared with the EphA4 single positively sorted cells during P3~P6. At P2, both CD56+/EphA4+ and EphA4+ cells had similar levels of PDX-1 expression. These data further support that EphA4 can further enhance pancreatic endocrine phenotype of CD56 selected cells.

TABLE 8

Expression of PDX-1 in CD56−, EphA4−, and CD56/EphA4 double-sorted cells at different passages

| HD469B | PDX-1 | β-actin | PDX/β-actin ratio |
|---|---|---|---|
| P2 CD56+ | 11 | 2,162,000 | 4.97E-06 |
| P2 CD56− | 64 | 11,050,000 | 5.75E-06 |
| P2 EphA4+ | 1054 | 25,190,000 | 4.18E-05 |
| P2 EphA4− | 105 | 11,030,000 | 9.49E-06 |
| P2 CD56+ EphA4+ | 738 | 21,850,000 | 3.37E-05 |
| P2 CD56+ EphA4− | 6 | 2,095,000 | 2.78E-06 |
| P3 CD56+ | 143 | 15,610,000 | 9.16E-06 |
| P3 CD56− | 20 | 4,916,000 | 3.97E-06 |
| P3 EphA4+ | 131 | 6,108,000 | 2.15E-05 |
| P3 EphA4− | 22 | 3,523,000 | 6.33E-06 |
| P3 CD56+ EphA4+ | 457 | 11,900,000 | 3.84E-05 |
| P3 CD56+ EphA4− | 39 | 7,943,000 | 4.87E-06 |
| P4 CD56+ | 49 | 13,360,000 | 3.641E-06 |
| P4 CD56+ ECM | 20 | 7,160,000 | 2.778E-06 |
| P4 CD56+ Fib | 42 | 13,280,000 | 3.127E-06 |
| P4 CD56− | 15 | 13,200,000 | 1.123E-06 |
| P4 CD56− ECM | 6 | 7,054,000 | 7.851E-07 |
| P4 CD56− Fib | 5 | 12,000,000 | 4.363E-07 |
| P4 EphA4+ | 101 | 14,390,000 | 6.984E-06 |
| P4 EphA4+ ECM | 107 | 13,320,000 | 8.048E-06 |
| P4 EphA4+ Fib | 25 | 4,701,000 | 5.269E-06 |
| P4 EphA4− | 14 | 11,940,000 | 1.157E-06 |
| P4 EphA4− ECM | 6 | 14,950,000 | 4.131E-07 |
| P4 EphA4− Fib | 5 | 9,661,000 | 5.612E-07 |
| P4 CD56+ EphA4+ | 249 | 17,010,000 | 1.461E-05 |
| P4 CD56+ EphA4+ ECM | 173 | 11,990,000 | 1.443E-05 |
| P4 CD56+ EphA4+ Fib | 170 | 12,530,000 | 1.355E-05 |
| P4 CD56+ EphA4− | 10 | 13,010,000 | 7.636E-07 |
| P4 CD56+ EphA4− ECM | 7 | 9,459,000 | 7.742E-07 |
| P4 CD56+ EphA4− Fib | 3 | 5,468,000 | 4.702E-07 |
| P6 CD56+ | 6 | 239,800 | 2.604E-05 |
| P6 CD56+ ECM | 3 | 147,800 | 2.179E-05 |
| P6 CD56+ Fib | 36 | 1,022,000 | 3.494E-05 |
| P6 CD56− | 0 | 380,200 | 1.021E-06 |
| P6 CD56− ECM | 1 | 450,300 | 1.528E-06 |
| P6 CD56− Fib | 0 | 337,200 | 0.000E+00 |
| P6 EphA4+ | 8 | 204,800 | 3.695E-05 |
| P6 EphA4+ ECM | 8 | 135,000 | 5.785E-05 |
| P6 EphA4+ Fib | 0 | 85,440 | 3.538E-06 |
| P6 EphA4− | 1 | 449,900 | 2.071E-06 |
| P6 EphA4− ECM | 2 | 255,400 | 6.143E-06 |
| P6 EphA4− Fib | 0 | 367,100 | 0.000E+00 |
| P6 CD56+ EphA4+ | 123 | 1,016,000 | 1.207E-04 |
| P6 CD56+ EphA4+ ECM | 14 | 231,000 | 6.039E-05 |
| P6 CD56+ EphA4+ Fib | 3 | 114,100 | 2.430E-05 |
| P6 CD56+ EphA4− | 0 | 101,100 | 9.066E-07 |
| P6 CD56+ EphA4− ECM | 1 | 382,700 | 1.662E-06 |
| P6 CD56+ EphA4− Fib | 0 | 375,500 | 0.000E+00 |

4. Expression of Nkx2.2 and Pax6 in the CD56/EphA4 Double Selected Cells

Two pancreatic progenitor markers, Nkx2.2 and Pax6, were also used to evaluate our pancreatic culture cells. Nkx2.2 is a homeodomain transcription factor expressed in early stage of pancreatic developments. It is expressed in the pancreatic bud until E13 when it becomes localized to the neurogenin3-expressing progenitor cells. Nkx2.2 null mice have a complete absence of insulin-producing cells (Sussel et al, Development, 125(12):2213-21 (1998)). Pax6 is a late factor after neurogenin3 expression and in conjunction with hormone gene expression. Pax6 is critical to the development and maintenance of the final differentiated islet cell phenotypes. Loss of Pax6 causes defects in the generation of all endocrine cell types (Ahlgren et al., Nature 385:257-60 (1997)). Expression of Nkx2.2 and Pax6 in different cell groups was quantified by real-time PCR. The expression of Nkx2.2 in CD56/EphA4 positive cells was higher than either CD56 or EphA4 positive cell at different cell passages (FIG. 15). As expected, the expression of Pax6 in the different sorted cells had a very similar pattern to and tendency as the expression of Nkx2.2. CD56/EphA4 positive cells have higher expression of Pax6 than either CD56 or EphA4 sorted cells during all the passages (FIG. 16). These results show that the EphA4 selection cells can further enrich the progenitor cells of either CD56 positive or EphA4 positive cells.

TABLE 9

Expression of NKx2.2 and Pax6 in CD56, EphA4, or Double Sorted Cells at Different Cell Passages

| HD469B | β-actin | Nkx2.2 | Nkx2.2/β-actin ratio | Pax6 | Pax6/β-actin ratio |
|---|---|---|---|---|---|
| P2 CD56+ | 2,162,000 | 10 | 4.820E−06 | 808 | 3.735E−04 |
| P2 CD56− | 11,050,000 | 36 | 3.271E−06 | 608 | 5.502E−05 |
| P2 EphA4+ | 25,190,000 | 1087 | 4.315E−05 | 10960 | 4.351E−04 |
| P2 EphA4 − | 11,030,000 | 42 | 3.770E−06 | 445 | 4.037E−05 |
| P2 CD56+ EphA4+ | 21,850,000 | 1092 | 4.998E−05 | 22360 | 1.023E−03 |
| P2 CD56− EphA4− | 2,095,000 | 2 | 1.151E−06 | 130 | 6.224E−05 |
| P3 CD56+ | 15,610,000 | 133 | 8.533E−06 | 1581 | 1.013E−04 |
| P3 CD56− | 4,916,000 | 6 | 1.162E−06 | 73 | 1.491E−05 |
| P3 EphA4+ | 6,108,000 | 164 | 2.687E−05 | 1180 | 1.932E−04 |
| P3 EphA4− | 3,523,000 | 6 | 1.672E−06 | 80 | 2.262E−05 |
| P3 CD56+ EphA4+ | 11,900,000 | 482 | 4.051E−05 | 4714 | 3.961E−04 |
| P3 CD56− EphA4− | 7,943,000 | 8 | 1.008E−06 | 148 | 1.866E−05 |
| P4 CD56+ | 13,360,000 | 36 | 2.703E−06 | 544 | 4.070E−05 |
| P4 CD56− | 13,200,000 | 22 | 1.644E−06 | 121 | 9.144E−06 |
| P4 EphA4+ | 14,390,000 | 66 | 4.577E−06 | 1066 | 7.408E−05 |
| P4 EphA4− | 11,940,000 | 11 | 9.062E−07 | 66 | 5.562E−06 |
| P4 CD56+ EphA4+ | 17,010,000 | 159 | 9.371E−06 | 2607 | 1.533E−04 |
| P4 CD56− EphA4− | 13,010,000 | 6 | 4.396E−07 | 53 | 4.071E−06 |
| P5 CD56+ | 1,176,000 | 2 | 1.481E−06 | 28 | 2.371E−05 |
| P5 CD56− | 1,408,000 | 0 | 0.000E+00 | 6 | 3.960E−06 |
| P5 EphA4+ | 373,400 | 1 | 1.379E−06 | 9 | 2.464E−05 |
| P5 EphA4− | 1,089,000 | 1 | 5.481E−07 | 3 | 2.583E−06 |
| P5 CD56+ EphA4+ | 4,701,000 | 35 | 7.375E−06 | 321 | 6.826E−05 |
| P5 CD56+ EphA4− | 10,930,000 | 1 | 5.500E−08 | 10 | 9.552E−07 |
| P6 CD56+ | 239,800 | 5 | 1.958E−05 | 75 | 3.146E−04 |
| P6 CD56− | 380,200 | 1 | 3.019E−06 | 28 | 7.412E−05 |
| P6 EphA4+ | 204,800 | 11 | 5.498E−05 | 197 | 9.624E−04 |
| P6 EphA4− | 449,900 | 3 | 7.619E−06 | 7 | 1.528E−05 |
| P6 CD56+ EphA4+ | 1,016,000 | 99 | 9.727E−05 | 1378 | 1.356E−03 |
| P6 CD56+ EphA4− | 101,100 | 0 | 2.419E−06 | 5 | 4.539E−05 |

Example 4

Figure 17:
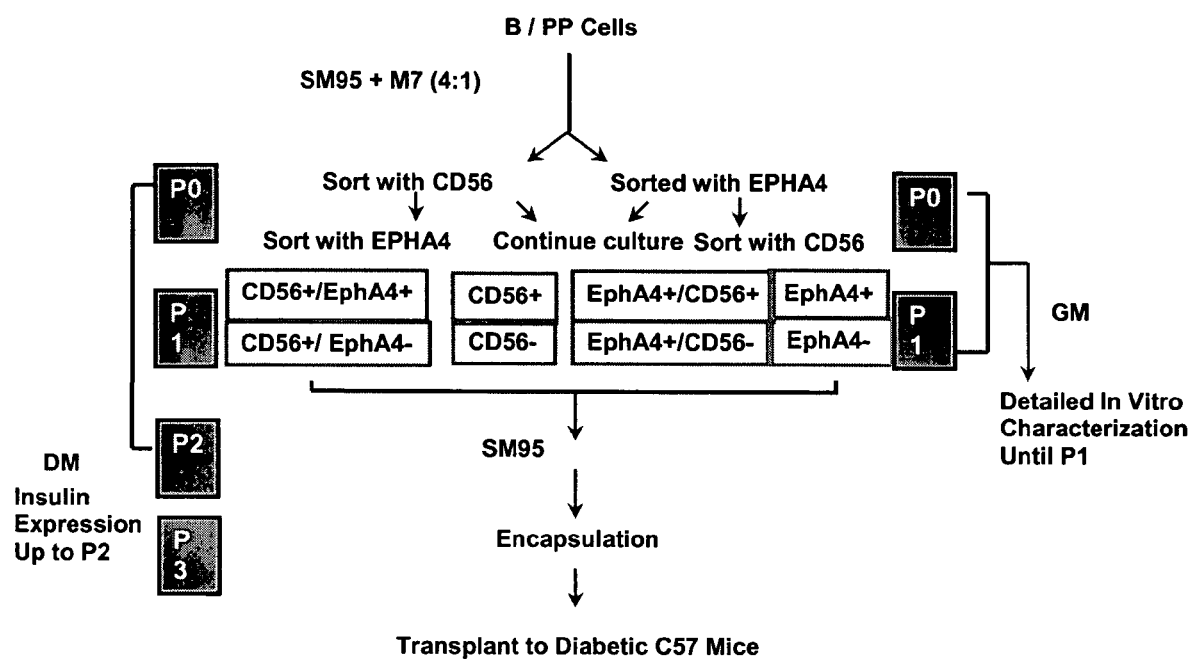
FIG. 17 shows a flow chart for cell sorting, encapsulation, and transplantation of cells with or without EphA4, CD56, or both cell markers, into diabetic C57 mice. Presence of a cell marker on the sorted cells is indicated by a positive sign ("+"), its absence is indicated by a negative sign ("−").
Figure 18:
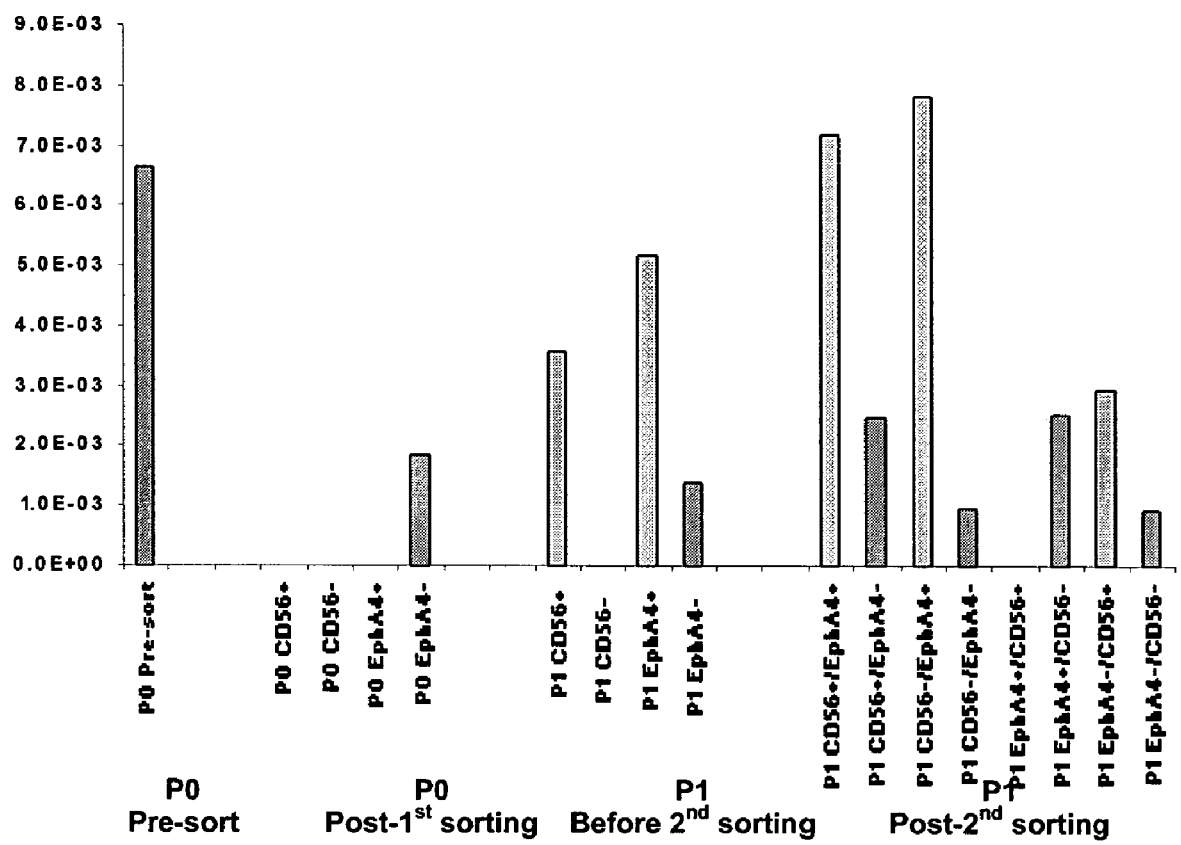
FIG. 18 shows the CD56 levels in sorted cells after various cell passages. P0 pre-sorting: cells in passage before sorting for cell markers. P0 post-1st sorting, cells in passage just after sorting. P1 before second sorting: first cell passage after 1st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 19:
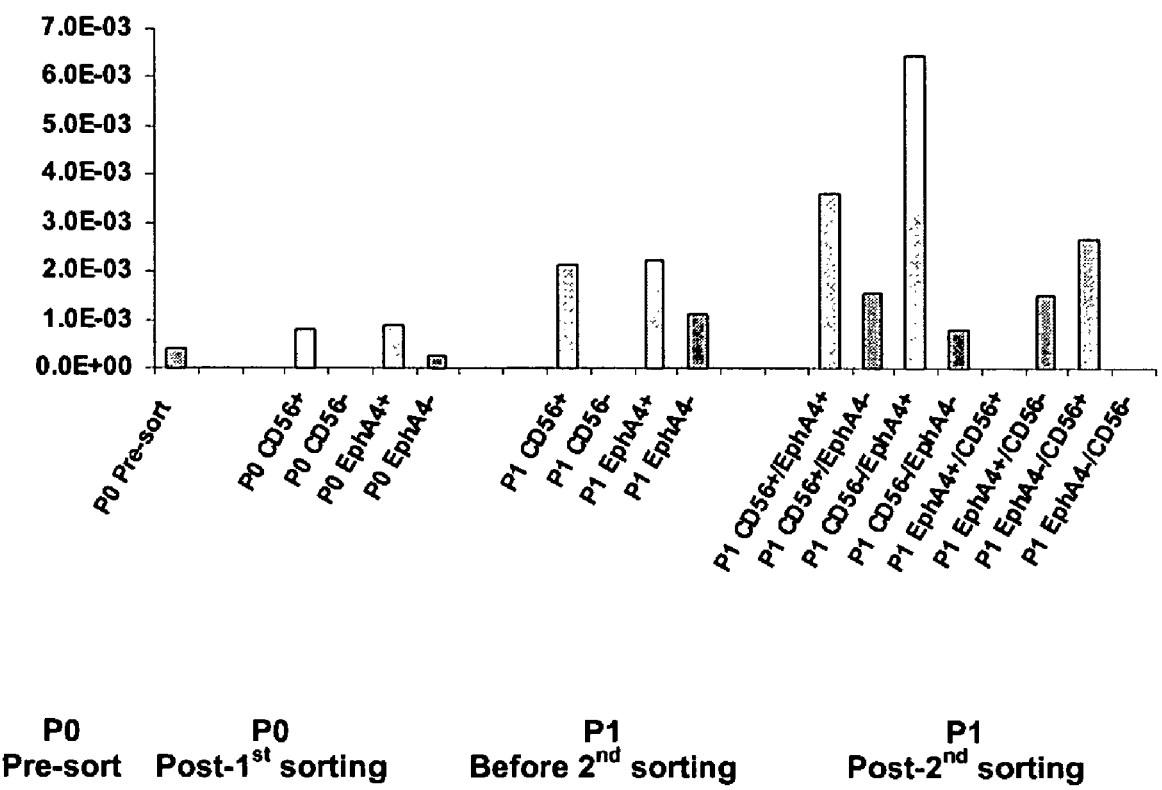
FIG. 19 shows the EphA4 levels in sorted cells after various cell passages. P0 pre-sorting: cells in passage before sorting for cell markers. P0 post-1st sorting, cells in passage just after sorting. P1 before second sorting: first cell passage after 1 st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 20:
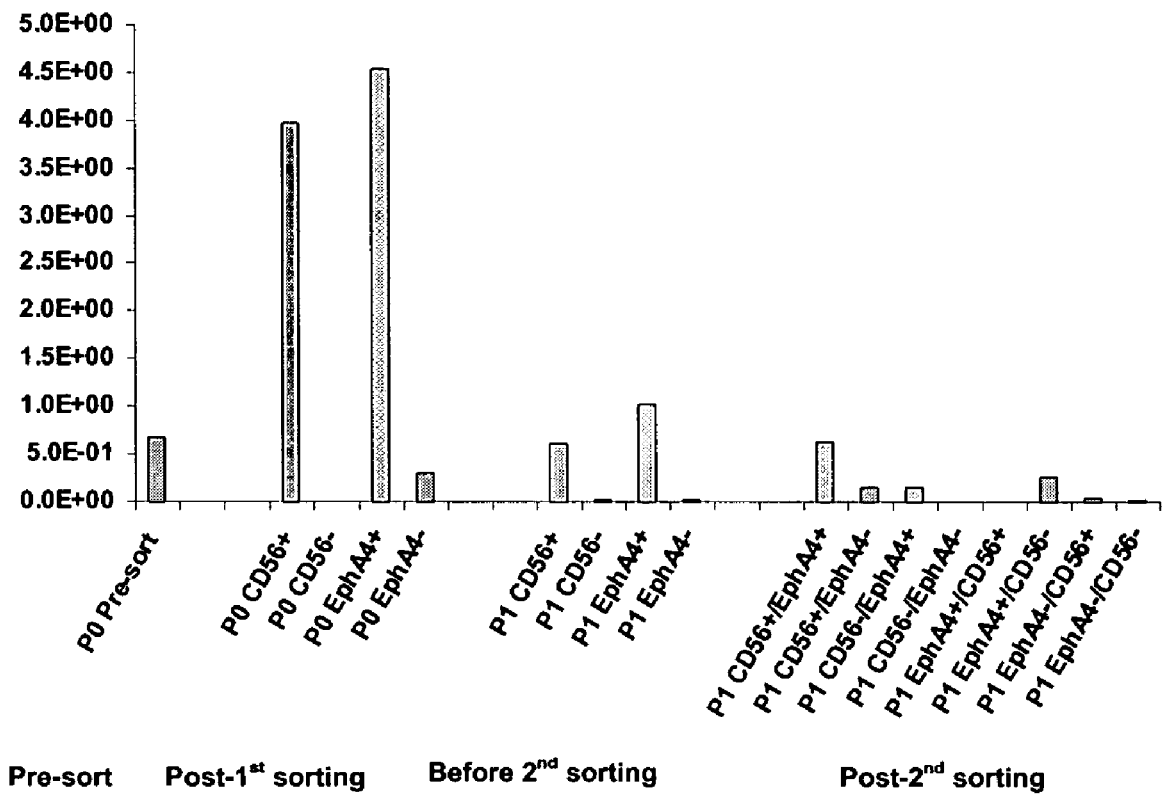
FIG. 20 shows the insulin levels in sorted cells after various cell passages. P0 pre-sorting: cells in passage before sorting for cell markers. P0 post-1st sorting, cells in passage just after sorting. P1 before second sorting: first cell passage after 1st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 21:
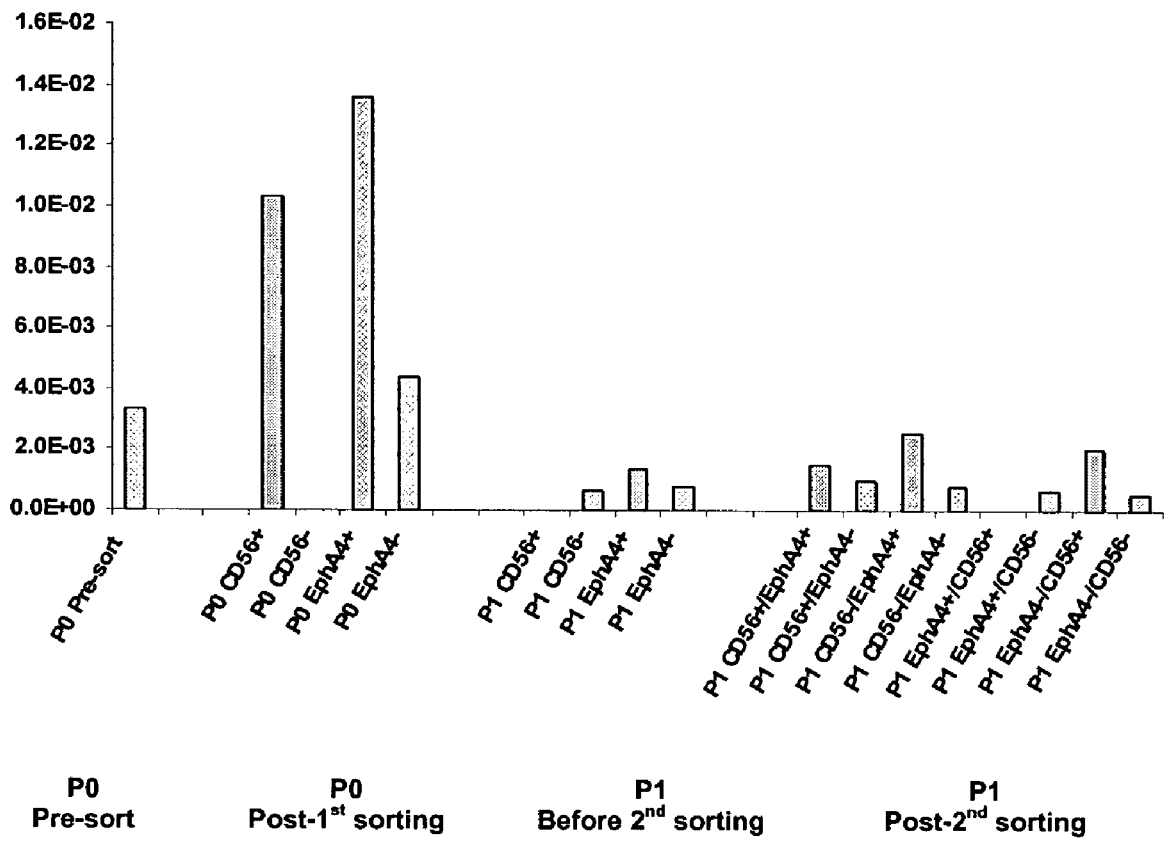
FIG. 21 shows the PDX-1 levels in sorted cells after various cell passages. P0 pre-sorting: cells in passage before sorting for cell markers. P0 post-1st sorting, cells in passage just after sorting. P1 before second sorting: first cell passage after 1st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 22:
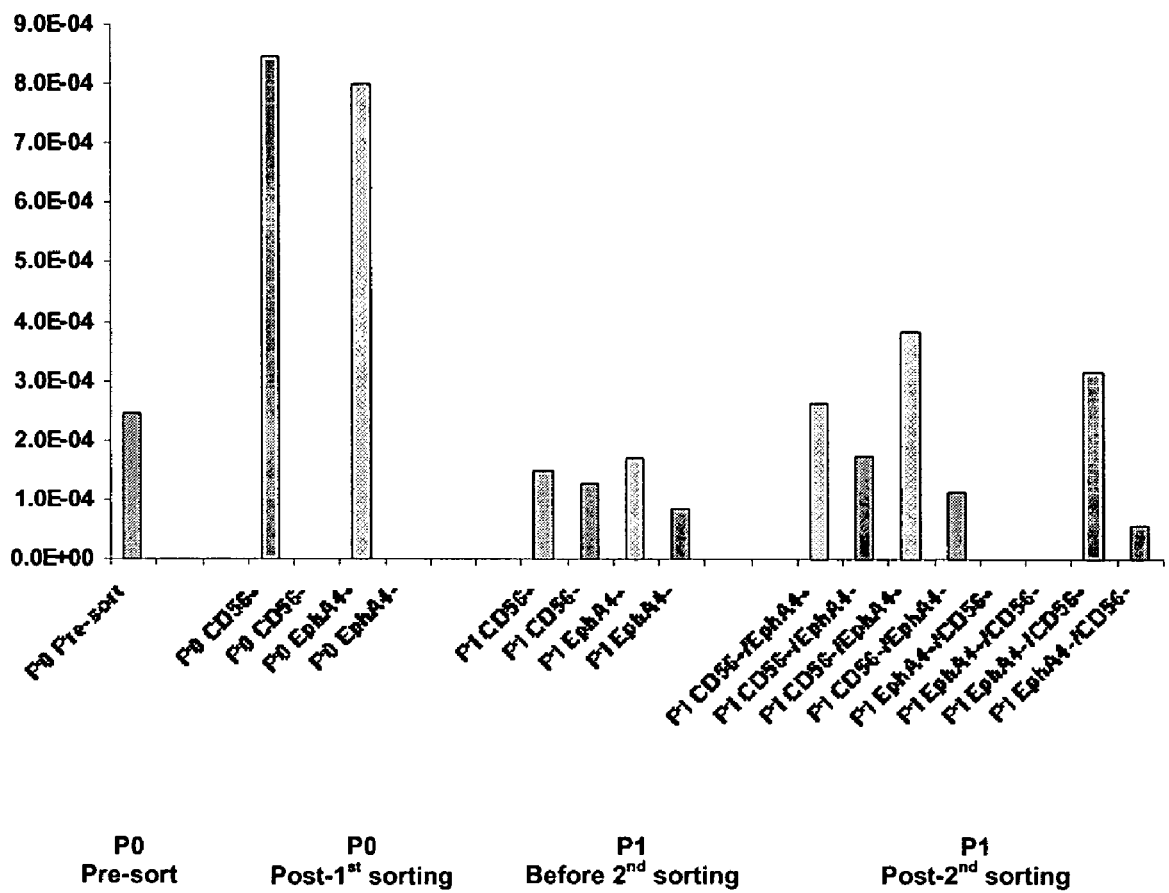
FIG. 22 shows GLUT2 levels in sorted cells after various cell passages (GLUT2, or glucose transporter, type 2, is the major glucose transporter isoform expressed in insulin-secreting pancreatic beta cells). P0 pre-sorting: cells in passage before sorting for cell markers. P0 post-1st sorting, cells in passage just after sorting. P1 before second sorting: first cell passage after 1st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 23:
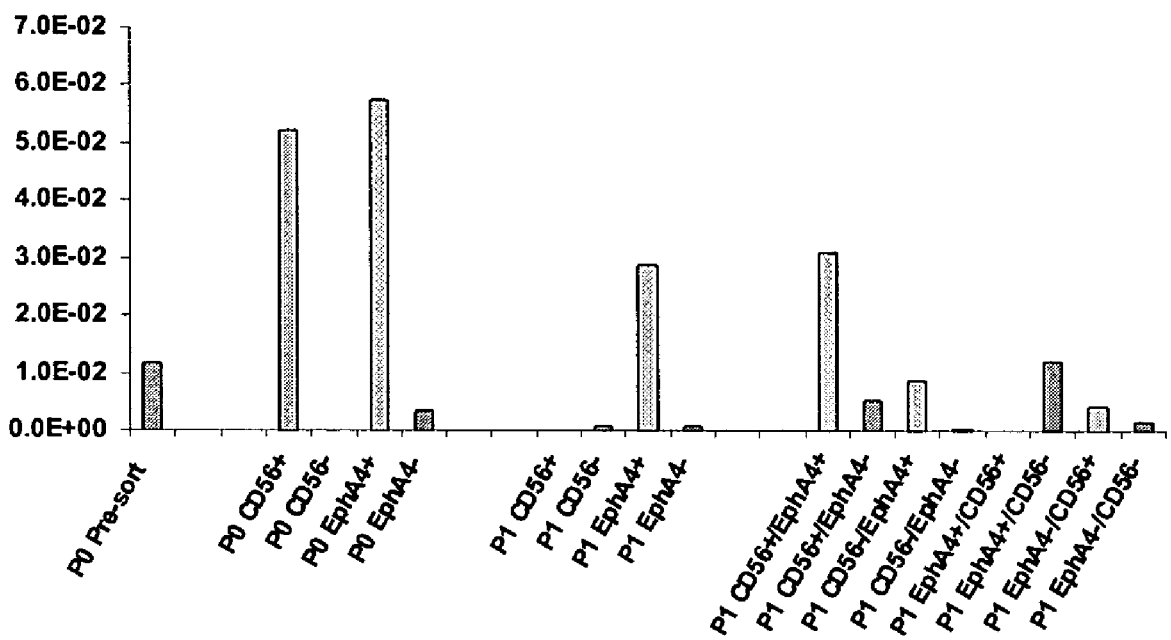
FIG. 23 shows the glucagon levels in sorted cells after various cell passages (glucagon is a linear peptide of 29 amino acids that has a major role in maintaining normal levels of blood glucose). P0 pre-sorting: cells in passage before sorting for cell markers. P0 post-1st sorting, cells in passage just after sorting. P1 before second sorting: first cell passage after 1st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 24:
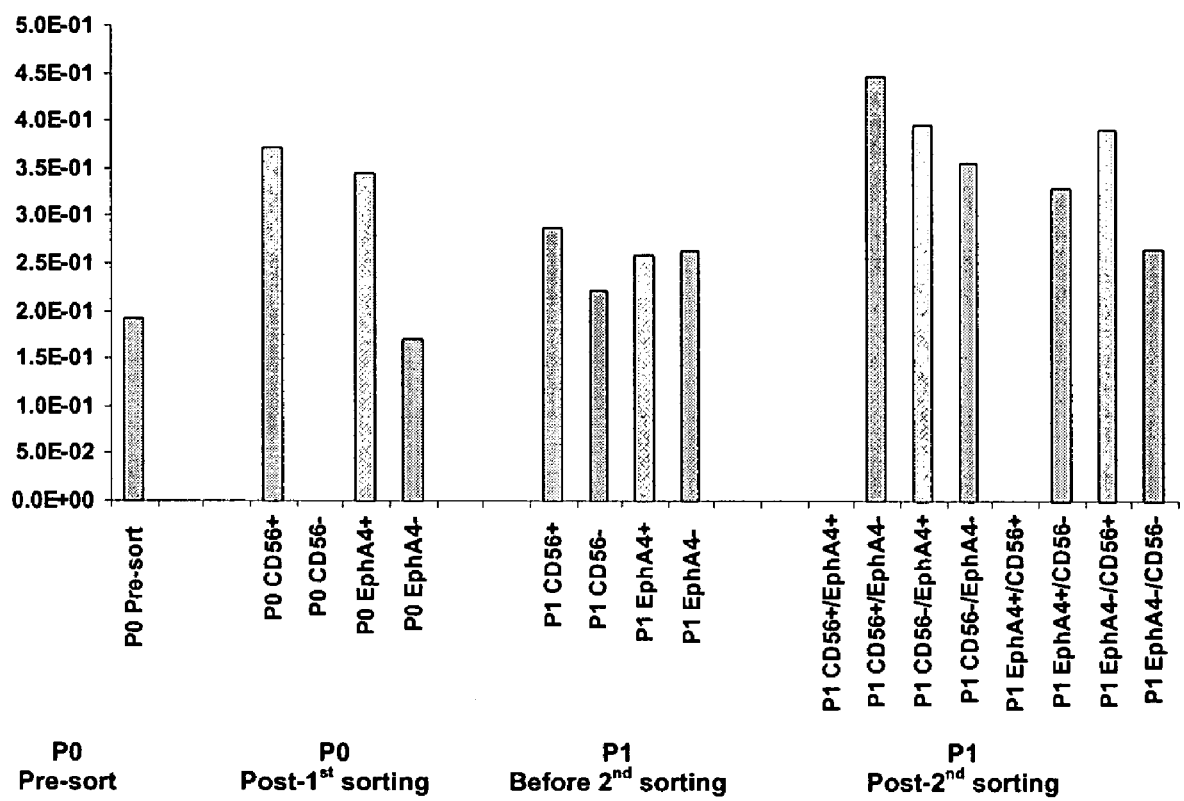
FIG. 24 shows the CK19 levels in sorted cells after various cell passages. P0 pre-sorting: cells in passage before sorting for cell markers. P0 post-1st sorting, cells in passage just after sorting. P1 before second sorting: first cell passage after 1st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").
Figure 25:
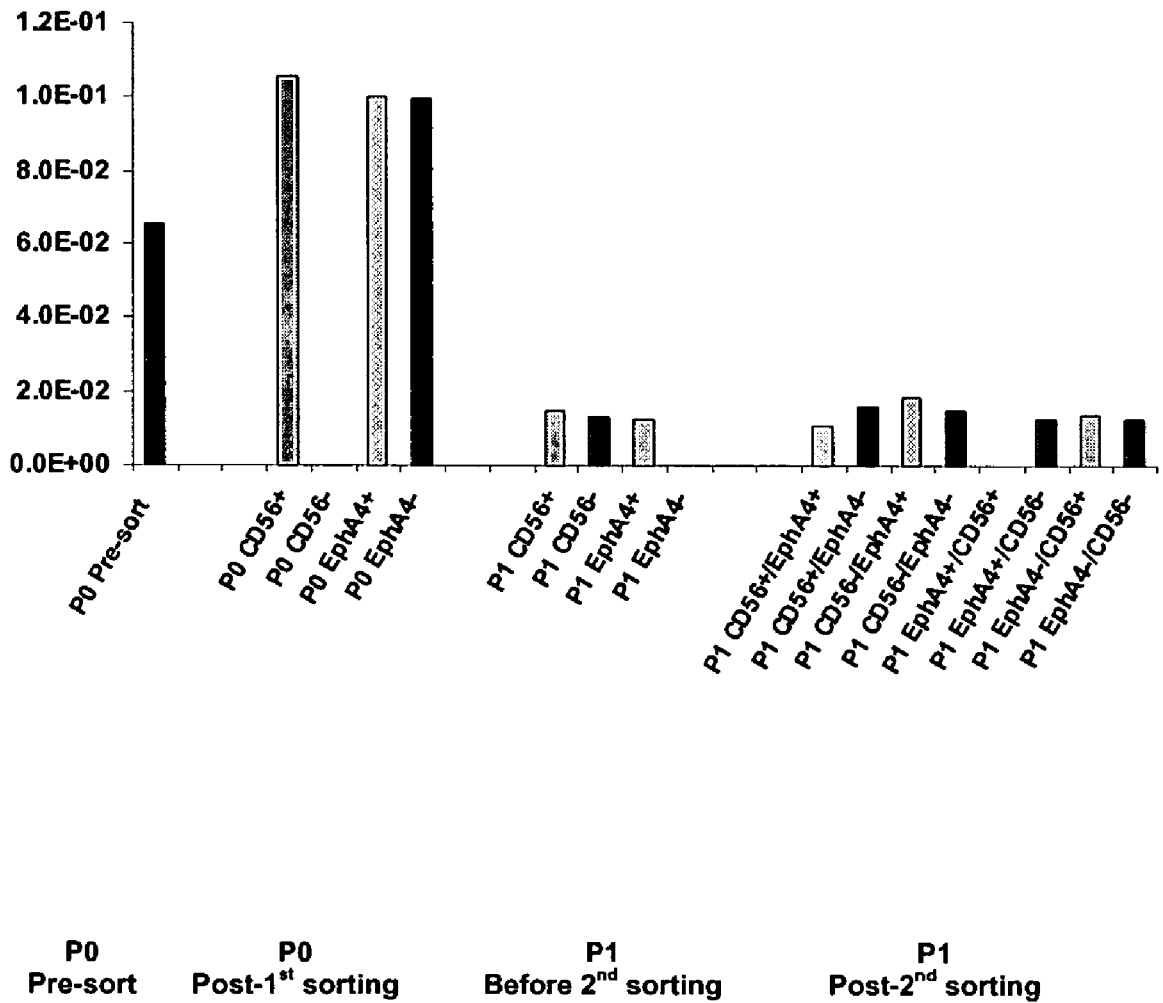
FIG. 25 shows the pancreatic amylase levels in sorted cells after various cell passages (pancreatic amylase is a pancreatic saccharidase). P0 pre-sorting: cells in passage before sorting for cell markers. P0 post-1 st sorting, cells in passage just after sorting. P1 before second sorting: first cell passage after 1 st sorting, before second sorting. P1, Post-2nd sorting: first cell passage after sorting for both EphA4 and CD56. Presence of a cell marker on the sorted cells is indicated by a positive sign ("+"), its absence is indicated by a negative sign ("−").

In vitro and in vivo Characterizations of CD56 or EphA4 Single Sorted and CD56/EphA4 or EphA4/CD56 Double Sorted Pancreatic Cells A. Materials and Methods Pre-purified cells from digested human pancreas donor HD496 were cultured with SM95+M7 (4:1) at P0. When the culture dish reached confluence, the cells were divided into two portions, one portion was sorted with CD56 the other one sorted with EphA4. Both positively and negatively sorted cells were collected and put in P1 culture. When the culture dish reached confluence, cells were collected and the CD56− and EphA4− cells and half of the CD56+ and EphA4+ cells were directly passaged to P2, and the other half of the positively sorted cells went through secondary sorting with different antibodies. Finally the sortings yielded eight cell groups (FIG. 17).
CD56+
CD56−
EphA4+
EphA4−
CD56+/EphA4+
CD56+/EphA4−
EphA4+/CD56+
EphA4+/CD56−

B. Part 1. In vitro Characterization of CD56 or EphA4 Single Sorted and CD56/EphA4 or EphA4/CD56 Double Sorted Pancreatic Dells Cells were divided into groups (FIG. 17). Group1 was first sorted with CD56 at the end of P0, and then sorted with EphA4 at the end of P1. The other group was fist sorted with EphA4 at the end of P0 and then sorted with CD56 at the end of P1. The cells were then divided into eight groups, as follows:
CD56+
CD56−
EphA4+
EphA4−
CD56+/EphA4+
CD56+/EphA4−
EphA4+/CD56+
EphA4+/CD56−

(1). In Vitro Characterizations

The different cell group samples were collected for qRT-PCR to test gene expressions of CD56, EphA4, Insulin, Glucagon, PDX1, Glut2, CK19 and Amylase.

The qRT-PCR samples were collected at four different time points, namely P0 before sorting, P0 immediately after sorting, P1 before $2^{nd}$ sorting and P1 after $2^{nd}$ sorting.

(2). Results

After first sorting, the insulin expressions of CD56 positive and EphA4 positive cells were 22 and 15 times higher than the negative ones respectively, while the glucagon expressions were 27 and 17 times higher in the positive cells. The GluT2 expression in the CD56 positive and Eph positive cells was 3~4 times higher than the negative ones. After second sorting, the insulin and glucagon gene expressions of CD56/EphA4 double positive cells reached or exceeded the P0 level and were 4~100 times higher than the other groups (Table 10).

(2). Results

Figure 26B:
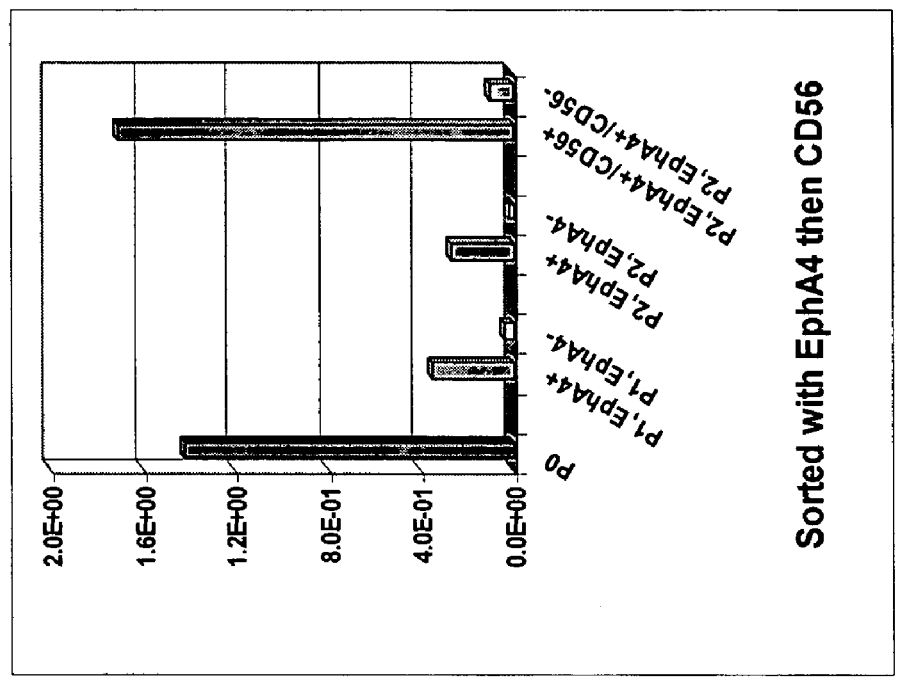
FIG. 26*b*: Cells sorted first for EphA4 at the end of P0 and then for CD56 at the end of P1. As shown, insulin expression was determined by qRT-PCR at P0, P1 and P2. Presence of a cell marker on the sorted cells is indicated by a positive sign ("+"), its absence is indicated by a negative sign ("−").
Figure 26A:
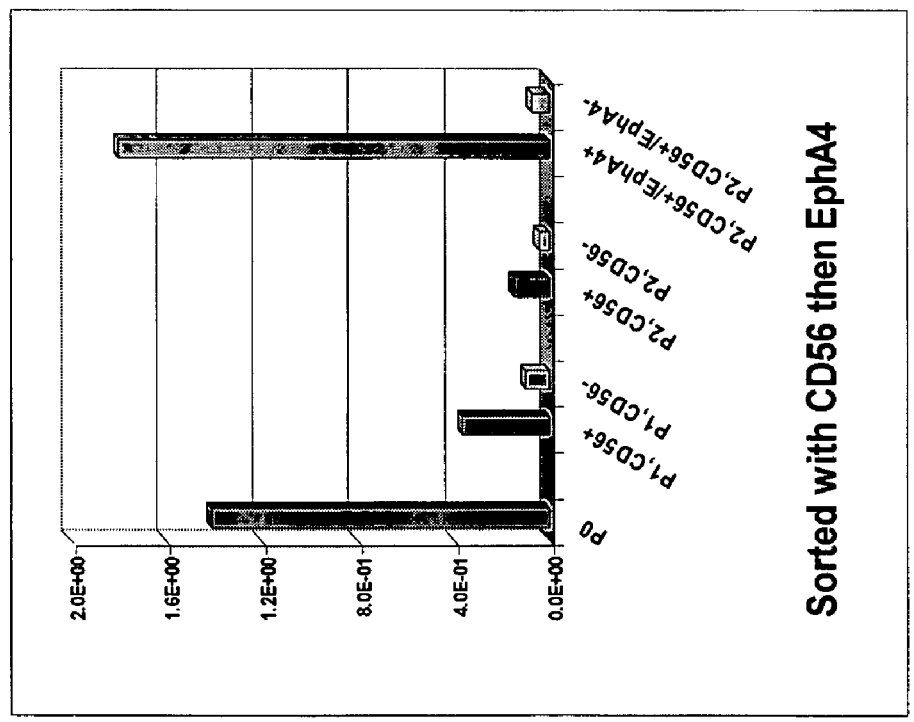
FIGS. 26*a* and *b* show a comparison of expression of insulin in CD56/EphA4 single sorted cells and for cells sorted first for CD56 and then for EphA4 against cells sorted first for EphA4 and then for CD56.

As shown in FIG. 26, both groups had similar patterns of insulin expression. The different sorting sequence did not change the outcome.

TABLE 10

Gene Expression of CD56, EphA4, Insulin, Glucagon, PDX1, Glut2, CK19, and Amylase in CD56, EphA4, or Double Sorted Cells at Different Cell Passages

| | Cell | Ins/$\beta$-actin ratio | Gcg/$\beta$-actin ratio | PDX/$\beta$-actin ratio | GLUT2/$\beta$-actin ratio | Amy/$\beta$-actin ratio | NCAM/$\beta$-actin ratio | CK19/$\beta$-actin ratio | Pax4/$\beta$-actin ratio | SA22/$\beta$-actin ratio |
|---|---|---|---|---|---|---|---|---|---|---|
| P0, before sorting | HD495B | 6.7E−01 | 1.2E−02 | 3.3E−03 | 2.5E−04 | 6.5E−02 | 6.6E−03 | 1.9E−01 | 0.0E+00 | 4.2E−04 |
| P0, post-1st sorting | CD56+ | 4.0E+00 | 5.2E−02 | 1.0E−02 | 8.5E−04 | 1.1E−01 | 2.8E−02 | 3.7E−01 | 0.0E+00 | 8.0E−04 |
| | CD56− | 1.8E−01 | 1.9E−03 | 4.1E−03 | 2.7E−04 | 9.4E−02 | 1.9E−03 | 1.9E−01 | 0.0E+00 | 2.1E−04 |
| | EphA4+ | 4.5E+00 | 5.7E−02 | 1.4E−02 | 8.0E−04 | 1.0E−01 | 3.0E−02 | 3.5E−01 | 3.5E−06 | 9.1E−04 |
| | EphA4− | 3.0E−01 | 3.3E−03 | 4.4E−03 | 2.2E−04 | 1.0E−01 | 1.8E−03 | 1.7E−01 | 0.0E+00 | 2.8E−04 |
| P1, before 2nd sorting | CD56+ | 6.1E+01 | 1.7E−02 | 1.5E−03 | 1.5E−04 | 1.5E−02 | 3.6E−03 | 2.9E−01 | 5.2E−06 | 2.2E−03 |
| | CD56− | 2.7E−02 | 8.6E−04 | 6.8E−04 | 1.3E−04 | 1.3E−02 | 9.4E−04 | 2.2E−01 | 0.0E+00 | 8.9E−04 |
| | EphA4+ | 1.0E+00 | 2.9E−02 | 1.4E−03 | 1.7E−04 | 1.3E−02 | 5.2E−03 | 2.6E−01 | 1.6E−05 | 2.2E−03 |
| | EphA4− | 2.3E−02 | 9.4E−04 | 7.6E−04 | 8.4E−05 | 1.8E−02 | 1.4E−03 | 2.6E−01 | 0.0E+00 | 1.1E−03 |
| P1, post-2nd-sorting | CD56+/Eph+ | 6.4E−01 | 3.1E−02 | 1.5E−03 | 2.6E−04 | 1.1E−02 | 7.2E−03 | 4.2E−01 | 4.8E−06 | 3.6E−03 |
| | CD56+/Eph− | 1.6E−01 | 5.3E−03 | 9.7E−04 | 1.7E−04 | 1.6E−02 | 2.5E−03 | 4.5E−01 | 0.0E+00 | 1.5E−03 |
| | CD56−/Eph+ | 1.5E−01 | 8.7E−03 | 2.5E−03 | 3.9E−04 | 1.9E−02 | 7.8E−03 | 4.0E−01 | 0.0E+00 | 6.5E−03 |
| | CD56−/Eph− | 4.7E−03 | 2.5E−04 | 7.7E−04 | 1.1E−04 | 1.5E−02 | 9.7E−04 | 3.6E−01 | 0.0E+00 | 7.8E−04 |
| | Eph+/CD56+ | 1.1E+00 | 3.2E−02 | 1.2E−03 | 1.2E−04 | 1.4E−02 | 5.9E−03 | 3.4E−01 | 0.0E+00 | 3.5E−03 |
| | Eph+/CD56− | 2.6E−01 | 1.2E−02 | 6.6E−04 | 1.1E−04 | 1.3E−02 | 2.5E−03 | 3.3E−01 | 0.0E+00 | 1.5E−03 |
| | Eph−/CD56+ | 3.5E−02 | 4.3E−03 | 2.1E−03 | 3.2E−04 | 1.4E−02 | 2.9E−03 | 3.9E−01 | 0.0E+00 | 2.7E−03 |
| | Eph−/CD56− | 2.6E−02 | 1.4E−03 | 5.0E−04 | 5.8E−05 | 1.3E−02 | 9.2E−04 | 2.7E−01 | 0.0E+00 | 1.1E−03 |

(3). Summary:

Both EphA4+ and CD56+ cells have much higher insulin/glucagon/PDX-1/GLUT2 levels, suggesting that the CD56/EphA4 sorting can enrich endocrine lineage cells, which include both β and α cells.

Overlapping between CD56 and EphA4 expression suggests that these markers co-exist on the surface of certain cell population.

CD56 and EphA4 sorting did not significantly affect Amylase/CK19 expressing cells, suggesting that they are exclusive markers for endocrine cells.

EphA4 levels increased after proliferation in GM1SB, which suggests that EphA4+cells might represent some expandable endocrine cell population.

B. Part 2. Comparisons of Insulin Expression in CD56/EphA4 Single Sorted and CD56/EphA4 or EphA4/CD56 Double Sorted Pancreatic Dells (1). Cells Cell sorting procedure was as described above. All the cells were cultured in SM95+M7 (4:1, day P0) or SM95 in the following passages.

Cells were divided into two groups one group was sorted with CD56 at the end of P0 and then sorted with EphA4 at the end of P1. The other group was sorted with EphA4 at the end of P0 and then with CD56 at P1.

Insulin qRT-PCR was tested for both groups at P0, P1 and P2 to compare whether the different sorting sequence would change the outcome.

B. Part 3 Comparisons of Insulin Expression in SM95 and DM Cultured CD56/EphA4 Single Sorted and CD56/EphA4 or EphA4/CD56 Double Sorted Pancreatic Dells (1). Cells Cell sorting procedure was as described above. All the cells were cultured in SM95+M7 (4:1, ay P0) or SM95 in the following passages.

Cells were divided into two groups; one group was sorted with CD56 at the end of P0 and then sorted with EphA4 at the end of P1. The other group was sorted with EphA4 at the end of P0 and then with CD56 at P1. The cells were cultured in SM95 before sorting. After the second sorting, the sorted cells were divided into two groups. One group was kept in SM95 and the other group was treated with DM (differentiation medium) for three days.

The formula of DM is as follows

Basal medium: DMEM/F12 (1:1)+N2+B27
(note: DMEM mixed with Ham's F12 media in a 1:1 ratio is available premixed from a number of suppliers, including AthenaES, Baltimore, Md., HyClone, Logan, Utah, and Mediatech, Inc., Herndon, Va. N2 and B27 are commercially available media additives.)

Supplements:

10 mM Nicotinamide (available from, e.g., Sigma-Aldrich, Inc., St. Louis, Mo.);

10 ng/ml recombinant human growth hormone (available from, e.g., Humatrope®, Eli Lilly & Co., Indianapolis, Ind.);

200 nM of the peptide IGLHDPSHGTLPNGS (SEQ ID NO:1);

10 ng/ml Exendin-4 (Epoch Biolabs, Sugar Land, Tex.);

2 ng/ml human recombinant betacellulin (R&D Systems, Inc., Minneapolis, Minn.); and, 100 nM Z-VAD-FMK (a pan-caspase inhibitor; Epoch Biolabs, Sugar Land, Tex.)

Insulin qRT-PCR was tested for both groups at P2 to compare whether the different culture media would change the outcome.

(2). Results

Figure 27B:
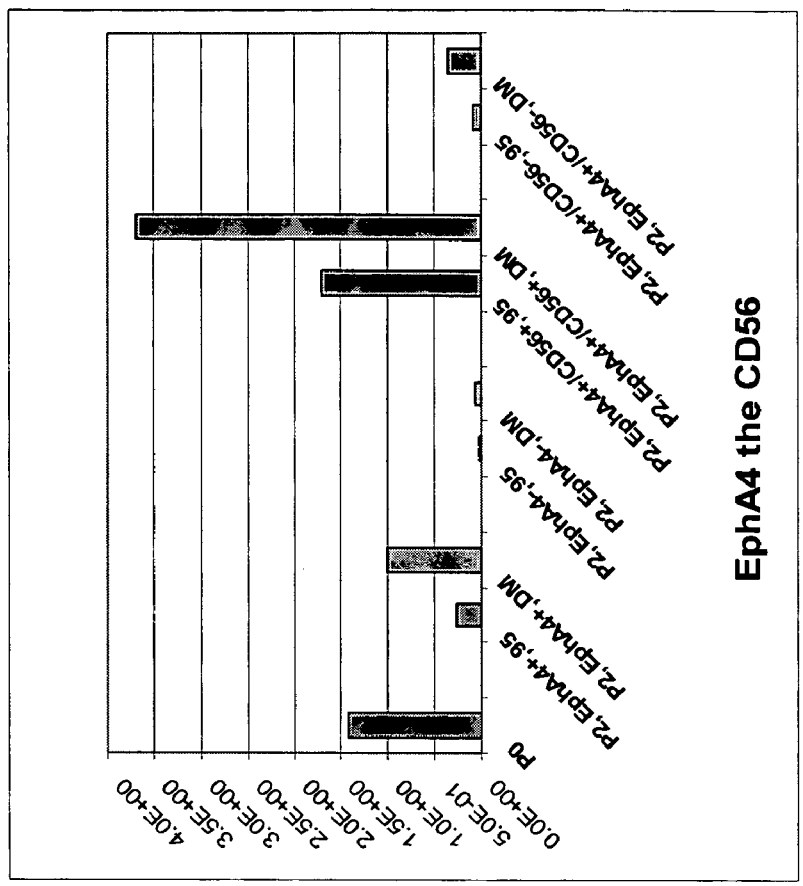
FIG. 27*b*: Cells sorted first for EphA4 at the end of P0 and then for CD56 at the end of P1. Both Figures: after the second sorting, the sorted cells were divided into two groups. One group was kept in medium SM95 (shown as "95" in the graph) and the other was treated with differentiation medium ("DM," in the graph) for three days. Insulin was tested for both groups at P2 by qRT-PCR. Insulin expression was twice as high in the group of cells treated with DM. Presence of a cell marker on the sorted cells is indicated by a positive sign ("+"), its absence is indicated by a negative sign ("−").
Figure 27A:
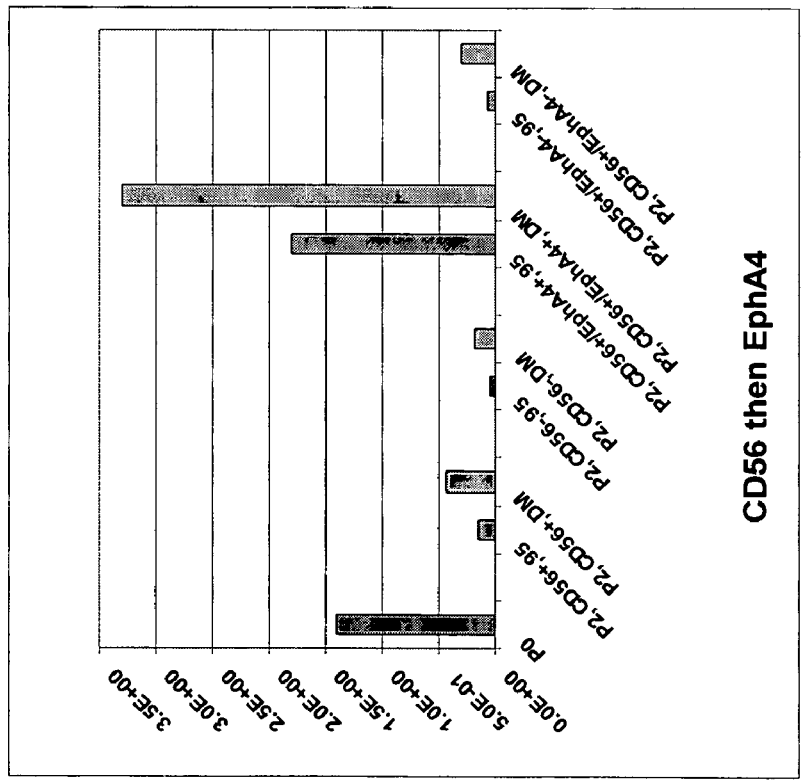
FIGS. 27*a* and *b* show a comparison of expression of insulin in CD56/EphA4 single sorted cells and for cells sorted first for CD56 and then for EphA4 against cells sorted first for EphA4 and then for CD56 after culturing in different media.

The insulin expression after DM treatment was twice as high as the non-DM-treated groups and reached levels higher than that seen at P0 (FIG. 27).

B. Part 4. In Vivo Characterization of EPHA4 Sorted and Proliferated Human Pancreatic Cells (1). Cells Cell sorting procedure was as described above. Human pancreatic cells were seeded in SM95+M7 (4:1) for P0 culture. EphA4 sorting was performed at P1, and then the cells were proliferated in SM95 until P5. When the culture dish was confluent, cells were trypsinized and collected for encapsulation. After the cells were well mixed with Alginate solution, the mixture was dropped into calcium solution to form gel capsules through an airflow head-jet. The capsules were then cultured in medium 4 until transplant.

(2) Experimental Animals

Normal C57/black mice were made diabetic by a single intraperitoneal injection of streptozotocin at 220 mg/dl. When the blood glucose of injected animals reached 400 mg/dl or above, the encapsulated human pancreatic cells were implanted into the peritoneal cavity through a mid-line abdominal incision.

The transplanted animals were followed up by measuring blood glucose weekly. The animals were sacrificed when their blood glucose reached normal range (<200 mg/dl). Biopsy of pancreases and blood samples were collected. Blood human C-peptide was measured for verifying the insulin secretion of the grafts.

In one exemplar study, three animals were studied. One received passage5- EphA4 positively sorted cells as described above, one was a non-transplanted diabetic mouse and the other one was normal control.

(3) Results

Figure 28:
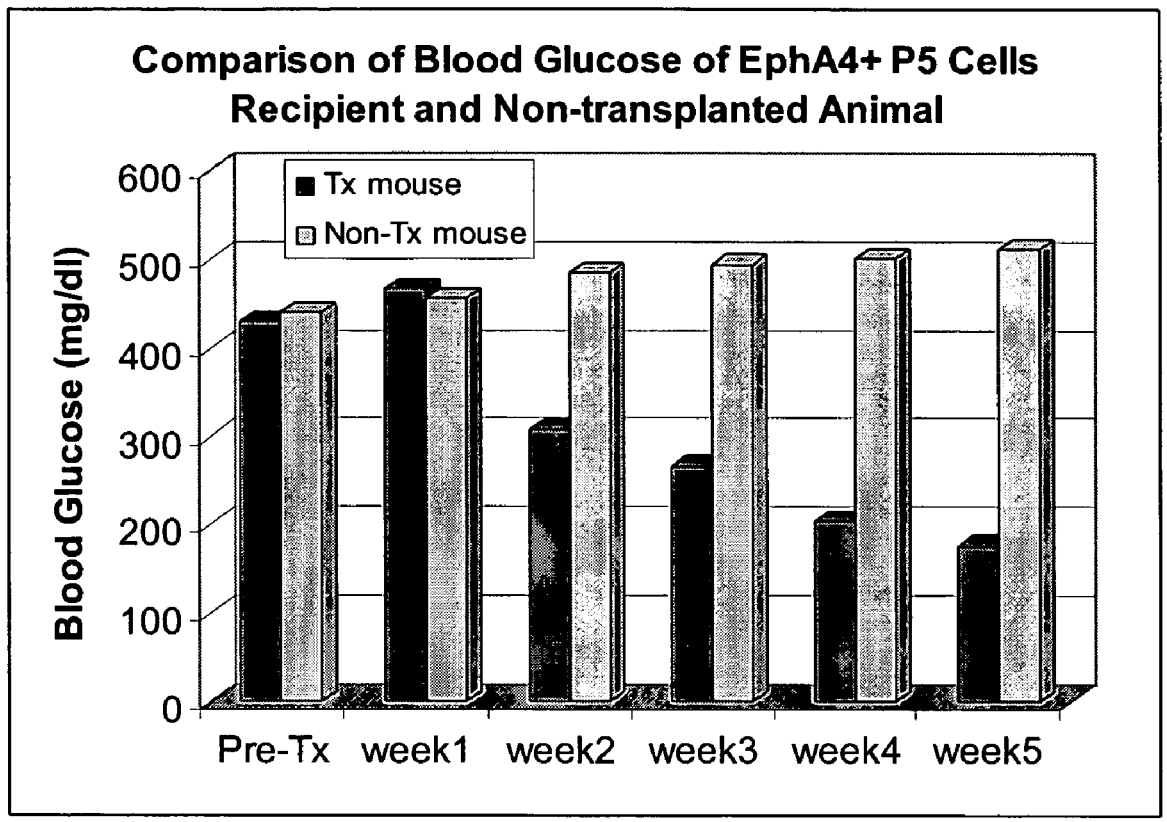
FIG. 28 shows the changes in blood glucose of four diabetic mice which recovered from hyperglycemia after transplantation with encapsulated CD56 or EphA4 sorted human pancreatic cells, or with encapsulated EphA4-CD56 double selected human pancreatic cells, as described in the Examples.

Table 11 and FIG. 28 present information about the mice in this study. The blood glucose of the transplanted animal showed a recovery from pre-Tx hyperglycemia (>400 mg/dl) to the near normal range (<300 mg/dl) within five weeks, while the non-transplanted diabetic mouse was hyperglycemic through out the study period.

TABLE 11

Comparison of blood glucose (mg/dl) of diabetic C57 mouse transplanted with encapsulated P5 EphA4 sorted B cells (sorted at P0) and non-transplanted diabetic mouse

| | Pre-Tx | Post-Tx week 1 | week 2 | week 3 | week 4 | Week 12 |
|---|---|---|---|---|---|---|
| Tx mouse | 454 | 295 | 382 | 378 | 370 | 280 |
| Non-Tx mouse | 441 | 457 | 486 | 495 | 501 | died |

Table 12 shows the human blood C-peptide of the experimental animals. The blood human C-peptide test kit (ELISA) does not cross react with rodent C-peptide, so normally the rodent blood human-peptide should be less than 0.02, which is the test background. If the transplanted animal has human C-peptide in blood, it means the human pancreatic cell graft is functioning. In this study, the EphA4+ cell mouse recipient had 0.64 ng/ml human C-peptide in the blood, while the non-transplanted normal control mouse only had some trace value (0.005 ng/ml) (Table 12).

TABLE 12

Human C-peptide concentrations in the blood of a transplanted mouse and a control normal mouse

| Animal | Blood Human C-peptide (ng/ml) |
|---|---|
| Recipient of EphA4+ Human Pancreatic cells | 0.64 |
| Normal (non-transplanted) control | 0.005 |

(4) Conclusions

EphA4 sorting enriches all the pancreatic endocrine lineage cells including both α- and β-lineage cells. This means these sorted cells have the potential not only to cure hyperglycemia but also to prevent hypoglycemia, which is a dangerous complication of diabetes. EphA4 and CD56 double sorting strengthened the endocrine cell enrichment effect. CD56 and EphA4 sorting methods make it possible to utilize the endocrine lineage cells from the human pancreas to selectively expand the endocrine cell population and develop regenerated islets.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of obtaining a culture of propagating pancreatic cells comprising:
    (a) isolating pancreatic cells from a pancreas;
    (b) contacting the pancreatic cells with an EphA4 binding reagent;
    (c) selecting pancreatic cells that specifically bind to the EphA4 binding reagent; and
    (d) separating the selected pancreatic cells from pancreatic cells that do not bind the EphA4 binding reagent to obtain a culture of propagating EphA4$^+$ pancreatic cells, wherein the EphA4$^+$ pancreatic cells have the capacity to differentiate into insulin producing cells.

2. The method of claim 1, wherein the EphA4 binding reagent is labeled.

3. The method of claim 1, wherein the step of selecting is done by fluorescence activated cell sorting.

4. The method of claim 1, wherein the step of selecting is done by panning.

5. The method of claim 1, wherein the EphA4-binding reagent is an antibody that specifically binds to EphA4 protein.

6. The method of claim 1, wherein the pancreas is from a human.

7. The method of claim 1, further comprising propagating the cells of step (d) and differentiating the cells into an aggregate of insulin producing cells.

8. The method of claim 7, wherein the step of differentiating the cells comprises culturing the cells on plates coated with collagen IV.

9. The method of claim 7, wherein the step of differentiating the cells comprises culturing the cells in a medium comprising a differentiation factor.

10. The method of claim 9, wherein the differentiation factor is selected from the group consisting of hepatocyte growth factor, keratinocyte growth factor, and exendin-4.

11. The method of claim 10, wherein the differentiation factor is hepatocyte growth factor.

12. A method of claim 1, further comprising the steps of:
    (a) contacting the pancreatic cells with a CD56 binding reagent;
    (b) selecting pancreatic cells that specifically bind to the CD56 binding reagent; and
    (c) separating the selected pancreatic cells from pancreatic cells that do not bind the CD56 binding reagent to obtain a culture of propagating CD56$^+$ pancreatic cells, wherein the steps utilizing the CD56 binding reagent are performed before or after contacting the pancreatic cells with the EphA4 binding reagent.

13. A method of producing an aggregate of insulin-producing pancreatic cells comprising the steps of:
    (a) isolating pancreatic cells from a pancreas;
    (b) contacting the pancreatic cells with an EphA4 binding reagent;
    (c) selecting pancreatic cells that specifically bind to the EphA4 binding reagent;
    (d) separating the selected pancreatic cells from pancreatic cells that do not bind the EphA4 binding reagent to obtain a culture of propagating EphA4$^+$ pancreatic cells; and
    (e) differentiating the propagating EphA4$^+$ pancreatic cell culture into an aggregate of insulin producing pancreatic cells.

14. The method of claim 13, wherein the EphA4-binding reagent is labeled.

15. The method of claim 13, wherein the step of selecting is done by fluorescence activated cell sorting.

16. The method of claim 13, wherein the step of selecting is done by panning.

17. The method of claim 13, wherein the EphA4-binding reagent is an antibody that specifically binds to the EphA4 protein.

18. The method of claim 13, wherein the pancreas is from a human.

19. The method of claim 13, wherein the step of differentiating the cells comprise culturing the cells on plates coated with collagen IV.

20. The method of claim 13, wherein the step of differentiating the cells comprises culturing the cells in a medium comprising a differentiation factor.

21. The method of claim 13, wherein the differentiation factor is selected from the group consisting of hepatocyte growth factor, keratinocyte growth factor, and exendin-4.

22. The method of claim 21, wherein the differentiation factor is hepatocyte growth factor.

23. A method of claim 13, further comprising the steps of:
    (a) contacting the pancreatic cells with a CD56 binding reagent;
    (b) selecting pancreatic cells that specifically bind to the CD56 binding reagent; and
    (c) separating the selected pancreatic cells from pancreatic cells that do not bind the CD56 binding reagent to obtain a culture of propagating CD56$^+$ pancreatic cells, wherein the steps utilizing the CD56 binding reagent are performed before or after contacting the pancreatic cells with the EphA4 binding reagent.

24. A method of providing insulin to a mammal in need thereof, the method comprising the steps of:
    (a) isolating pancreatic cells from a pancreas;
    (b) contacting the pancreatic cells with an EphA4 binding reagent;
    (c) selecting pancreatic cells that specifically bind to the EphA4 binding reagent;
    (d) separating the selected pancreatic cells from pancreatic cells that do not bind the EphA4 binding reagent to obtain a culture of propagating EphA4$^+$ pancreatic cells; and
    (e) implanting into the mammal the propagating pancreatic cells in an amount sufficient to produce a measurable amount of insulin in the mammal.

25. The method of claim 24, wherein the EphA4 binding reagent is labeled.

26. The method of claim 24, wherein the step of selecting is done by fluorescence activated cell sorting.

27. The method of claim 24, wherein the step of selecting is done by panning.

28. The method of claim 24, wherein the EphA4 binding reagent is an antibody that specifically binds to the EphA4 protein.

29. The method of claim 24, wherein the pancreas is from a human.

30. The method of claim 24, wherein the propagating pancreatic cells differentiate into aggregates of insulin producing pancreatic cells after implantation into the mammal.

31. The method of claim 24, wherein before implantation into the mammal, the propagating pancreatic cell culture is differentiated into an aggregate of insulin producing pancreatic cells.

32. The method of claim 31, wherein the step of differentiating the cells comprises culturing the cells on plates coated with collagen IV.

33. The method of claim 31, wherein the step of differentiating the cells comprises culturing the cells in a medium comprising a differentiation factor.

34. The method of claim 33, wherein the differentiation factor is selected from the group consisting of hepatocyte growth factor, keratinocyte growth factor, and exendin-4.

35. The method of claim 34, wherein the differentiation factor is hepatocyte growth factor.

36. The method of claim 24, wherein the mammal is a human.

37. A method of claim 24, further comprising the steps of:
(a) contacting the pancreatic cells with a CD56 binding reagent;
(b) selecting pancreatic cells that specifically bind to the CD56 binding reagent; and
(c) separating the selected pancreatic cells from pancreatic cells that do not bind the CD56 binding reagent to obtain a culture of propagating $CD56^{30}$ pancreatic cells, wherein the steps utilizing the CD56 binding reagent are performed before or after contacting the pancreatic cells with the EphA4 binding reagent.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:peptide
    supplement to DMEM/Ham's F12 (1:1) + N2 + B27
    basal medium (differentiation medium (DM))

```
<400> SEQUENCE: 1

Ile Gly Leu His Asp Pro Ser His Gly Thr Leu Pro Asn Gly Ser
1               5                   10                  15
```